(12) United States Patent
Lewinsohn et al.

(10) Patent No.: US 9,040,233 B2
(45) Date of Patent: May 26, 2015

(54) METHODS FOR DETECTING A MYCOBACTERIUM TUBERCULOSIS INFECTION

(71) Applicants: Oregon Health & Science University, Portland, OR (US); The Government of the United States of America, dba The Department of Veterans Affairs, Washington, DC (US)

(72) Inventors: David M. Lewinsohn, Portland, OR (US); Deborah A. Lewinsohn, Portland, OR (US)

(73) Assignees: Oregon Health & Science University, Portland, OR (US); The United States of America, DBA The Department of Veteran Affairs, Washington, DC (US)

( * ) Notice: Subject to any disclaimer, the term of this patent is extended or adjusted under 35 U.S.C. 154(b) by 0 days.

(21) Appl. No.: 13/719,124

(22) Filed: Dec. 18, 2012

(65) Prior Publication Data

US 2013/0101523 A1    Apr. 25, 2013

Related U.S. Application Data

(63) Continuation of application No. 13/244,126, filed on Sep. 23, 2011, now Pat. No. 8,361,707, which is a continuation of application No. 12/282,862, filed as application No. PCT/US2007/006534 on Mar. 14, 2007, now Pat. No. 8,053,181.

(51) Int. Cl.

| | |
|---|---|
| *G01N 33/50* | (2006.01) |
| *G01N 33/569* | (2006.01) |
| *G01N 33/68* | (2006.01) |
| *A61K 39/04* | (2006.01) |
| *C07K 14/35* | (2006.01) |
| *A61K 38/00* | (2006.01) |
| *A61K 39/00* | (2006.01) |

(52) U.S. Cl.
CPC ............ *G01N 33/6893* (2013.01); *A61K 38/00* (2013.01); *A61K 39/04* (2013.01); *A61K 2039/53* (2013.01); *C07K 14/35* (2013.01); *G01N 33/505* (2013.01); *G01N 33/5695* (2013.01); *G01N 2333/35* (2013.01)

(58) Field of Classification Search
CPC ... A61K 39/04; C07K 14/35; G01N 33/5695; G01N 33/505; G01N 2333/35; G01N 33/50; G01N 33/5044
USPC .......... 424/248.1, 190.1, 184.1, 234.1, 185.1, 424/9.1; 435/7.1, 4, 7.2
See application file for complete search history.

(56) References Cited

U.S. PATENT DOCUMENTS

| | | | |
|---|---|---|---|
| 6,294,328 B1 | 9/2001 | Fleischmann et al. | |
| 6,384,018 B1 | 5/2002 | Content et al. | |
| 6,555,653 B2 | 4/2003 | Alderson et al. | |
| 7,074,559 B2 | 7/2006 | Kapur et al. | |
| 7,332,340 B2 | 2/2008 | Tyagi et al. | |
| 7,364,869 B2 | 4/2008 | Nixon et al. | |
| 7,424,370 B2 | 9/2008 | Sachdeva et al. | |
| 7,510,718 B2 | 3/2009 | Krohn et al. | |
| 7,767,209 B2 | 8/2010 | Staib et al. | |
| 7,842,299 B2 * | 11/2010 | Lewinsohn et al. | ........ 424/248.1 |
| 7,867,704 B2 | 1/2011 | Kapur et al. | |
| 8,053,181 B2 * | 11/2011 | Lewinsohn et al. | ................ 435/4 |
| 8,101,192 B2 * | 1/2012 | Lewinsohn et al. | ........ 424/248.1 |
| 8,299,232 B2 | 10/2012 | Singh et al. | |
| 8,361,707 B2 * | 1/2013 | Lewinsohn et al. | ................ 435/4 |
| 8,440,206 B2 * | 5/2013 | Lewinsohn et al. | ........ 424/248.1 |
| 8,623,609 B2 * | 1/2014 | Gennaro | ........................ 435/7.2 |
| 8,658,350 B2 * | 2/2014 | Lewinsohn et al. | ................ 435/4 |
| 8,691,502 B2 * | 4/2014 | Kupper et al. | ..................... 435/5 |
| 2002/0061569 A1 | 5/2002 | Haselbeck et al. | |
| 2002/0098200 A1 | 7/2002 | Campos-Neto et al. | |
| 2002/0176867 A1 | 11/2002 | Anderson et al. | |
| 2002/0192229 A1 | 12/2002 | Flyer et al. | |
| 2003/0147897 A1 | 8/2003 | Anderson et al. | |
| 2003/0175725 A1 | 9/2003 | Kapur et al. | |
| 2003/0236393 A1 | 12/2003 | Trucksis | |
| 2004/0029129 A1 | 2/2004 | Wang et al. | |
| 2004/0057963 A1 | 3/2004 | Anderson et al. | |
| 2004/0141985 A1 | 7/2004 | Lalvani et al. | |
| 2005/0074822 A1 | 4/2005 | Nixon et al. | |
| 2005/0123511 A1 | 6/2005 | McCreavy et al. | |

(Continued)

FOREIGN PATENT DOCUMENTS

| | | |
|---|---|---|
| EP | 1 484 405 | 12/2004 |
| EP | 2 207 035 | 7/2010 |

(Continued)

OTHER PUBLICATIONS

Ahmad, Clinical and Developmental Immunology vol. 2011, 17 pages.*
Lewinsohn et al, PLOS One | www.plosone.org Jun. 2013 | vol. 8 | Issue 6 | e7016, 9 pages.*
McNerney et al, The Journal of Infectious Diseases 2012;205:S147-58.*
Walzl et al, Nature Reviews | Immunology vol. 11 | May 2011 | 343-358.*

(Continued)

*Primary Examiner* — Nita M Minnifield
(74) *Attorney, Agent, or Firm* — Klarquist Sparkman, LLP

(57) ABSTRACT

Methods for detecting an infection with *Mycobacterium tuberculosis* (Mtb) in a subject are disclosed. The methods include detecting the presence of CD8+ T cells that specifically recognize an Mtb polypeptide. The methods include in vitro assays for detecting the presence of CD8+ T cells in a biological sample, and in vivo assays that detect a delayed type hypersensitivity reaction. The methods can also include detecting Mtb polypeptides and polynucleotides. Reagents for the detection of an Mtb infection are also disclosed.

19 Claims, 8 Drawing Sheets

(56) References Cited

U.S. PATENT DOCUMENTS

| | | | |
|---|---|---|---|
| 2005/0288866 A1 | 12/2005 | Sachdeva et al. | |
| 2007/0026020 A1 | 2/2007 | Ernst et al. | |
| 2007/0036816 A1 | 2/2007 | Campos-Neto et al. | |
| 2007/0042383 A1 | 2/2007 | Kapur et al. | |
| 2008/0124549 A1 | 5/2008 | Lee et al. | |
| 2009/0070897 A1 | 3/2009 | Goldman et al. | |
| 2009/0124549 A1 | 5/2009 | Lewinsohn et al. | |
| 2009/0324503 A1 | 12/2009 | Lewinsohn et al. | |
| 2010/0129391 A1 | 5/2010 | Reed et al. | |
| 2011/0014224 A1 | 1/2011 | Lewinsohn et al. | |
| 2011/0183342 A1 | 7/2011 | Lewinsohn et al. | |
| 2011/0268758 A1 | 11/2011 | Campos-Neto et al. | |
| 2012/0014881 A1 | 1/2012 | Lewinsohn et al. | |
| 2012/0107341 A1 | 5/2012 | Lewinsohn et al. | |
| 2012/0258126 A1 | 10/2012 | Scholler et al. | |
| 2013/0101523 A1* | 4/2013 | Lewinsohn et al. | 424/9.81 |
| 2014/0004151 A1* | 1/2014 | Sette et al. | 424/248.1 |
| 2014/0050776 A1* | 2/2014 | Coller et al. | 424/450 |
| 2014/0086948 A1* | 3/2014 | Mettens et al. | 424/190.1 |

FOREIGN PATENT DOCUMENTS

| | | |
|---|---|---|
| WO | WO 98/44119 | 10/1998 |
| WO | WO 98/53075 | 11/1998 |
| WO | WO 99/24577 | 5/1999 |
| WO | WO 01/51639 | 7/2001 |
| WO | WO 01/62893 | 8/2001 |
| WO | WO 01/74130 | 10/2001 |
| WO | WO 01/79257 | 10/2001 |
| WO | WO 02/077183 | 10/2002 |
| WO | WO 03/033530 | 4/2003 |
| WO | WO 2005/021790 | 3/2005 |
| WO | WO 2005/076010 | 8/2005 |
| WO | WO 2005/090988 | 9/2005 |
| WO | WO 2007/106536 | 9/2007 |
| WO | WO 2007/106560 | 9/2007 |
| WO | WO 2009/039854 | 4/2009 |
| WO | WO 2010/034007 | 3/2010 |
| WO | WO 2011/063283 | 5/2011 |

OTHER PUBLICATIONS

Abebe et al, "Modulation of Cell Death by *M. tuberculosis* as a Strategy for Pathogen Survival," *Clinical and Developmental Immunology* vol. 2011, Article ID 678570, 11 pages (2011).

Ahmad, "Pathogenesis, Immunology, and Diagnosis of Latent *Mycobacterium tuberculosis* Infection," *Clinical and Developmental Immunology* vol. 2011, Article ID 814943, 17 pages (2011).

Arend et al., "Antigentic Equivalence of Human T-Cell Responses to *Mycobacterium Tuberculosis*-Specific RD1-Encoded Protein Antigens ESAT-6 and Culture Filtrate Protein 10 and to Mixtures of Synthetic Peptides," *Infection and Immunity* 68(6):3314-3321 (Jun. 2000).

Berzofsky et al., "Progress on new vaccine strategies for the immunotherapy and prevention of cancer," *J. Clin. Invest.* 113(11):1515-1525 (Jun. 2004).

Bixler et al., "B Cell Recognition of Protein Antigens-Perspectives from the Submolecular Level," *Synthetic Vaccines* 1:39-71 (1987).

Blythe et al., "An Analysis of the Epitope Knowledge Related to Mycobacteria," *Immunome Research* 3(10) 14 pages (2007).

Boom, "New TB Vaccines: is there a requirement for CD8$^+$ T Cells?," *Journal of Clinical Investigation* 117(8):2092-2094 (Aug. 2007).

Bowie et al., "Deciphering the Message in Protein Sequences: Tolerance to Science Amino Acid Substitutions," *Science* 247:1306-1310 (1990).

Braibant et al., "The ATP Binding Cassette (ABC) Transport Systems of *Mycobacterium tuberculosis*," *FEMS Microbiol. Rev.* 24(4):449-467 (Oct. 2000).

Brosch et al., "Genome Plasticity of BCG and Impact on Vaccine Efficacy," *PNAS* 104:5596-5601 (Mar. 19, 2007).

Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," *Journal of Cell Biology* 111:2129-2138 (1990).

Camus et al., "Re-annotation of the Genome Sequence of *Mycocaterium tuberculosis* H37Rv," *Microbiology* 148:2967-2973 (2002).

Chaitra et al., "Defining Putative T Cell Epitopes from PE and PPE Families of Proteins of *Mycobacterium tuberculosis* with Vaccine Potential," *Vaccine* 23:1265-1272 (2005).

Cho et al., "Current Issues on Molecular and Immunological Diagnosis of Tuberculosis," *Yonsei Medical Journal* 48(3):347-359 (2007).

Cole et al., "Deciphering the Biology of *Mycobaterium Tuberculosis* from the Complete Genome Sequence," *Nature* 393:537-544 (Jun. 1998).

Creighton, *Protein Structure: A Practical Approach*, pp. 184-186 (1989).

Creighton, *Proteins: Structures and Molecular Properties*, pp. 314-315 (1984).

Database Accession No. P0A4W4, "Uncharacterized ABC Transporter ATP-Binding Protein Rv1273c/MT1311," 3pp. (Mar. 2005).

Database UniProt Accession No. Q6MWX8, "Rv3350c/PPE56," (Jul. 5, 2004).

Database UniProt Accession No. Q73X11_MYCPA, "MAP_2499," (Jul. 5, 2004).

Database UniProt Accession No. Q79FS8, "Rv1088/PE9," (Jul. 5, 2004).

Database UniProt Accession No. Q79G04 (Jul. 5, 2004).

Database UniProt Accession No. Q7D724, "Rv2847c/PE_PGRS42/MT2561," (Jul. 5, 2004).

Database UniProt Accession No. Q7U0P5 (Oct. 1, 2003).

Database UniProt Entry Y1273_MYCTU, "Rv1273cMT1311," (Mar. 15, 2005).

Database UniProt Entry Y1304_MYCBO, "Mb1304c," (Mar. 15, 2005).

Delogu and Fadda, "The Quest for a New Vaccine Against Tuberculosis," *Journal Infection in Developing Countries* 3(1):5-15 (2009) (Abstract only).

Doherty et al., "Tuberculosis Subunit Vaccines: From Basic Science to Clinical Testing," *Expert Opin. Biol. Ther.* 7(10):1539-1549 (2007).

Ellner, "The Emergence of Extensively Drug-Resistant Tuberculosis: A Global Health Crisis Requiring New Interventions: Part II: Scientific Advances that May Provide Solutions," *CTS* 2(1):80-84 (2008).

Fleishmann et al., "Whole-Genome Comparison of *Mycobacterium tuberculosis* Clinical and Laboratory Strains," *Journal of Bacteriology*, 184(19):5479-5490, (Oct. 2002).

Fleishmann et al., Whole genome comparison of *Mycobacterium tuberculosis* clinical and laboratory strains, Entry C137_MYCTU,*EMBL*, (2002).

Garnier et al., "The Complete Genome Sequence of *Mycobacterium bovis*," *PNAS* 100:7877-7882 (Jun. 3, 2003).

Gold et al., "Human Mucosal Associated Invariant T Cells Detect Bacterially Infected Cells," *PLoS Biology* 8(6):e1000407 (14 pages) (Jun. 2010).

Greenspan and Di Cera, "Defining Epitopes: It's Not as Easy as it Seems," *Nature Biotechnology*, 17:936-937 (Oct. 1999).

Grotzke and Lewinsohn, "Role of CD8+ T lymphocytes in control of *Mycobacterium tuberculosis* infection," *Microbes and Infection*, 7(4):776-788, (Apr. 4, 2005).

Grotzke et al., "Secreted immunodominant *Mycobacterium tuberculosis* antigens are processed by the cytosolic pathway," *Journal of Immunology* 185:4336-4343 (2010).

Grotzke et al., "The *Mycobacterium tuberculosis* Phagosome Is a HLA-1 Processing Competent Organelle," *PLoS Pathogens* 5(4):1-13 (Apr. 2009).

Gupta et al., "Current Status of TB Vaccines," *Vaccine* 25:3742-3751 (2007).

Gura et al., "Systems for Identifying New Drugs are Often Faulty," *Science* 278:1041-1042 (Nov. 1997).

Hokey et al., "Aerosol vaccines for tuberculosis: a fine line between protection and pathology," *Tuberculosis* 91:82-85 (2011).

(56) References Cited

OTHER PUBLICATIONS

Houghten et al., "Relative Importance of Position and Individual Amino Acid Residues in Peptide Antigen-Antiboy Interactions: Implications in the Mechanism of Antigenic Drift and Antigenic Shift," *Vaccines* 86:21-25 (1986).
International Search report for PCT Application No. PCT/US2007/006534; 6 pp., (Oct. 2, 2007).
International Search report for PCT Application No. PCT/US2007/006472; 7 pp., (Nov. 23, 2007).
Kawamura, "Protective Immunity Against *Mycobacterium tuberculosis*," *Kekkaku* 81(11):6887-691 (Nov. 2006) (Abstract only).
Khan et al., "Profiling antibodies to *Mycobacterium tuberculosis* by multiplex microbead suspension arrays for serodiagnosis of tuberculosis," *Clinical and Vaccine Immunology* 15(3):433-438 (Mar. 2008).
Krueger et al., "Identification of Human Antigen-Specific T Cells Using MHC Class I and Class II Tetramers," *Current Protocols in Cemtometry* 1-6 (2004).
Kumar et al., "Amino Acid Variations at a Single Residue in an Autoimmune Peptide Profoundly Affect its Properties: T-Cell Activation, Major Histocompatibility Complex Binding, and Ability to Block Experimental Allergic Encephalomyelitis," *PNAS* 87(4):1337-1341 (Feb. 1990).
Lancioni et al., "CD8$^+$ T Cells provide an immunologic signature of tuberculosis in young children," *AM J. Respor Crit Care Med* 185(2):206-212 (Jan. 15, 2012).
Lazar et al., "Transforming Growth Factor α: Mutation of Aspartic Acid 47 and Leucine 48 Results in Different Biological Activities," *Molecular and Cellular Biology*, 8:1247-1252 (Mar. 1988).
Lewinsohn et al., "Characterization of Human CD8$^+$ T Cells Reactive with *Mycobacterium tuberculosis*-infected Antigen-presenting Cells," *Journal of Experimental Medicine*, 187(10):1633-1640, (May 18, 1998).
Lewinsohn et al., "Embracing Interferon-γ Release Assays for Diagnosis of Latent Tuberculosis Infection," *Pediatric Infectious Disease Journal* 28(8):674-675 (Aug. 2009).
Lewinsohn et al., "Human Dendritic Cells Presenting Adenovirally Expressed Antigen Elicit *Mycobacterium tuberculosis*-Specific CD8+ T Cells," American Journal of Respiratory and Critical Care Medicine, 166(6):843-848, (Sep. 15, 2002).
Lewinsohn et al., "Immunodominant Tuberculosis CD8 Antigens Preferentially Restricted by HLA-B," *PLoS Pathogens* 3(9):1240-1249 (Sep. 2007).
Lewinsohn et al., "Interferon-γ release assays: new diagnostic tests for *Mycobacterium tuberculosis* infection, and their use in children," *Curr. Opin. Pediatar.* 22:71-76 (2010).
Lewinsohn et al., "Interferon-γ Release Assays: New Diagnostic Tests for *Mycobacterium tuberculosis* Infection, and Their Use in Children," *Curr. Opin. Peditar.* 22:71-76 (2010).
Lewinsohn et al., "*Mycobacterium tuberculosis*-reactive CD8+ T lymphocytes: the relative contribution of classical versus nonclassical HLA restriction," *J. Immunol* 165:925-930 (2000).
Lewinsohn et al., "TB vaccines at the turn of the century: insights into immunity to *M. tuberculosis* and modern approaches for prevention of an ancient disease," *Seminars in Respiratory Infections* 18(4):320-338 (Dec. 2003).

Lewinsohn et al., "Tuberculosis Immunology in Children: Diagnostic and Therapeutic Challenges and Opportunities," *Int. J. Tuberc. Lung Dis.* 8(5):658-674 (2004).
Li et al., "The Complete Genome Sequence of *Mycobacterium avium* Subspecies Paratuberculosis," *PNAS* 102:12344-12349 (Aug. 22, 2005).
Mazurek et al., *MMWR, Recommendations and Reports* 54(RR15):49-55 (Dec. 16, 2005).
Nosoh et al., *Protein Stability and Stabilization Through Protein Engineering*, pp. 197-217 (1991).
Nyendak et al., "New diagnostic methods for tuberculosis," *Curr. Opin. Infect. Dis.* 22:174-182 (2009).
Ottenhoff "Overcoming the Global Crisis: "Yes, We Can," but also for TB . . .?" *Eur. J. Immunol.* 39:2014-2020 (2009).
Ottenhoff et al., "Human CD4 and CD8 T Cell Response to *Mycobacterium tuberculosis*: Antigen Specifically, Function, Implications and Applications," *Handbook of Tuberculosis: Immunology and Cell Biology*, eds. Kaufman et al., 119-155 (2008) (Abstract only).
Pai et al., "Interferon-γ assays in the immunodiagnosis of tuberculosis: a systematic review," Lancet Infect. Diseases 4:761-776 (2004).
Rengarajan et al., "Genome-wide Requirements for *Mycobacterium tuberculosis* Adaptation and Survival in Macophages," *PNAS* 102(23):8324-8332 (Jun. 7, 2005).
Restifo et al., "The Promise of Nucleic Acid Vaccines," *Gene Therapy*, 7:89-92 (Jan. 2000).
Sassetti et al., "Genes Required for Mycobacterial Growth Defined by High Density Mutagenesis," *Mol. Microbiol.* 48(1):77-84 (2003).
Seki et al., "Whole Genome Sequence Analysis of *Mycobacterium Bovis* Bacillus Calmette-Guérin (BCG) Tokyo 172: A Comparative Study of BCG Vaccine Substrains," *Vaccine* 27:1710-1716 (Feb. 4, 2009).
Shams et al., "Characterization of a *Mycobacterium tuberculosis* Peptide That is Recognized by Human CD4$^+$ and CD8$^+$ T Cells in the Context of Multiple HLA Alleles," *J. Immunol.* 173:1966-1977 (2004).
Smith et al., "Human CD8$^+$ CTL Specific for the Mycobacterial Major Secreted Antigen 85A," *Journal of Immunology*, 165:7088-7095, (2000).
Steinman et al., "Immunotherapy: Bewitched, Bothered, and Bewildered No More," *Science* 305:197-200 (Jul. 2004).
Stinear et al., "Insights from the Complete Genome Sequence of *Mycobacterium marinum* on the Evolution of *Mycobacterium tuberculosis*," *Genome Research* 18:729-741 (Apr. 10, 2008).
Stinear et al., "Reductive Evolution and Niche Adaptation Inferred from the Genome of *Mycobacterium ulcerans*, the Causative Agent of Buruli Ulcer," *Genome Research* 17:192-200 (Jan. 8, 2007).
Tundup et al., "Clusters of PE and PPE genes of *Mycobacterium tuberculosis* are organized in operons: Evidence that PE Rv2431 c is co-transcribed with PPE Rv2430c and their gene products interact with each other," *Federation of European Biochemical Societies Letters* (FEBS) 580(5):1285-1293 (Feb. 20, 2006).
Wang et al., "Identification of MHC class II restricted T-cell-mediated reactivity against MHC class I binding *Mycobacterium tuberculosis* peptides," *Immunology* 132(4):482-491 (Apr. 2011).
Winthrop et al., "Interferon-gamma release assays for diagnosing *Mycobacterium tuberculosis* infection in renal dialysis patients," *Clin. J. Am. Soc. Nephrol.* 3:1357-1363 (2008).

\* cited by examiner

FIG. 3A  Identification of Antigen
FIG. 3B  Identification of 15mer Peptide within CFP10
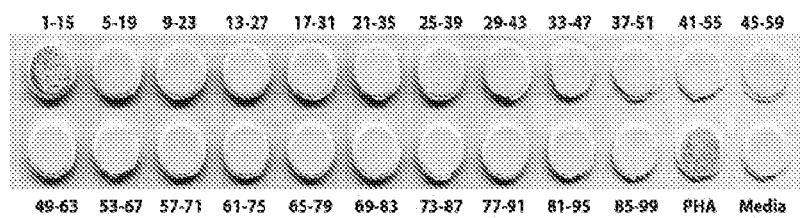
FIG. 3C  Identification of Minimal Epitope within CFP10
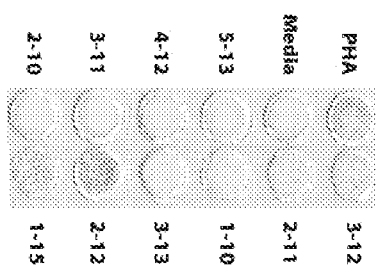
FIG. 3D  Identification of Restricting Allele
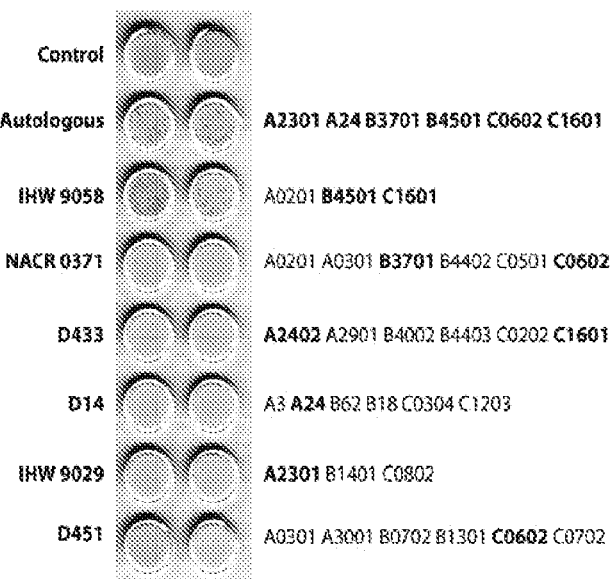

FIG. 7

SEQUENCE LISTING

```
<160> NUMBER OF SEQ ID NOS: 38

<210> SEQ ID NO 1
<211> LENGTH: 97
<212> TYPE: PRT
<213> ORGANISM: Mycobacterium tuberculosis
<220> FEATURE:
<221> NAME/KEY: MISC_FEATURE
<222> LOCATION: (2)..(2)
<223> OTHER INFORMATION: Xaa can be A or T
```

```
<220> FEATURE:
<221> NAME/KEY: MISC_FEATURE
<222> LOCATION: (58)..(58)
<223> OTHER INFORMATION: Xaa can be T or A
<220> FEATURE:
<221> NAME/KEY: MISC_FEATURE
<222> LOCATION: (59)..(59)
<223> OTHER INFORMATION: Xaa any amino acid or no amino acid

<400> SEQUENCE: 1

Met Xaa Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Xaa Xaa Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 2
<211> LENGTH: 97
<212> TYPE: PRT
<213> ORGANISM: Mycobacterium tuberculosis

<400> SEQUENCE: 2

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 3
<211> LENGTH: 98
<212> TYPE: PRT
<213> ORGANISM: Mycobacterium tuberculosis

<400> SEQUENCE: 3

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60
```

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
            85                  90                  95

Ser Ser

<210> SEQ ID NO 4
<211> LENGTH: 97
<212> TYPE: PRT
<213> ORGANISM: Mycobacterium tuberculosis

<400> SEQUENCE: 4

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Met Asn Gln Ala Phe Arg
    50                  55                  60

Asn Ile Val Asn Met Leu His Gly Val Arg Asp Gly Leu Val Arg Asp
65                  70                  75                  80

Ala Asn Asn Tyr Glu Gln Gln Glu Gln Ala Ser Gln Gln Ile Leu Ser
            85                  90                  95

Ser

<210> SEQ ID NO 5
<211> LENGTH: 98
<212> TYPE: PRT
<213> ORGANISM: Mycobacterium tuberculosis

<400> SEQUENCE: 5

Met Ala Thr Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
            85                  90                  95

Ser Ser

<210> SEQ ID NO 6
<211> LENGTH: 98
<212> TYPE: PRT
<213> ORGANISM: Mycobacterium tuberculosis

<400> SEQUENCE: 6

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met

```
                    35                  40                  45

Ala Glu Ala Thr Ser Leu Asp Thr Met Thr Gln Met Asn Gln Ala Phe
 50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser

<210> SEQ ID NO 7
<211> LENGTH: 144
<212> TYPE: PRT
<213> ORGANISM: Mycobacterium tuberculosis

<400> SEQUENCE: 7

Met Ser Tyr Met Ile Ala Thr Pro Ala Ala Leu Thr Ala Ala Ala Thr
 1               5                  10                  15

Asp Ile Asp Gly Ile Gly Ser Ala Val Ser Val Ala Asn Ala Ala Ala
                 20                  25                  30

Val Ala Ala Thr Thr Gly Val Leu Ala Ala Gly Gly Asp Glu Val Leu
                 35                  40                  45

Ala Ala Ile Ala Arg Leu Phe Asn Ala Asn Glu Glu Tyr His Ala
 50                  55                  60

Leu Ser Ala Gln Val Ala Ala Phe Gln Thr Leu Phe Val Arg Thr Leu
 65                  70                  75                  80

Thr Gly Gly Cys Gly Val Phe Arg Arg Arg Gly Arg Gln Cys Val
                 85                  90                  95

Thr Ala Ala Glu His Arg Ala Ala Gly Ala Gly Arg Arg Gln Arg Arg
                100                 105                 110

Arg Arg Ser Gly Asp Gly Gln Trp Arg Leu Arg Gln Arg His Phe
                115                 120                 125

Gly Cys Gly Gly Gln Pro Glu Phe Arg Gln His Ser Glu His Arg Arg
130                 135                 140

<210> SEQ ID NO 8
<211> LENGTH: 694
<212> TYPE: PRT
<213> ORGANISM: Mycobacterium tuberculosis

<400> SEQUENCE: 8

Val Ser Leu Val Ile Ala Thr Pro Gln Leu Leu Ala Thr Ala Ala Leu
 1               5                  10                  15

Asp Leu Ala Ser Ile Gly Ser Gln Val Ser Ala Ala Asn Ala Ala Ala
                 20                  25                  30

Ala Met Pro Thr Thr Glu Val Val Ala Ala Ala Asp Glu Val Ser
                 35                  40                  45

Ala Ala Ile Ala Gly Leu Phe Gly Ala His Ala Arg Gln Tyr Gln Ala
 50                  55                  60

Leu Ser Val Gln Val Ala Ala Phe His Glu Gln Phe Val Gln Ala Leu
 65                  70                  75                  80

Thr Ala Ala Ala Gly Arg Tyr Ala Ser Thr Glu Ala Ala Val Glu Arg
                 85                  90                  95

Ser Leu Leu Gly Ala Val Asn Ala Pro Thr Glu Ala Leu Leu Gly Arg
                100                 105                 110

Pro Leu Ile Gly Asn Gly Ala Asp Gly Thr Ala Pro Gly Gln Pro Gly
                115                 120                 125
```

```
Ala Ala Gly Gly Leu Leu Phe Gly Asn Gly Gly Asn Gly Ala Ala Gly
            130                 135                 140

Gly Phe Gly Gln Thr Gly Gly Ser Gly Gly Ala Ala Gly Leu Ile Gly
145                 150                 155                 160

Asn Gly Gly Asn Gly Gly Ala Gly Gly Thr Gly Ala Ala Gly Gly Ala
                165                 170                 175

Gly Gly Asn Gly Gly Trp Leu Trp Gly Asn Gly Gly Asn Gly Gly Val
            180                 185                 190

Gly Gly Thr Ser Val Ala Ala Gly Ile Gly Gly Ala Gly Gly Asn Gly
            195                 200                 205

Gly Asn Ala Gly Leu Phe Gly His Gly Gly Ala Gly Gly Thr Gly Gly
210                 215                 220

Ala Gly Leu Ala Gly Ala Asn Gly Val Asn Pro Thr Pro Gly Pro Ala
225                 230                 235                 240

Ala Ser Thr Gly Asp Ser Pro Ala Asp Val Ser Gly Ile Gly Asp Gln
                245                 250                 255

Thr Gly Gly Asp Gly Gly Thr Gly Gly His Gly Thr Ala Gly Thr Pro
            260                 265                 270

Thr Gly Gly Thr Gly Gly Asp Gly Ala Thr Ala Thr Ala Gly Ser Gly
            275                 280                 285

Lys Ala Thr Gly Gly Ala Gly Gly Asp Gly Gly Thr Ala Ala Ala Gly
290                 295                 300

Gly Gly Gly Gly Asn Gly Gly Asp Gly Gly Val Ala Gln Gly Asp Ile
305                 310                 315                 320

Ala Ser Ala Phe Gly Gly Asp Gly Gly Asn Gly Ser Asp Gly Val Ala
                325                 330                 335

Ala Gly Ser Gly Gly Gly Ser Gly Gly Ala Gly Gly Ala Phe Val
            340                 345                 350

His Ile Ala Thr Ala Thr Ser Thr Gly Gly Ser Gly Gly Phe Gly Gly
            355                 360                 365

Asn Gly Ala Ala Ser Ala Ala Ser Gly Ala Asp Gly Gly Ala Gly Gly
            370                 375                 380

Ala Gly Gly Asn Gly Gly Ala Gly Gly Leu Leu Phe Gly Asp Gly Gly
385                 390                 395                 400

Asn Gly Gly Ala Gly Gly Ala Gly Gly Ile Gly Gly Asp Gly Ala Thr
                405                 410                 415

Gly Gly Pro Gly Gly Ser Gly Gly Asn Ala Gly Ile Ala Arg Phe Asp
            420                 425                 430

Ser Pro Asp Pro Glu Ala Glu Pro Asp Val Val Gly Lys Gly Gly
            435                 440                 445

Asp Gly Gly Lys Gly Gly Ser Gly Leu Gly Val Gly Gly Ala Gly Gly
            450                 455                 460

Thr Gly Gly Ala Gly Gly Asn Gly Gly Ala Gly Gly Leu Leu Phe Gly
465                 470                 475                 480

Asn Gly Gly Asn Gly Gly Asn Ala Gly Ala Gly Gly Asp Gly Gly Ala
                485                 490                 495

Gly Val Ala Gly Gly Val Gly Gly Asn Gly Gly Gly Gly Thr Ala
            500                 505                 510

Thr Phe His Glu Asp Pro Val Ala Gly Val Trp Ala Val Gly Gly Val
            515                 520                 525

Gly Gly Asp Gly Gly Ser Gly Gly Ser Ser Leu Gly Val Gly Gly Val
530                 535                 540
```

Gly Gly Ala Gly Gly Val Gly Gly Lys Gly Ala Ser Gly Met Leu
545                 550                 555                 560

Ile Gly Asn Gly Gly Asn Gly Gly Ser Gly Gly Val Gly Gly Ala Gly
                565                 570                 575

Gly Val Gly Gly Ala Gly Gly Asp Gly Gly Asn Gly Gly Ser Gly Gly
                580                 585                 590

Asn Ala Ser Thr Phe Gly Asp Glu Asn Ser Ile Gly Gly Ala Gly Gly
                595                 600                 605

Thr Gly Gly Asn Gly Gly Asn Gly Ala Asn Gly Gly Asn Gly Gly Ala
610                 615                 620

Gly Gly Ile Ala Gly Ala Gly Gly Ser Gly Gly Phe Leu Ser Gly
625                 630                 635                 640

Ala Ala Gly Val Ser Gly Ala Asp Gly Ile Gly Gly Ala Gly Gly Ala
                645                 650                 655

Gly Gly Ala Gly Gly Ala Gly Ser Gly Gly Glu Ala Gly Ala Gly
                660                 665                 670

Gly Leu Thr Asn Gly Pro Gly Ser Pro Gly Val Ser Thr Glu Gly
675                 680                 685

Met Ala Gly Ala Pro Gly
    690

<210> SEQ ID NO 9
<211> LENGTH: 325
<212> TYPE: PRT
<213> ORGANISM: Mycobacterium tuberculosis

<400> SEQUENCE: 9

Met His Gln Val Asp Pro Asn Leu Thr Arg Arg Lys Gly Arg Leu Ala
1               5 10 15

Ala Leu Ala Ile Ala Ala Met Ala Ser Ala Ser Leu Val Thr Val Ala
20 25 30

Val Pro Ala Thr Ala Asn Ala Asp Pro Glu Pro Ala Pro Pro Val Pro
35 40 45

Thr Thr Ala Ala Ser Pro Pro Ser Thr Ala Ala Ala Pro Pro Ala Pro
50 55 60

Ala Thr Pro Val Ala Pro Pro Pro Pro Ala Ala Ala Asn Thr Pro Asn
65 70 75 80

Ala Gln Pro Gly Asp Pro Asn Ala Ala Pro Pro Pro Ala Asp Pro Asn
85 90 95

Ala Pro Pro Pro Pro Val Ile Ala Pro Asn Ala Pro Gln Pro Val Arg
100 105 110

Ile Asp Asn Pro Val Gly Gly Phe Ser Phe Ala Leu Pro Ala Gly Trp
115 120 125

Val Glu Ser Asp Ala Ala His Phe Asp Tyr Gly Ser Ala Leu Leu Ser
130 135 140

Lys Thr Thr Gly Asp Pro Pro Phe Pro Gly Gln Pro Pro Pro Val Ala
145 150 155 160

Asn Asp Thr Arg Ile Val Leu Gly Arg Leu Asp Gln Lys Leu Tyr Ala
165 170 175

Ser Ala Glu Ala Thr Asp Ser Lys Ala Ala Ala Arg Leu Gly Ser Asp
180 185 190

Met Gly Glu Phe Tyr Met Pro Tyr Pro Gly Thr Arg Ile Asn Gln Glu
195 200 205

Thr Val Ser Leu Asp Ala Asn Gly Val Ser Gly Ser Ala Ser Tyr Tyr
210 215 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
            275                 280                 285

Pro Pro Pro Ala Pro Ala Pro Ala Pro Ala Glu Pro Ala Pro Ala Pro
            290                 295                 300

Ala Pro Ala Gly Glu Val Ala Pro Thr Pro Thr Thr Pro Thr Pro Gln
305                 310                 315                 320

Arg Thr Leu Pro Ala
                325

<210> SEQ ID NO 10
<211> LENGTH: 582
<212> TYPE: PRT
<213> ORGANISM: Mycobacterium tuberculosis

<400> SEQUENCE: 10

Met Leu Leu Ala Leu Leu Arg Gln His Ile Arg Pro Tyr Arg Arg Leu
1               5                   10                  15

Val Ala Met Leu Met Met Leu Gln Leu Val Ser Thr Leu Ala Ser Leu
            20                  25                  30

Tyr Leu Pro Thr Val Asn Ala Ala Ile Val Asp Asp Gly Val Ala Lys
        35                  40                  45

Gly Asp Thr Ala Thr Ile Val Arg Leu Gly Ala Val Met Leu Gly Val
    50                  55                  60

Thr Gly Leu Gln Val Leu Cys Ala Ile Gly Ala Val Tyr Leu Gly Ser
65              70                  75                  80

Arg Thr Gly Ala Gly Phe Gly Arg Asp Leu Arg Ser Ala Met Phe Glu
                85                  90                  95

His Ile Ile Thr Phe Ser Glu Arg Glu Thr Ala Arg Phe Gly Ala Pro
            100                 105                 110

Thr Leu Leu Thr Arg Ser Thr Asn Asp Val Arg Gln Ile Leu Phe Leu
        115                 120                 125

Val Gln Met Thr Ala Thr Val Leu Val Thr Ala Pro Ile Met Cys Val
    130                 135                 140

Gly Gly Ile Ile Met Ala Ile His Gln Glu Ala Ala Leu Thr Trp Leu
145                 150                 155                 160

Leu Leu Val Ser Val Pro Ile Leu Ala Val Ala Asn Tyr Trp Ile Ile
                165                 170                 175

Ser His Met Leu Pro Leu Phe Arg Arg Met Gln Ser Leu Ile Asp Gly
            180                 185                 190

Ile Asn Arg Val Met Arg Asp Gln Leu Ser Gly Val Arg Val Val Arg
        195                 200                 205

Ala Phe Thr Arg Glu Gly Tyr Glu Arg Asp Lys Phe Ala Gln Ala Asn
    210                 215                 220

Thr Ala Leu Ser Asn Ala Ala Leu Ser Ala Gly Asn Trp Gln Ala Leu
225                 230                 235                 240

Met Leu Pro Val Thr Thr Leu Thr Ile Asn Ala Ser Ser Val Ala Leu
                245                 250                 255

Ile Trp Phe Gly Gly Leu Arg Ile Asp Ser Gly Gln Met Gln Val Gly

```
            260                 265                 270
Ser Leu Ile Ala Phe Leu Ser Tyr Phe Ala Gln Ile Leu Met Ala Val
        275                 280                 285

Leu Met Ala Thr Met Thr Leu Ala Val Leu Pro Arg Ala Ser Val Cys
    290                 295                 300

Ala Glu Arg Ile Thr Glu Val Leu Ser Thr Pro Ala Ala Leu Gly Asn
305                 310                 315                 320

Pro Asp Asn Pro Lys Phe Pro Thr Asp Gly Val Thr Gly Val Val Arg
                325                 330                 335

Leu Ala Gly Ala Thr Phe Thr Tyr Pro Gly Ala Asp Cys Pro Val Leu
            340                 345                 350

Gln Asp Ile Ser Leu Thr Ala Arg Pro Gly Thr Thr Ala Ile Val
        355                 360                 365

Gly Ser Thr Gly Ser Gly Lys Ser Thr Leu Val Ser Leu Ile Cys Arg
    370                 375                 380

Leu Tyr Asp Val Thr Ala Gly Ala Val Leu Val Asp Gly Ile Asp Val
385                 390                 395                 400

Arg Glu Tyr His Thr Glu Arg Leu Trp Ser Ala Ile Gly Leu Val Pro
                405                 410                 415

Gln Arg Ser Tyr Leu Phe Ser Gly Thr Val Ala Asp Asn Leu Arg Tyr
            420                 425                 430

Gly Gly Gly Pro Asp Gln Val Val Thr Glu Gln Glu Met Trp Glu Ala
        435                 440                 445

Leu Arg Val Ala Ala Ala Asp Gly Phe Val Gln Thr Asp Gly Leu Gln
    450                 455                 460

Thr Arg Val Ala Gln Gly Gly Val Asn Phe Ser Gly Gly Gln Arg Gln
465                 470                 475                 480

Arg Leu Ala Ile Ala Arg Ala Val Ile Arg Pro Ala Ile Tyr Val
                485                 490                 495

Phe Asp Asp Ala Phe Ser Ala Leu Asp Val His Thr Asp Ala Lys Val
            500                 505                 510

His Ala Ser Leu Arg Gln Val Ser Gly Asp Ala Thr Ile Ile Val Val
        515                 520                 525

Thr Gln Arg Ile Ser Asn Ala Ala Gln Ala Asp Gln Val Ile Val Val
    530                 535                 540

Asp Asn Gly Lys Ile Val Gly Thr Gly Thr His Glu Thr Leu Leu Ala
545                 550                 555                 560

Asp Cys Pro Thr Tyr Ala Glu Phe Ala Ala Ser Gln Ser Leu Ser Ala
                565                 570                 575

Thr Val Gly Gly Val Gly
            580

<210> SEQ ID NO 11
<211> LENGTH: 468
<212> TYPE: PRT
<213> ORGANISM: Mycobacterium tuberculosis

<400> SEQUENCE: 11

Met Ser Tyr Val Ile Ala Ala Pro Glu Met Leu Ala Thr Thr Ala Ala
1               5                   10                  15

Asp Val Asp Gly Ile Gly Ser Ala Ile Arg Ala Ala Ser Ala Ser Ala
            20                  25                  30

Ala Gly Pro Thr Thr Gly Leu Leu Ala Ala Ala Asp Glu Val Ser
        35                  40                  45
```

```
Ser Ala Ala Ala Ala Leu Phe Ser Glu Tyr Ala Arg Glu Cys Gln Glu
 50                  55                  60

Val Leu Lys Gln Ala Ala Ala Phe His Gly Glu Phe Thr Arg Ala Leu
 65                  70                  75                  80

Ala Ala Ala Gly Ala Ala Tyr Ala Gln Ala Glu Ala Ser Asn Thr Ala
                 85                  90                  95

Ala Met Ser Gly Thr Ala Gly Ser Ser Gly Ala Leu Gly Ser Val Gly
            100                 105                 110

Met Leu Ser Gly Asn Pro Leu Thr Ala Leu Met Met Gly Gly Thr Gly
            115                 120                 125

Glu Pro Ile Leu Ser Asp Arg Val Leu Ala Ile Ile Asp Ser Ala Tyr
130                 135                 140

Ile Arg Pro Ile Phe Gly Pro Asn Asn Pro Val Ala Gln Tyr Thr Pro
145                 150                 155                 160

Glu Gln Trp Trp Pro Phe Ile Gly Asn Leu Ser Leu Asp Gln Ser Ile
                165                 170                 175

Ala Gln Gly Val Thr Leu Leu Asn Asn Gly Ile Asn Ala Glu Leu Gln
            180                 185                 190

Asn Gly His Asp Val Val Phe Gly Tyr Ser Gln Ser Ala Ala Val
            195                 200                 205

Ala Thr Asn Glu Ile Arg Ala Leu Met Ala Leu Pro Pro Gly Gln Ala
210                 215                 220

Pro Asp Pro Ser Arg Leu Ala Phe Thr Leu Ile Gly Asn Ile Asn Asn
225                 230                 235                 240

Pro Asn Gly Gly Val Leu Glu Arg Tyr Val Gly Leu Tyr Leu Pro Phe
                245                 250                 255

Leu Asp Met Ser Phe Asn Gly Ala Thr Pro Pro Asp Ser Pro Tyr Gln
            260                 265                 270

Thr Tyr Met Tyr Thr Gly Gln Tyr Asp Gly Tyr Ala His Asn Pro Gln
            275                 280                 285

Tyr Pro Leu Asn Ile Leu Ser Asp Leu Asn Ala Phe Met Gly Ile Arg
            290                 295                 300

Trp Val His Asn Ala Tyr Pro Phe Thr Ala Ala Glu Val Ala Asn Ala
305                 310                 315                 320

Val Pro Leu Pro Thr Ser Pro Gly Tyr Thr Gly Asn Thr His Tyr Tyr
                325                 330                 335

Met Phe Leu Thr Gln Asp Leu Pro Leu Leu Gln Pro Ile Arg Ala Ile
            340                 345                 350

Pro Phe Val Gly Thr Pro Ile Ala Glu Leu Ile Gln Pro Asp Leu Arg
            355                 360                 365

Val Leu Val Asp Leu Gly Tyr Gly Tyr Gly Tyr Ala Asp Val Pro Thr
370                 375                 380

Pro Ala Ser Leu Phe Ala Pro Ile Asn Pro Ile Ala Val Ala Ser Ala
385                 390                 395                 400

Leu Ala Thr Gly Thr Val Gln Gly Pro Gln Ala Ala Leu Val Ser Ile
                405                 410                 415

Gly Leu Leu Pro Gln Ser Ala Leu Pro Asn Thr Tyr Pro Tyr Leu Pro
            420                 425                 430

Ser Ala Asn Pro Gly Leu Met Phe Asn Phe Gly Gln Ser Ser Val Thr
            435                 440                 445

Glu Leu Ser Val Leu Ser Gly Ala Leu Gly Ser Val Ala Arg Leu Ile
450                 455                 460

Pro Pro Ile Ala
```

465

<210> SEQ ID NO 12
<211> LENGTH: 3716
<212> TYPE: PRT
<213> ORGANISM: Mycobacterium tuberculosis

<400> SEQUENCE: 12

```
Met Glu Phe Pro Val Leu Pro Pro Glu Ile Asn Ser Val Leu Met Tyr
1               5                   10                  15

Ser Gly Ala Gly Ser Ser Pro Leu Leu Ala Ala Ala Ala Ala Trp Asp
            20                  25                  30

Gly Leu Ala Glu Glu Leu Gly Ser Ala Ala Val Ser Phe Gly Gln Val
        35                  40                  45

Thr Ser Gly Leu Thr Ala Gly Val Trp Gln Gly Ala Ala Ala Ala Ala
    50                  55                  60

Met Ala Ala Ala Ala Pro Tyr Ala Gly Trp Leu Gly Ser Val Ala
65                  70                  75                  80

Ala Ala Ala Glu Ala Val Ala Gly Gln Ala Arg Val Val Val Gly Val
                85                  90                  95

Phe Glu Ala Ala Leu Ala Ala Thr Val Asp Pro Ala Leu Val Ala Ala
            100                 105                 110

Asn Arg Ala Arg Leu Val Ala Leu Ala Val Ser Asn Leu Leu Gly Gln
        115                 120                 125

Asn Thr Pro Ala Ile Ala Ala Glu Ala Glu Tyr Glu Leu Met Trp
    130                 135                 140

Ala Ala Asp Val Ala Ala Met Ala Gly Tyr His Ser Gly Ala Ser Ala
145                 150                 155                 160

Ala Ala Ala Ala Leu Pro Ala Phe Ser Pro Pro Ala Gln Ala Leu Gly
                165                 170                 175

Gly Gly Val Gly Ala Phe Leu Thr Ala Leu Phe Ala Ser Pro Ala Lys
            180                 185                 190

Ala Leu Ser Leu Asn Ala Gly Leu Gly Asn Val Gly Asn Tyr Asn Val
        195                 200                 205

Gly Leu Gly Asn Val Gly Val Phe Asn Leu Gly Ala Gly Asn Val Gly
    210                 215                 220

Gly Gln Asn Leu Gly Phe Gly Asn Ala Gly Thr Asn Val Gly Phe
225                 230                 235                 240

Gly Asn Leu Gly Asn Gly Asn Val Gly Phe Gly Asn Ser Gly Leu Gly
                245                 250                 255

Ala Gly Leu Ala Gly Leu Gly Asn Ile Gly Leu Gly Asn Ala Gly Ser
            260                 265                 270

Ser Asn Tyr Gly Phe Ala Asn Leu Gly Val Gly Asn Ile Gly Phe Gly
        275                 280                 285

Asn Thr Gly Thr Asn Asn Val Gly Val Gly Leu Thr Gly Asn His Leu
    290                 295                 300

Thr Gly Ile Gly Gly Leu Asn Ser Gly Thr Gly Asn Ile Gly Leu Phe
305                 310                 315                 320

Asn Ser Gly Thr Gly Asn Val Gly Phe Phe Asn Ser Gly Thr Gly Asn
                325                 330                 335

Phe Gly Val Phe Asn Ser Gly Asn Tyr Asn Thr Gly Val Gly Asn Ala
            340                 345                 350

Gly Thr Ala Ser Thr Gly Leu Phe Asn Ala Gly Asn Phe Asn Thr Gly
        355                 360                 365
```

```
Val Val Asn Val Gly Ser Tyr Asn Thr Gly Ser Phe Asn Ala Gly Asp
370                 375                 380

Thr Asn Thr Gly Gly Phe Asn Pro Gly Val Asn Thr Gly Trp Leu
385                 390                 395                 400

Asn Thr Gly Asn Thr Asn Thr Gly Ile Ala Asn Ser Gly Asn Val Asn
            405                 410                 415

Thr Gly Ala Phe Ile Ser Gly Asn Phe Asn Asn Gly Val Leu Trp Val
            420                 425                 430

Gly Asp Tyr Gln Gly Leu Phe Gly Val Ser Ala Gly Ser Ser Ile Pro
            435                 440                 445

Ala Ile Pro Ile Gly Leu Val Leu Asn Gly Asp Ile Gly Pro Ile Thr
450                 455                 460

Ile Gln Pro Ile Pro Ile Leu Pro Thr Ile Pro Leu Ser Ile His Gln
465                 470                 475                 480

Thr Val Asn Leu Gly Pro Leu Val Val Pro Asp Ile Val Ile Pro Ala
            485                 490                 495

Phe Gly Gly Gly Ile Gly Ile Pro Ile Asn Ile Gly Pro Leu Thr Ile
            500                 505                 510

Thr Pro Ile Thr Leu Phe Ala Gln Gln Thr Phe Val Asn Gln Leu Pro
            515                 520                 525

Phe Pro Thr Phe Ser Leu Gly Lys Ile Thr Ile Pro Gln Ile Gln Thr
530                 535                 540

Phe Asp Ser Asn Gly Gln Leu Val Ser Phe Ile Gly Pro Ile Val Ile
545                 550                 555                 560

Asp Thr Thr Ile Pro Gly Pro Thr Asn Pro Gln Ile Asp Leu Thr Ile
            565                 570                 575

Arg Trp Asp Thr Pro Ile Thr Leu Phe Pro Asn Gly Ile Ser Ala
            580                 585                 590

Pro Asp Asn Pro Leu Gly Leu Leu Val Ser Val Ser Ile Ser Asn Pro
            595                 600                 605

Gly Phe Thr Ile Pro Gly Phe Ser Val Pro Ala Gln Pro Leu Pro Leu
            610                 615                 620

Ser Ile Asp Ile Glu Gly Gln Ile Asp Gly Phe Ser Thr Pro Pro Ile
625                 630                 635                 640

Thr Ile Asp Arg Ile Pro Leu Thr Val Gly Gly Val Thr Ile Gly
            645                 650                 655

Pro Ile Thr Ile Gln Gly Leu His Ile Pro Ala Ala Pro Gly Val Gly
            660                 665                 670

Asn Thr Thr Ala Pro Ser Ser Gly Phe Phe Asn Ser Gly Ala Gly
            675                 680                 685

Gly Val Ser Gly Phe Gly Asn Val Gly Ala Gly Ser Ser Gly Trp Trp
690                 695                 700

Asn Gln Ala Pro Ser Ala Leu Leu Gly Ala Gly Ser Gly Val Gly Asn
705                 710                 715                 720

Val Gly Thr Leu Gly Ser Gly Val Leu Asn Leu Gly Ser Gly Ile Ser
            725                 730                 735

Gly Phe Tyr Asn Thr Ser Val Leu Pro Phe Gly Thr Pro Ala Ala Val
            740                 745                 750

Ser Gly Ile Gly Asn Leu Gly Gln Gln Leu Ser Gly Val Ser Ala Ala
            755                 760                 765

Gly Thr Thr Leu Arg Ser Met Leu Ala Gly Asn Leu Gly Leu Ala Asn
770                 775                 780

Val Gly Asn Phe Asn Thr Gly Phe Gly Asn Val Gly Asp Val Asn Leu
```

```
            785                 790                 795                 800
Gly Ala Ala Asn Ile Gly Gly His Asn Leu Gly Leu Gly Asn Val Gly
                805                 810                 815
Asp Gly Asn Leu Gly Leu Gly Asn Ile Gly His Gly Asn Leu Gly Phe
                820                 825                 830
Ala Asn Leu Gly Leu Thr Ala Gly Ala Ala Gly Val Gly Asn Val Gly
                835                 840                 845
Phe Gly Asn Ala Gly Ile Asn Asn Tyr Gly Leu Ala Asn Met Gly Val
                850                 855                 860
Gly Asn Ile Gly Phe Ala Asn Thr Gly Thr Gly Asn Ile Gly Ile Gly
865                 870                 875                 880
Leu Val Gly Asp His Arg Thr Gly Ile Gly Gly Leu Asn Ser Gly Ile
                885                 890                 895
Gly Asn Ile Gly Leu Phe Asn Ser Gly Thr Gly Asn Val Gly Phe Phe
                900                 905                 910
Asn Ser Gly Thr Gly Asn Phe Gly Ile Gly Asn Ser Gly Arg Phe Asn
                915                 920                 925
Thr Gly Ile Gly Asn Ser Gly Thr Ala Ser Thr Gly Leu Phe Asn Ala
    930                 935                 940
Gly Ser Phe Ser Thr Gly Ile Ala Asn Thr Gly Asp Tyr Asn Thr Gly
945                 950                 955                 960
Ser Phe Asn Ala Gly Asp Thr Asn Thr Gly Gly Phe Asn Pro Gly Gly
                965                 970                 975
Ile Asn Thr Gly Trp Phe Asn Thr Gly His Ala Asn Thr Gly Leu Ala
                980                 985                 990
Asn Ala Gly Thr Phe Gly Thr Gly Ala Phe Met Thr Gly Asp Tyr Ser
                995                 1000                1005
Asn Gly Leu Leu Trp Arg Gly Gly Tyr Glu Gly Leu Val Gly Val
    1010                1015                1020
Arg Val Gly Pro Thr Ile Ser Gln Phe Pro Val Thr Val His Ala
    1025                1030                1035
Ile Gly Gly Val Gly Pro Leu His Val Ala Pro Val Pro Val Pro
    1040                1045                1050
Ala Val His Val Glu Ile Thr Asp Ala Thr Val Gly Leu Gly Pro
    1055                1060                1065
Phe Thr Val Pro Pro Ile Ser Ile Pro Ser Leu Pro Ile Ala Ser
    1070                1075                1080
Ile Thr Gly Ser Val Asp Leu Ala Ala Asn Thr Ile Ser Pro Ile
    1085                1090                1095
Arg Ala Leu Asp Pro Leu Ala Gly Ser Ile Gly Leu Phe Leu Glu
    1100                1105                1110
Pro Phe Arg Leu Ser Asp Pro Phe Ile Thr Ile Asp Ala Phe Gln
    1115                1120                1125
Val Val Ala Gly Val Leu Phe Leu Glu Asn Ile Ile Val Pro Gly
    1130                1135                1140
Leu Thr Val Ser Gly Gln Ile Leu Val Thr Pro Thr Pro Ile Pro
    1145                1150                1155
Leu Thr Leu Asn Leu Asp Thr Thr Pro Trp Thr Leu Phe Pro Asn
    1160                1165                1170
Gly Phe Thr Ile Pro Ala Gln Thr Pro Val Thr Val Gly Met Glu
    1175                1180                1185
Val Ala Asn Asp Gly Phe Thr Phe Phe Pro Gly Gly Leu Thr Phe
    1190                1195                1200
```

-continued

```
Pro Arg Ala Ser Ala Gly Val Thr Gly Leu Ser Val Gly Leu Asp
    1205                1210                1215

Ala Phe Thr Leu Leu Pro Asp Gly Phe Thr Leu Asp Thr Val Pro
    1220                1225                1230

Ala Thr Phe Asp Gly Thr Ile Leu Ile Gly Asp Ile Pro Ile Pro
    1235                1240                1245

Ile Ile Asp Val Pro Ala Val Pro Gly Phe Gly Asn Thr Thr Thr
    1250                1255                1260

Ala Pro Ser Ser Gly Phe Phe Asn Thr Gly Gly Gly Gly Ser
    1265                1270                1275

Gly Phe Ala Asn Val Gly Ala Gly Thr Ser Gly Trp Trp Asn Gln
    1280                1285                1290

Gly His Asp Val Leu Ala Gly Ala Gly Ser Gly Val Ala Asn Ala
    1295                1300                1305

Gly Thr Leu Ser Ser Gly Val Leu Asn Val Gly Ser Gly Ile Ser
    1310                1315                1320

Gly Trp Tyr Asn Thr Ser Thr Leu Gly Ala Gly Thr Pro Ala Val
    1325                1330                1335

Val Ser Gly Ile Gly Asn Leu Gly Gln Gln Leu Ser Gly Phe Leu
    1340                1345                1350

Ala Asn Gly Thr Val Leu Asn Arg Ser Pro Ile Val Asn Ile Gly
    1355                1360                1365

Trp Ala Asp Val Gly Ala Phe Asn Thr Gly Leu Gly Asn Val Gly
    1370                1375                1380

Asp Leu Asn Trp Gly Ala Ala Asn Ile Gly Ala Gln Asn Leu Gly
    1385                1390                1395

Leu Gly Asn Leu Gly Ser Gly Asn Val Gly Phe Gly Asn Ile Gly
    1400                1405                1410

Ala Gly Asn Val Gly Phe Ala Asn Ser Gly Pro Ala Val Gly Leu
    1415                1420                1425

Ala Gly Leu Gly Asn Val Gly Leu Ser Asn Ala Gly Ser Asn Asn
    1430                1435                1440

Trp Gly Leu Ala Asn Leu Gly Val Gly Asn Ile Gly Leu Ala Asn
    1445                1450                1455

Thr Gly Thr Gly Asn Ile Gly Ile Gly Leu Val Gly Asp Tyr Gln
    1460                1465                1470

Thr Gly Ile Gly Gly Leu Asn Ser Gly Ser Gly Asn Ile Gly Leu
    1475                1480                1485

Phe Asn Ser Gly Thr Gly Asn Val Gly Phe Phe Asn Thr Gly Thr
    1490                1495                1500

Gly Asn Phe Gly Leu Phe Asn Ser Gly Ser Phe Asn Thr Gly Ile
    1505                1510                1515

Gly Asn Ser Gly Thr Gly Ser Thr Gly Leu Phe Asn Ala Gly Asn
    1520                1525                1530

Phe Asn Thr Gly Ile Ala Asn Pro Gly Ser Tyr Asn Thr Gly Ser
    1535                1540                1545

Phe Asn Val Gly Asp Thr Asn Thr Gly Gly Phe Asn Pro Gly Asp
    1550                1555                1560

Ile Asn Thr Gly Trp Phe Asn Thr Gly Ile Met Asn Thr Gly Thr
    1565                1570                1575

Arg Asn Thr Gly Ala Leu Met Ser Gly Thr Asp Ser Asn Gly Met
    1580                1585                1590
```

```
Leu Trp Arg Gly Asp His Glu Gly Leu Phe Gly Leu Ser Tyr Gly
1595                1600                1605

Ile Thr Ile Pro Gln Phe Pro Ile Arg Ile Thr Thr Thr Gly Gly
1610                1615                1620

Ile Gly Pro Ile Val Ile Pro Asp Thr Thr Ile Leu Pro Pro Leu
1625                1630                1635

His Leu Gln Ile Thr Gly Asp Ala Asp Tyr Ser Phe Thr Val Pro
1640                1645                1650

Asp Ile Pro Ile Pro Ala Ile His Ile Gly Ile Asn Gly Val Val
1655                1660                1665

Thr Val Gly Phe Thr Ala Pro Glu Ala Thr Leu Leu Ser Ala Leu
1670                1675                1680

Lys Asn Asn Gly Ser Phe Ile Ser Phe Gly Pro Ile Thr Leu Ser
1685                1690                1695

Asn Ile Asp Ile Pro Pro Met Asp Phe Thr Leu Gly Leu Pro Val
1700                1705                1710

Leu Gly Pro Ile Thr Gly Gln Leu Gly Pro Ile His Leu Glu Pro
1715                1720                1725

Ile Val Val Ala Gly Ile Gly Val Pro Leu Glu Ile Glu Pro Ile
1730                1735                1740

Pro Leu Asp Ala Ile Ser Leu Ser Glu Ser Ile Pro Ile Arg Ile
1745                1750                1755

Pro Val Asp Ile Pro Ala Ser Val Ile Asp Gly Ile Ser Met Ser
1760                1765                1770

Glu Val Val Pro Ile Asp Ala Ser Val Asp Ile Pro Ala Val Thr
1775                1780                1785

Ile Thr Gly Thr Thr Ile Ser Ala Ile Pro Leu Gly Phe Asp Ile
1790                1795                1800

Arg Thr Ser Ala Gly Pro Leu Asn Ile Pro Ile Ile Asp Ile Pro
1805                1810                1815

Ala Ala Pro Gly Phe Gly Asn Ser Thr Gln Met Pro Ser Ser Gly
1820                1825                1830

Phe Phe Asn Thr Gly Ala Gly Gly Gly Ser Gly Ile Gly Asn Leu
1835                1840                1845

Gly Ala Gly Val Ser Gly Leu Leu Asn Gln Ala Gly Ala Gly Ser
1850                1855                1860

Leu Val Gly Thr Leu Ser Gly Leu Gly Asn Ala Gly Thr Leu Ala
1865                1870                1875

Ser Gly Val Leu Asn Ser Gly Thr Ala Ile Ser Gly Leu Phe Asn
1880                1885                1890

Val Ser Thr Leu Asp Ala Thr Thr Pro Ala Val Ile Ser Gly Phe
1895                1900                1905

Ser Asn Leu Gly Asp His Met Ser Gly Val Ser Ile Asp Gly Leu
1910                1915                1920

Ile Ala Ile Leu Thr Phe Pro Pro Ala Glu Ser Val Phe Asp Gln
1925                1930                1935

Ile Ile Asp Ala Ala Ile Ala Glu Leu Gln His Leu Asp Ile Gly
1940                1945                1950

Asn Ala Leu Ala Leu Gly Asn Val Gly Gly Val Asn Leu Gly Leu
1955                1960                1965

Ala Asn Val Gly Glu Phe Asn Leu Gly Ala Gly Asn Val Gly Asn
1970                1975                1980

Ile Asn Val Gly Ala Gly Asn Leu Gly Gly Ser Asn Leu Gly Leu
```

-continued

```
            1985                1990                1995
Gly Asn Val Gly Thr Gly Asn Leu Gly Phe Gly Asn Ile Gly Ala
    2000                2005                2010
Gly Asn Phe Gly Phe Gly Asn Ala Gly Leu Thr Ala Gly Ala Gly
    2015                2020                2025
Gly Leu Gly Asn Val Gly Leu Gly Asn Ala Gly Ser Gly Ser Trp
    2030                2035                2040
Gly Leu Ala Asn Val Gly Val Gly Asn Ile Gly Leu Ala Asn Thr
    2045                2050                2055
Gly Thr Gly Asn Ile Gly Ile Gly Leu Thr Gly Asp Tyr Arg Thr
    2060                2065                2070
Gly Ile Gly Gly Leu Asn Ser Gly Thr Gly Asn Leu Gly Leu Phe
    2075                2080                2085
Asn Ser Gly Thr Gly Asn Ile Gly Phe Phe Asn Thr Gly Thr Gly
    2090                2095                2100
Asn Phe Gly Leu Phe Asn Ser Gly Ser Tyr Ser Thr Gly Val Gly
    2105                2110                2115
Asn Ala Gly Thr Ala Ser Thr Gly Leu Phe Asn Ala Gly Asn Phe
    2120                2125                2130
Asn Thr Gly Leu Ala Asn Ala Gly Ser Tyr Asn Thr Gly Ser Leu
    2135                2140                2145
Asn Val Gly Ser Phe Asn Thr Gly Gly Val Asn Pro Gly Thr Val
    2150                2155                2160
Asn Thr Gly Trp Phe Asn Thr Gly His Thr Asn Thr Gly Leu Phe
    2165                2170                2175
Asn Thr Gly Asn Val Asn Thr Gly Ala Phe Asn Ser Gly Ser Phe
    2180                2185                2190
Asn Asn Gly Ala Leu Trp Thr Gly Asp Tyr His Gly Leu Val Gly
    2195                2200                2205
Phe Ser Phe Ser Ile Asp Ile Ala Gly Ser Thr Leu Leu Asp Leu
    2210                2215                2220
Asn Glu Thr Leu Asn Leu Gly Pro Ile His Ile Glu Gln Ile Asp
    2225                2230                2235
Ile Pro Gly Met Ser Leu Phe Asp Val His Glu Ile Val Glu Ile
    2240                2245                2250
Gly Pro Phe Thr Ile Pro Gln Val Asp Val Pro Ala Ile Pro Leu
    2255                2260                2265
Glu Ile His Glu Ser Ile His Met Asp Pro Ile Val Leu Val Pro
    2270                2275                2280
Ala Thr Thr Ile Pro Ala Gln Thr Arg Thr Ile Pro Leu Asp Ile
    2285                2290                2295
Pro Ala Ser Pro Gly Ser Thr Met Thr Leu Pro Leu Ile Ser Met
    2300                2305                2310
Arg Phe Glu Gly Glu Asp Trp Ile Leu Gly Ser Thr Ala Ala Ile
    2315                2320                2325
Pro Asn Phe Gly Asp Pro Phe Pro Ala Pro Thr Gln Gly Ile Thr
    2330                2335                2340
Ile His Thr Gly Pro Gly Pro Gly Thr Thr Gly Glu Leu Lys Ile
    2345                2350                2355
Ser Ile Pro Gly Phe Glu Ile Pro Gln Ile Ala Thr Thr Arg Phe
    2360                2365                2370
Leu Leu Asp Val Asn Ile Ser Gly Gly Leu Pro Ala Phe Thr Leu
    2375                2380                2385
```

-continued

Phe Ala Gly Gly Leu Thr Ile Pro Thr Asn Ala Ile Pro Leu Thr
2390                2395                2400

Ile Asp Ala Ser Gly Ala Leu Asp Pro Ile Thr Ile Phe Pro Gly
2405                2410                2415

Gly Tyr Thr Ile Asp Pro Leu Pro Leu His Leu Ala Leu Asn Leu
2420                2425                2430

Thr Val Pro Asp Ser Ser Ile Pro Ile Ile Asp Val Pro Pro Thr
2435                2440                2445

Pro Gly Phe Gly Asn Thr Thr Ala Thr Pro Ser Ser Gly Phe Phe
2450                2455                2460

Asn Ser Gly Ala Gly Gly Val Ser Gly Phe Gly Asn Val Gly Ser
2465                2470                2475

Asn Leu Ser Gly Trp Trp Asn Gln Ala Ala Ser Ala Leu Ala Gly
2480                2485                2490

Ser Gly Ser Gly Val Leu Asn Val Gly Thr Leu Gly Ser Gly Val
2495                2500                2505

Leu Asn Val Gly Ser Gly Val Ser Gly Ile Tyr Asn Thr Ser Val
2510                2515                2520

Leu Pro Leu Gly Thr Pro Ala Val Leu Ser Gly Leu Gly Asn Val
2525                2530                2535

Gly His Gln Leu Ser Gly Val Ser Ala Ala Gly Thr Ala Leu Asn
2540                2545                2550

Gln Ile Pro Ile Leu Asn Ile Gly Leu Ala Asp Val Gly Asn Phe
2555                2560                2565

Asn Val Gly Phe Gly Asn Val Gly Asp Val Asn Leu Gly Ala Ala
2570                2575                2580

Asn Leu Gly Ala Gln Asn Leu Gly Leu Gly Asn Val Gly Thr Gly
2585                2590                2595

Asn Leu Gly Phe Ala Asn Val Gly His Gly Asn Ile Gly Phe Gly
2600                2605                2610

Asn Ser Gly Leu Thr Ala Gly Ala Ala Gly Leu Gly Asn Thr Gly
2615                2620                2625

Phe Gly Asn Ala Gly Ser Ala Asn Tyr Gly Phe Ala Asn Gln Gly
2630                2635                2640

Val Arg Asn Ile Gly Leu Ala Asn Thr Gly Thr Gly Asn Ile Gly
2645                2650                2655

Ile Gly Leu Val Gly Asp Asn Leu Thr Gly Ile Gly Gly Leu Asn
2660                2665                2670

Ser Gly Ala Gly Asn Ile Gly Leu Phe Asn Ser Gly Thr Gly Asn
2675                2680                2685

Ile Gly Phe Phe Asn Ser Gly Thr Gly Asn Phe Gly Ile Gly Asn
2690                2695                2700

Ser Gly Ser Phe Asn Thr Gly Ile Gly Asn Ser Gly Thr Gly Ser
2705                2710                2715

Thr Gly Leu Phe Asn Ala Gly Ser Phe Asn Thr Gly Val Ala Asn
2720                2725                2730

Ala Gly Ser Tyr Asn Thr Gly Ser Phe Asn Ala Gly Asp Thr Asn
2735                2740                2745

Thr Gly Gly Phe Asn Pro Gly Thr Ile Asn Thr Gly Trp Phe Asn
2750                2755                2760

Thr Gly His Thr Asn Thr Gly Ile Ala Asn Ser Gly Asn Val Gly
2765                2770                2775

-continued

Thr Gly Ala Phe Met Ser Gly Asn Phe Ser Asn Gly Leu Leu Trp
2780            2785             2790

Arg Gly Asp His Glu Gly Leu Phe Ser Leu Phe Tyr Ser Leu Asp
2795            2800             2805

Val Pro Arg Ile Thr Ile Val Asp Ala His Leu Asp Gly Gly Phe
2810            2815             2820

Gly Pro Val Val Leu Pro Pro Ile Pro Val Pro Ala Val Asn Ala
2825            2830             2835

His Leu Thr Gly Asn Val Ala Met Gly Ala Phe Thr Ile Pro Gln
2840            2845             2850

Ile Asp Ile Pro Ala Leu Thr Pro Asn Ile Thr Gly Ser Ala Ala
2855            2860             2865

Phe Arg Ile Val Val Gly Ser Val Arg Ile Pro Val Ser Val
2870            2875             2880

Ile Val Glu Gln Ile Ile Asn Ala Ser Val Gly Ala Glu Met Arg
2885            2890             2895

Ile Asp Pro Phe Glu Met Trp Thr Gln Gly Thr Asn Gly Leu Gly
2900            2905             2910

Ile Thr Phe Tyr Ser Phe Gly Ser Ala Asp Gly Ser Pro Tyr Ala
2915            2920             2925

Thr Gly Pro Leu Val Phe Gly Ala Gly Thr Ser Asp Gly Ser His
2930            2935             2940

Leu Thr Ile Ser Ala Ser Ser Gly Ala Phe Thr Thr Pro Gln Leu
2945            2950             2955

Glu Thr Gly Pro Ile Thr Leu Gly Phe Gln Val Pro Gly Ser Val
2960            2965             2970

Asn Ala Ile Thr Leu Phe Pro Gly Gly Leu Thr Phe Pro Ala Thr
2975            2980             2985

Ser Leu Leu Asn Leu Asp Val Thr Ala Gly Ala Gly Gly Val Asp
2990            2995             3000

Ile Pro Ala Ile Thr Trp Pro Glu Ile Ala Ala Ser Ala Asp Gly
3005            3010             3015

Ser Val Tyr Val Leu Ala Ser Ser Ile Pro Leu Ile Asn Ile Pro
3020            3025             3030

Pro Thr Pro Gly Ile Gly Asn Ser Thr Ile Thr Pro Ser Ser Gly
3035            3040             3045

Phe Phe Asn Ala Gly Ala Gly Gly Ser Gly Phe Gly Asn Phe
3050            3055             3060

Gly Ala Gly Thr Ser Gly Trp Trp Asn Gln Ala His Thr Ala Leu
3065            3070             3075

Ala Gly Ala Gly Ser Gly Phe Ala Asn Val Gly Thr Leu His Ser
3080            3085             3090

Gly Val Leu Asn Leu Gly Ser Gly Val Ser Gly Ile Tyr Asn Thr
3095            3100             3105

Ser Thr Leu Gly Val Gly Thr Pro Ala Leu Val Ser Gly Leu Gly
3110            3115             3120

Asn Val Gly His Gln Leu Ser Gly Leu Leu Ser Gly Gly Ser Ala
3125            3130             3135

Val Asn Pro Val Thr Val Leu Asn Ile Gly Leu Ala Asn Val Gly
3140            3145             3150

Ser His Asn Ala Gly Phe Gly Asn Val Gly Glu Val Asn Leu Gly
3155            3160             3165

Ala Ala Asn Leu Gly Ala His Asn Leu Gly Phe Gly Asn Ile Gly

```
            3170                3175                3180

Ala Gly Asn Leu Gly Phe Gly Asn Ile Gly His Gly Asn Val Gly
        3185                3190                3195

Val Gly Asn Ser Gly Leu Thr Ala Gly Val Pro Gly Leu Gly Asn
        3200                3205                3210

Val Gly Leu Gly Asn Ala Gly Gly Asn Asn Trp Gly Leu Ala Asn
        3215                3220                3225

Val Gly Val Gly Asn Ile Gly Leu Ala Asn Thr Gly Thr Gly Asn
        3230                3235                3240

Ile Gly Ile Gly Leu Thr Gly Asp Tyr Gln Thr Gly Ile Gly Gly
        3245                3250                3255

Leu Asn Ser Gly Ala Gly Asn Leu Gly Leu Phe Asn Ser Gly Ala
        3260                3265                3270

Gly Asn Val Gly Phe Phe Asn Thr Gly Thr Gly Asn Phe Gly Leu
        3275                3280                3285

Phe Asn Ser Gly Ser Phe Asn Thr Gly Val Gly Asn Ser Gly Thr
        3290                3295                3300

Gly Ser Thr Gly Leu Phe Asn Ala Gly Ser Phe Asn Thr Gly Val
        3305                3310                3315

Ala Asn Ala Gly Ser Tyr Asn Thr Gly Ser Phe Asn Val Gly Asp
        3320                3325                3330

Thr Asn Thr Gly Gly Phe Asn Pro Gly Ser Ile Asn Thr Gly Trp
        3335                3340                3345

Leu Asn Ala Gly Asn Ala Asn Thr Gly Val Ala Asn Ala Gly Asn
        3350                3355                3360

Val Asn Thr Gly Ala Phe Val Thr Gly Asn Phe Ser Asn Gly Ile
        3365                3370                3375

Leu Trp Arg Gly Asp Tyr Gln Gly Leu Ala Gly Phe Ala Val Gly
        3380                3385                3390

Tyr Thr Leu Pro Leu Phe Pro Ala Val Gly Ala Asp Val Ser Gly
        3395                3400                3405

Gly Ile Gly Pro Ile Thr Val Leu Pro Pro Ile His Ile Pro Pro
        3410                3415                3420

Ile Pro Val Gly Phe Ala Ala Val Gly Gly Ile Gly Pro Ile Ala
        3425                3430                3435

Ile Pro Asp Ile Ser Val Pro Ser Ile His Leu Gly Leu Asp Pro
        3440                3445                3450

Ala Val His Val Gly Ser Ile Thr Val Asn Pro Ile Thr Val Arg
        3455                3460                3465

Thr Pro Pro Val Leu Val Ser Tyr Ser Gln Gly Ala Val Thr Ser
        3470                3475                3480

Thr Ser Gly Pro Thr Ser Glu Ile Trp Val Lys Pro Ser Phe Phe
        3485                3490                3495

Pro Gly Ile Arg Ile Ala Pro Ser Ser Gly Gly Ala Thr Ser
        3500                3505                3510

Thr Gln Gly Ala Tyr Phe Val Gly Pro Ile Ser Ile Pro Ser Gly
        3515                3520                3525

Thr Val Thr Phe Pro Gly Phe Thr Ile Pro Leu Asp Pro Ile Asp
        3530                3535                3540

Ile Gly Leu Pro Val Ser Leu Thr Ile Pro Gly Phe Thr Ile Pro
        3545                3550                3555

Gly Gly Thr Leu Ile Pro Thr Leu Pro Leu Gly Leu Ala Leu Ser
        3560                3565                3570
```

Asn Gly Ile Pro Pro Val Asp Ile Pro Ala Ile Val Leu Asp Arg
3575                3580                3585

Ile Leu Leu Asp Leu His Ala Asp Thr Thr Ile Gly Pro Ile Asn
    3590                3595                3600

Val Pro Ile Ala Gly Phe Gly Gly Ala Pro Gly Phe Gly Asn Ser
3605                3610                3615

Thr Thr Leu Pro Ser Ser Gly Phe Phe Asn Thr Gly Ala Gly Gly
3620                3625                3630

Gly Ser Gly Phe Ser Asn Thr Gly Ala Gly Met Ser Gly Leu Leu
3635                3640                3645

Asn Ala Met Ser Asp Pro Leu Leu Gly Ser Ala Ser Gly Phe Ala
3650                3655                3660

Asn Phe Gly Thr Gln Leu Ser Gly Ile Leu Asn Arg Gly Ala Gly
3665                3670                3675

Ile Ser Gly Val Tyr Asn Thr Gly Ala Leu Gly Val Val Thr Ala
3680                3685                3690

Ala Val Val Ser Gly Phe Gly Asn Val Gly Gln Gln Leu Ser Gly
3695                3700                3705

Leu Leu Phe Thr Gly Val Gly Pro
3710                3715

<210> SEQ ID NO 13
<211> LENGTH: 11
<212> TYPE: PRT
<213> ORGANISM: Mycobacterium tuberculosis

<400> SEQUENCE: 13

Gln Thr Val Glu Asp Glu Ala Arg Arg Met Trp
1               5                   10

<210> SEQ ID NO 14
<211> LENGTH: 9
<212> TYPE: PRT
<213> ORGANISM: Mycobacterium tuberculosis

<400> SEQUENCE: 14

Val Ser Ala Ala Ile Ala Gly Leu Phe
1               5

<210> SEQ ID NO 15
<211> LENGTH: 297
<212> TYPE: DNA
<213> ORGANISM: Mycobacterium tuberculosis

<400> SEQUENCE: 15
atggcctcgc gttttatgac ggatccgcac gcgatgcggg acatggcggg ccgttttgag     60
gtgcacgccc agacggtgga ggacgaggct cgccggatgt gggcgtccgc gcaaaacatc    120
tcgggcgcgg gctggagtgg catggccgag gcgacctcgc tagacaccat gacccagatg    180
aatcaggcgt tcgcaacat cgtgaacatg ctgcacgggg tgcgtgacgg gctggttcgc    240
gacgccaaca actacgaaca gcaagagcag gcctcccagc agatcctcag cagctga      297

<210> SEQ ID NO 16
<211> LENGTH: 297
<212> TYPE: DNA
<213> ORGANISM: Mycobacterium tuberculosis

<400> SEQUENCE: 16

```
atggcctcac gttttatgac ggatccgcac gcgatgcggg acatggcggg ccgttttgag    60
gtgcacgccc agacggtgga ggacgaggct cgccggatgt gggcgtccgc gcaaaacatt   120
tccggtgcgg gctggagtgg catggccgag gcgacctcgc tagacaccat ggcccagatg   180
aatcaggcgt ttcgcaacat cgtgaacatg ctgcacgggg tgcgtgacgg gctggttcgc   240
gacgccaaca actacgagca gcaagagcag gcctcccagc agatcctcag cagctaa     297
```

<210> SEQ ID NO 17
<211> LENGTH: 297
<212> TYPE: DNA
<213> ORGANISM: Mycobacterium tuberculosis

<400> SEQUENCE: 17

```
atggcctcac gttttatgac ggatccgcat gcgatgcggg acatggcggg ccgttttgag    60
gtgcacgccc agacggtgga ggacgaggct cgccggatgt gggcgtccgc gcaaaacatt   120
tccggtgcgg gctggagtgg catggccgag gcgacctcgc tagacaccat gacctagatg   180
aatcaggcgt ttcgcaacat cgtgaacatg ctgcacgggg tgcgtgacgg gctggttcgc   240
gacgccaaca actacgaaca gcaagagcag gcctcccagc agatcctgag cagctag     297
```

<210> SEQ ID NO 18
<211> LENGTH: 297
<212> TYPE: DNA
<213> ORGANISM: Mycobacterium tuberculosis

<400> SEQUENCE: 18

```
atggcaacac gttttatgac ggatccgcac gcgatgcggg acatggcggg ccgttttgag    60
gtgcacgccc agacggtgga ggacgaggct cgccggatgt gggcgtccgc gcaaaacatc   120
tcgggcgcgg gctggagtgg catggccgag gcgacctcgc tagacaccat ggcccagatg   180
aatcaggcgt ttcgcaacat cgtgaacatg ctgcacgggg tgcgtgacgg gctggttcgc   240
gacgccaaca actacgagca gcaagagcag gcctcccagc agatcctcag cagctaa     297
```

<210> SEQ ID NO 19
<211> LENGTH: 297
<212> TYPE: DNA
<213> ORGANISM: Mycobacterium tuberculosis

<400> SEQUENCE: 19

```
atgacctcgc gttttatgac ggatccgcac gcgatgcggg acatggcggg ccgttttgag    60
gtgcacgccc agacggtgga ggacgaggct cgccggatgt gggcgtccgc gcaaaacatt   120
tccggcgcgg gctggagtgg catggccgag gcgacctcgc tagacaccat gacccagatg   180
aatcaggcgt ttcgcaacat cgtgaacatg ctgcacgggg tgcgtgacgg gctggttcgc   240
gacgccaaca actacgaaca gcaagagcag gcctcccagc agatcctcag cagctga     297
```

<210> SEQ ID NO 20
<211> LENGTH: 435
<212> TYPE: DNA
<213> ORGANISM: Mycobacterium tuberculosis

<400> SEQUENCE: 20

```
atgtcataca tgattgccac accagcggcg ttgacggcgg cggcaacgga tatcgacggg    60
attggctcgg cggttagcgt tgcgaacgcc gggcggtcg ccgcgacaac cggagtgctg   120
gccgccggtg gcgatgaagt gttggcggcc atcgctaggc tgttcaacgc aaacgccgag   180
gaatatcacg ccctcagcgc gcaggtggcg gcgtttcaaa ccctgtttgt gcgcaccttg   240
```

```
actgggggt gcggagtctt tcgccggcgc cgaggccgcc aatgcgtcac agctgcagag    300
catcgcgcgg caggtgcggg gcgccgtcaa cgccgtcgcc ggtcaggtga cgggcaatgg    360
cggctccggc aacagcggca cttcggctgc ggcggccaac ccgaattccg acaacacagc    420
gagcatcgcc gatag                                                    435
```

```
<210> SEQ ID NO 21
<211> LENGTH: 2085
<212> TYPE: DNA
<213> ORGANISM: Mycobacterium tuberculosis

<400> SEQUENCE: 21
gtgtcgttgg tgatcgcgac gccgcagctg ctggcaactg cggctttgga tttagcgagt     60
attggttcgc aggtgagcgc ggctaatgcg gccgcggcga tgccgacgac ggaagtggtg    120
gctgcggctg ccgatgaagt gtcggcggcg attgcggggt tgttcggggc ccatgctcgg    180
cagtatcagg cgctcagcgt acaggtggca gcgtttcacg agcagtttgt gcaggcgttg    240
actgcggccg cgggtcggta tgccagcact gaggccgctg ttgagcggag tctgctgggt    300
gcggtgaatg cgcccaccga ggcgcttttg gggcgcccgt tgatcggaaa cggcgccgac    360
gggacggcac ccgggcagcc tggcgcggcc ggcgggttgc tgtttggcaa cggtggcaac    420
ggcgcggctg cgggttcgg tcaaaccggc ggcagcggag gcgcggccgg gttgatcggc    480
aacggcggca acgcggggc cggtggtacc ggcgcggccg gcggtgccgg tgggaacggg    540
gggtggttgt ggggcaacgg cggcaacggc ggtgtcggcg gcaccagcgt ggccgcaggc    600 atcggggtg cgggcggtaa cggcggcaac gccgggctgt tcggccatgg cggcgccggt    660
ggtaccggcg cgccggcct cgccggggca acggggtca atcccacgcc cggccccgcg    720
gccagcaccg gggacagccc ggcagatgtg tccggcatcg gtgatcaaac cggcggcgac    780
ggcggcacgg gcgccatgg cactgccggc acgccgaccg gtggcaccgg cggcgacggt    840
gccaccgcga cggcaggctc gggcaaggcc accggcggtg ccggtggtga cggcggtacc    900
gccgctgccg gtggcggcgg cggcaacggc ggcgacggcg gagtcgcgca gggcgacatt    960
gcgagcgcct ttggcggtga tggtggcaac gggtccgacg gtgtagccgc cggcagtggg    1020
ggtggtagcg gcggcgccgg aggcggcgct ttcgtacaca tcgccactgc cacctctacc    1080
ggtggtagcg gcggtttcgg tggtaacggg gctgccagtg ccgcctccgg cgccgacggt    1140
ggcgcagggg gagctggcgg caatggtggc gccggcgggt tgctattcgg tgatggcggc    1200
aacggtggcc ccggtggcgc gggtggtatc ggtggtgacg gcgccacggg ggggcccggg    1260
ggaagcggcg gcaacgctgg catcgcgagg tttgacagcc cagaccccga ggcagaaccc    1320
gatgtggtcg gcgcaagggg tggtgatggc gcaagggcg cagcggcct ggcgtcggc    1380 ggcgccggcg gaccggcgg cgcgggcgg aacggcggcg ccggcgggtt gttgttcggc    1440 aacgcggca acggcggcaa cgccggggcc ggcggggatg gcgcgccgg cgttgccggt    1500 gggggttggcg gtaacggcgg cggtggtggc accgcgacgt tcacgaagaa cccggtcgct    1560
ggtgtctggg cggtcggtgg cgtaggtggt gatggtggct ccggcggcag ctcgcttggt    1620
gtcggcgggg tgggcggagc cggtggcgtg ggtggcaagg gtgcgccag cggcatgttg    1680 atcggcaacg gcggcaacgg tggcagcggc ggagtcggtg gggccggtgg agtcggcggg    1740
gctggcggtg acgcggcaa cggcggctcc ggtggcaacg ccagtacttt tggcgatgag    1800
aactccatcg gcggggccgg cgggacgggc ggcaacgggg gcaacggcgc aaacggcggt    1860
```

```
aacggtggcg ctggcggtat tgccggcggt gcgggtgggt ccggagggtt cctcagcggt   1920
gccgcaggag tcagcggcgc tgacggtatc ggtggcgcgg gcggcgcagg cggtgccggt   1980
ggcgcgggcg gtagcggcgg tgaggcaggc gcggggggcc tcaccaacgg ccccgggtcc   2040
cctggcgttt ccggcaccga aggcatggcc ggcgcgcccg gctag                  2085

<210> SEQ ID NO 22
<211> LENGTH: 978
<212> TYPE: DNA
<213> ORGANISM: Mycobacterium tuberculosis

<400> SEQUENCE: 22
atgcatcagg tggaccccaa cttgacacgt cgcaagggac gattggcggc actggctatc     60
gcggcgatgg ccagcgccag cctggtgacc gttgcggtgc ccgcgaccgc caacgccgat    120
ccggagccag cgccccggt acccacaacg gccgcctcgc cgccgtcgac cgctgcagcg    180
ccacccgcac cggcgacacc tgttgccccc ccaccaccgg ccgccgccaa cacgccgaat    240
gcccagccgg gcgatcccaa cgcagcacct cgccggccc acccgaacgc accgccgcca    300
cctgtcattg ccccaaacgc accccaacct gtccggatcg acaacccggt tggaggattc    360
agcttcgcgc tgcctgctgg ctgggtggag tctgacgccg cccacttcga ctacggttca    420
gcactcctca gcaaaaccac cggggacccg ccatttcccg gacagccgcc gccggtggcc    480
aatgacaccc gtatcgtgct cggccggcta gaccaaaagc tttacgccag cgccgaagcc    540
accgactcca aggccgcggc ccggttgggc tcggacatgg gtgagttcta tgccctac     600 ccgggcaccc ggatcaacca ggaaaccgtc tcgctcgacg ccaacggggt gtctggaagc    660
gcgtcgtatt acgaagtcaa gttcagcgat ccgagtaagc cgaacggcca gatctggacg    720
ggcgtaatcg gctcgcccgc ggcgaacgca ccggacgccg gcccctca gcgctggttt    780 gtggtatggc tcgggaccgc caacaaccg gtggacaagg gcgcggccaa ggcgctggcc    840
gaatcgatcc ggccttttggt cgccccgccg ccggcgccgg caccggctcc tgcagagccc    900
gctccggcgc cggcgccggc cggggaagtc gctcctaccc cgacgacacc gacaccgcag    960
cggaccttac cggcctga                                                 978

<210> SEQ ID NO 23
<211> LENGTH: 1749
<212> TYPE: DNA
<213> ORGANISM: Mycobacterium tuberculosis

<400> SEQUENCE: 23
atgctcctgg ccctgctgcg ccagcacatc cgaccgtacc gccggctggt cgcgatgctg     60
atgatgctgc agctggtcag caccctggct tcgctatacc tcccgacggt caacgccgca    120
atcgtcgacg acgcgtcgc caagggcgac accgccacca tcgtacggct gggtgcggtg    180
atgcttgggg tgaccggatt gcaggtgctg tgcgcgatcg gggcggtcta tctgggctcc    240
cggaccgggg cgggtttcgg ccgtgacctg cgctcggcaa tgttcgaaca catcatcacc    300
ttctcggaac gcgagaccgc ccgattcggc gctccgacgt tgttgacccg cagcaccaac    360
gacgtccggc agatcctgtt cctggtccag atgaccgcca ccgtgctggt caccgcaccg    420
atcatgtgcg tcggcggaat catcatggcc atccaccagg aggccgcgct gacatggctg    480
ctgctggtca gcgttccgat tctggccgta gcaaactact ggatcatctc ccacatgctg    540
ccgctcttcc gccgcatgca gagcctgatc gacggcatca accgggtgat gcgcgatcag    600
ctgtccgggg tgcgagtggt ccgcgccttc acccgcgaag gctatgaacg cgacaagttc    660
```

```
gcgcaggcca atacggcgct gtcgaatgcc gcactgagcg ccggcaactg gcaagcactg    720
atgctgccgg tgaccacgct gaccatcaac gcatccagcg tcgcactgat ctggttcggt    780
gggctacgca tcgacagcgg ccagatgcag gtcggctccc tgatcgcctt cctgtcctac    840
ttcgcccaga tcctgatggc ggtgttgatg gcgaccatga cgctggccgt gctgccacga    900
gcgtcggtct gcgccgaacg catcaccgag gtgctttcca cgcccgccgc actcggtaac    960
cccgacaatc ccaagttccc gacggacggg gtcacgggcg tagtgcgctt ggctggcgca   1020
acctttacct atcctggcgc cgactgcccg gtgctgcagg acatttcgtt gactgcgcgg   1080 cccgtacca ccaccgcgat cgtcggcagt accggttcgg gcaagtcgac actggtgtcg   1140
ttgatctgcc ggctctacga cgtcaccgct ggcgcggtct tggttgacgg tatcgacgtc   1200
cgcgagtacc acaccgagcg gctctggtca gcgatcgggc tggtgcccca gcgcagctac   1260
ctcttctccg gaaccgtcgc ggacaacctg cgctacggcg ggggcccaga ccaggtagtc   1320
accgagcagg agatgtggga ggcgctgcgg gtcgccgcgg ccgacggctt tgtacaaaca   1380
gacgggctgc agacgcgtgt cgcccaaggt ggtgtcaact tctccggcgg gcagcgccaa   1440
cggctggcga tagcccgagc ggtcatccga cgtccggcca tctatgtgtt cgacgacgcg   1500
ttctccgcac ttgacgtgca caccgacgcc aaagtccacg catcgctgcg acaggtatct   1560
ggtgatgcaa ccatcattgt tgttacacaa cggatttcga atgccgctca ggccgaccag   1620
gtcatcgttg tcgataacgg taagatcgtc ggcacgggca cccacgaaac gctgctggcc   1680
gattgcccca cctatgccga attcgccgcc tcacaatcgc tgagcgccac ggtcgggggt   1740
gtagggtga                                                           1749
```

<210> SEQ ID NO 24
<211> LENGTH: 1407
<212> TYPE: DNA
<213> ORGANISM: Mycobacterium tuberculosis

<400> SEQUENCE: 24

```
atgtcctacg tcatcgcggc cccggagatg ttggcaacga cggccgcgga cgtggacggg    60
atcggttcgg cgatacgagc ggccagcgcg tccgctgcgg gtccaacgac cggactgctg   120
gccgcggccg ccgatgaggt gtcgtcggcc gctgcagcgc tgttcagcga atacgcgcgc   180
gaatgtcaag aggtcctaaa gcaggctgcg gcgttccatg gcgagttcac ccgggcgctg   240
gctgccgccg gggccgccta tgcccaggct gaagccagca caccgctgc tatgtcgggc   300 accgccgggt ccagcggcgc cctcggttct gtcgggatgc tgtcaggcaa cccgctaacc   360
gcgttgatga tgggcggcac cggggaaccg atccttagtg accgcgtctt ggcgatcatt   420
gacagcgcat acattcggcc cattttcggg cccaacaacc cggtcgccca gtacacgccc   480
gagcagtggt ggccgtttat cgggaacctg tcactggacc aatccatcgc ccagggtgtc   540
acgctgctga caacggcat caacgcggaa ctacaaaatg gcatgacgt cgtcgttttc   600 ggctactcgc aaagcgccgc ggtagcgacc aatgaaatac gcgctcttat ggcgttacca   660
ccgggccaag ccccagatcc aagccggctg gctttcacgt tgatcggtaa tatcaataac   720
cccaacggcg gcgtcctcga gcgttacgtg ggcctttacc tcccgttctt ggatatgtcg   780
ttcaacggtg cgactccacc ggattccccc taccagacct acatgtacac cggccaatac   840
gacggctacg cccacaaccc gcagtacccg ctcaatatct tgtcgaccct caacgccttc   900
atgggcatca gatgggtgca caacgcgtac cccttcaccg cggccgaggt tgccaatgcc   960
```

-continued

```
gtgccgttgc ccacgtctcc gggctacacc ggcaacaccc attactacat gtttctgacc    1020
caggacctgc cgctgttgca gccgattcgc gccatcccct tcgtagggac cccaatagcc    1080
gagctgattc agcccgacct acgggtgcta gtcgacttgg gctatggcta cggctacgcc    1140
gacgtaccca ccccggccag cctgttcgcg ccaatcaacc cgatcgccgt ggcctcggcc    1200
ctggcgaccg ggaccgtgca aggcccccaa gccgccctag taagcatcgg attgttaccg    1260
cagtccgcgc tacccaatac gtatccgtat cttccgtcgg cgaatccggg cctgatgttc    1320
aacttcggtc aatccagtgt gacggagttg tcggtgctca gtggcgccct cgggtccgta    1380
gcgagattga ttccaccgat cgcgtga                                        1407
```

<210> SEQ ID NO 25
<211> LENGTH: 11151
<212> TYPE: DNA
<213> ORGANISM: Mycobacterium tuberculosis

<400> SEQUENCE: 25

```
atggagtttc cggtgttgcc accggaaatc aactccgtgc tgatgtattc gggtgcgggg      60
tcgagcccgt tgctggcggc ggccgcggcg tgggatgggc tggctgagga gttggggtcg     120
gcggcggtgt cgtttgggca ggtgacgtcg ggcctgacgg cggggtgtg gcagggtgcg     180
gcggcggcgg cgatggcggc cgcgcggcg ccgtatgcgg ggtggttggg ttcggtggcg     240
gccgcggcca aggcggtggc cgggcaggcg cgggtggtgg tgggggtctt tgaggcggcg     300
ttggcggcga cggtggatcc ggcgctggtg gcggccaacc gggcgcggct ggtggcgttg     360
gcggtgtcga atctgttggg gcagaacacg ccggcgatcg cggccgccga ggccgagtac     420
gagctgatgt gggccgccga tgtggcggcg atggccggct accattccgg cgcgtcggct     480
gctgccgcgg cgttgccggc gttcagccca ccggcgcagg cgctgggggg aggtgtcggc     540
gcgttcctta ccgccctgtt cgccagccct gcgaaggcgc tgagcctgaa tgcgggtttg     600
ggcaatgtcg gcaattacaa cgtcggggtt ggcaatgtcg gggtgttcaa cctgggcgcg     660
ggcaatgtgg gtgggcagaa tctgggtttc gggaatgccg gtggcaccaa tgtcggggtc     720
ggcaacctcg gtaacgggaa tgtcgggttc ggcaactccg gtctgggggc gggcctggcc     780
ggcttgggca atatcgggtt gggcaatgcg ggcagcagca actatggttt cgcaaacctg     840
ggtgtgggca acatcggttt cggcaacacc ggcaccaaca cgtcggcgt cgggctcacc     900
ggcaaccacc tgacgggtat cggggggctg aattcgggca ccggggaatat cgggttgttc     960
aactccggca ccgggaatgt ggggttcttc aattcgggga ccgggaactt cggggtgttc    1020
aactcgggta attacaacac cggtgtcggt aatgcgggga cggccagcac ggggttgttc    1080
aatgccggca attcaacac cggcgtggtg aacgtgggca gttacaacac cggcagtttc    1140
aacgccggcg acaccaacac cggtggcttc aaccccggcg tgtgaacac cggctggctg    1200
aacaccggca caccaacac cggcatcgcc aactcgggca acgtcaacac cggcgcgttc    1260
atctcgggca acttcaacaa cggcgtgctg tgggtgggtg actaccaggg cctgttcggc    1320
gtctccgccg gctcgtcgat ccccgcaatt cccatcggcc tggtgctcaa cggcgacatc    1380
ggcccgatca ccatccagcc catcccgatc ctgcccacca tcccgctcag cattcaccaa    1440
accgtcaact tgggcccgct ggtggttccc gacatcgtga tccccgcctt cggcggcggt    1500
atcggcatac ccatcaacat cggccgctg accatcacac ccatcaccct gtttgcccaa    1560
cagacatttg tcaaccaatt gcccttccc accttcagtt tagggaaat cacaattcca    1620
caaatccaaa cctttgattc taacggtcag cttgtcagct ttatcggccc tatcgttatc    1680
```

```
gacaccacca ttcccggacc caccaatcca cagattgatt taacgatcag atgggatacc    1740
cctccgatca cgctgttccc gaatggcatc agtgctcccg ataatccttt ggggttgctg    1800
gtgagtgtgt cgatcagtaa cccgggcttt accatcccgg gatttagtgt tcccgcgcag    1860
ccgttgccgt tgtcgatcga tatcgagggc cagatcgacg ggttcagcac cccgccgatc    1920
acgatcgatc gcatcccccT gaccgtgggg ggcggggtca cgatcggccc catcacgatc    1980
cagggccttc atatcccggc ggcgccggga gtggggaaca ccaccacggc cccgtcgtcg    2040
ggattcttca actccggtgc gggtggggtg tcggtttcg gcaacgtcgg cgcgggcagc     2100
tcgggctggt ggaaccaggc gccgagcgcg ctgttggggg ccggttcggg tgttggcaac    2160
gtgggcaccc tgggctcggg tgtgctcaac ctgggctcag ggatctcggg gttctacaac    2220
accagcgtgt tgccttTcgg gacaccggcg gcggtgtcgg gcatcggcaa cctgggccag    2280
cagctgtcgg gggtgtcggc ggcgggaacc acgctgcgct cgatgctcgc cggcaacctc    2340
gggttggcca atgtgggcaa cttcaacacc gggttcggaa atgtcgggga cgtcaacctg    2400
ggtgcggcca acatcggtgg gcacaacctg ggcctgggca atgtcgggga cggcaacctg    2460
gggttgggca acatcggcca tgcaacctg gggtttgcca acttgggcct gaccgccggc    2520
gcggcggggg tgggcaatgt tggttttggc aatgccggca tcaacaacta tggcttggcg    2580
aacatgggtg tgggcaatat tgggtttgcc aacaccggca cggcaacat cgggatcggg     2640
ctggtcgggg accatcggac cgggatcggg ggcttgaact ccggcatcgg caatatcggg    2700
ttgttcaact ccggcaccgg caacgtcggg ttcttcaatt ccgggaccgg caacttcggc    2760
atcgggaact ccggccgctt caacaccggg atcggtaata gcggaacggc cagcaccggg    2820
ctcttcaatg ccggcagctt cagcaccggc atcgccaaca ctggtgacta caacacgggc    2880
agcttcaacg ccggcgacac caacaccggt ggcttcaacc cgggcggcat caacaccggc    2940
tggttcaaca ccgggcatgc caacaccggg ttggccaacg cgggcacctt cggcaccggc    3000
gccttcatga cgggcgacta cagcaacggc ctgttgtggc ggggcggcta cgagggcctg    3060
gtcggcgtcc gcgtcgggcc cacgatctcc caattcccgg tcaccgtgca cgcgatcggc    3120
ggggtgggcc cgctgcatgt ggcgcccgtc ccggtacccg ccgtgcacgt cgagatcacc    3180
gacgccaccg tcggcctggg tccgttcacc gtcccaccga tcagcattcc ctcacttccc    3240
atcgccagca tcaccggaag cgtggacctg ccgcaaaaca ccatctcgcc gattcgcgct    3300
cttgacccgc tcgccggttc gatagggctt tttctcgagc cgttccgcct cagtgaccca    3360
tttatcacca ttgatgcgtt ccaagttgtt gccggtgtct tgttcctaga gaacatcatt    3420
gtgcccggcc tcacggttag cggtcagata ttggtcaccc cgacaccaat tcccctaacc    3480
ctcaacttgg acaccacccc gtggacgctt ttcccgaatg gtttcaccat tcccgcgcaa    3540
acccccgtga cggtgggtat ggaggtcgcc aacgacgggt tcaccttctt cccgggtggg    3600
ctgacctttc cgcgggcctc cgccggggtc accggactgt ccgtggggct ggacgcgttc    3660
acgctgttgc ccgacgggtt caccctcgac accgtgccgg cgaccttcga cggcaccatc    3720
ctcatcggcg atatcccgat cccgatcatc gatgtgccgg cggtgccggg gttcggcaac    3780
accaccacg ccccatcgtc ggggttcttc aacaccggcg gcggcggtgg atcggggttc    3840
gccaacgtcg gcgcgggcac gtcgggctgg tggaaccagg ggcacgacgt gttagcaggg    3900
gcgggctcgg gagttgccaa tgccggcacg ctgagctcgg gcgtgctgaa cgtcggctcg    3960
gggatctccg ggtggtacaa caccagcacc ctgggagcgg gcaccccggc ggtggtctcg    4020
```

-continued

```
ggcatcggca acctcggcca gcagctgtcg gggttcttgg caaatgggac cgtgctcaac      4080
cggagcccca ttgtcaatat cgggtggggcc gatgtgggcg cgttcaacac cgggttgggc      4140
aatgtggggg acctcaactg gggtgcggcc aacatcggcg cgcagaacct gggcctgggc      4200
aatctcggca gcgggaacgt cgggttcggc aacatcggtg ccggcaacgt cgggttcgcc      4260
aactcgggtc cggcggtggg cctggccggc ctgggcaacg tgggggttgag caatgccggc      4320 agcaacaact gggggctggc caacctgggt gtgggcaaca tcgggttggc caacaccggc      4380
acgggcaaca tcgggatcgg gctggtcggc gactaccaga ccggcatcgg cggcctcaac      4440
tcgggtagtg gcaatatcgg attgttcaat tccggcaccg gcaatgtcgg gttcttcaac      4500
accggcaccg gcaacttcgg actgttcaac tccggtagtt tcaacaccgg catcggtaat      4560 agcgaaccg gcagtactgg gctcttcaat gccggcaatt tcaacaccgg catcgccaac      4620
cccgggtcgt acaacacggg cagcttcaat gtcggtgata ccaacaccgg tggtttcaac      4680
ccgggcgaca tcaacaccgg ctggttcaac accggcatta tgaatacggg cacccgcaac      4740
accggcgccc tcatgtcggg gaccgacagc aacggcatgc tgtggcgcgg cgaccacgag      4800
ggcctgttcg gcctgtccta tggcatcacg atcccgcaat tcccgatccg catcaccacg      4860
actggcggta tcggccccat cgtcatcccg gacaccacga tccttccgcc gctgcacctg      4920
cagatcaccg gcgacgcgga ctacagcttc accgtgcccg acatccccat ccccgccatc      4980
cacatcggca tcaatggcgt cgtcaccgtc ggcttcaccg ccccggaagc cacccctgctg     5040 tccgccctga agaataacgg tagcttcatc agcttcggcc ccatcacgct ctcgaatatc      5100
gatattccgc ccatggattt cacgttaggc ctgcccgttc ttggtcctat cacggggccaa     5160 ctcggaccaa ttcatcttga gccaatcgtg gtggccggga tcgtgtgcc cctggagatc       5220 gagcccatcc cctgatgc gatttcgttg agtgagtcga ttcctatccg catacctgtt       5280
gatattccgg cctcggtcat cgatgggatt tcaatgtcgg aagtggtgcc gatcgatgcg      5340
tccgtggaca tcccggcgt cacgatcaca ggcaccacca tttccgcgat cccgctgggc       5400
ttcgacattc gcaccagtgc cggaccctc aacatcccga tcatcgacat cccggcggcg      5460
ccgggcttcg ggaactcgac ccagatgccg tcgtcgggt tcttcaacac cggtgccggc      5520
ggcggatcgg gcatcggcaa cttgggtgcg ggcgtgtcgg gcctgctcaa ccaggccggc      5580
gcggggtcac tggtggggac actctcgggg ctgggcaatg ccggcaccct ggcctcgggt      5640
gtgctgaact ccggcaccgc catctccggg ctgttcaacg tgagcacgct ggacgccacc      5700
accccggcgc tgatctcggg gttcagcaac ctcggcgacc atatgtcggg ggtgtccatc      5760
gatggcctga tcgcgatcct caccttccca cctgccgagt ccgtgttcga tcagatcatc      5820
gacgcggcca tcgccgagct gcagcacctc gacatcggca acgctttggc cttgggcaat      5880
gtcggcgggg tgaacctcgg tttggctaac gtcggtgagt caacctgggg tgcgggcaac      5940
gtcggcaaca tcaacgtcgg cgccggcaac ctcggcggca gcaacttggg gttgggcaac      6000
gtcgggaccg gcaacctcgg gttcggcaac atcggtgccg gcaatttcgg attcggcaac      6060
gcgggcctga ccgcgggcgc gggggggcctg gcaatgtgg ggttgggtaa cgccggcagc      6120
ggcagctggg ggttggccaa cgtggtgtg gcaatatcg ggttggccaa caccggcacc       6180
ggcaacatcg ggatcgggct gaccggggac tatcggaccg ggatcggcgg cctgaactcg      6240
ggcaccggga acctcgggtt gttcaactcg ggcaccggca acatcgggtt cttcaacacc      6300
gggaccggga acttcgggct gttcaactcg ggcagttaca gcaccggtgt ggggaatgcg      6360
ggcacggcca gcaccggggtt gttcaacgcg gggaacttca acaccggtct ggccaatgcc      6420
```

```
ggctcctaca acaccggcag cctcaacgtg ggcagcttca acaccggcgg cgtcaacccg   6480
ggcaccgtca acaccggctg gttcaacacc ggccacacca acaccggcct gttcaacacc   6540
ggcaacgtca acaccggcgc gttcaactcc ggcagcttca acaacggggc gctgtggacc   6600
ggtgactacc acgggctggt cggcttctcc ttcagcatcg acatcgccgg cagcaccctg   6660
ctggacctca acgaaaccct caacctgggc cccatccaca tcgagcagat cgacatcccc   6720
ggcatgtcgc tgttcgacgt ccacgaaatc gtcgagatcg gacccttcac catcccgcag   6780
gtcgatgttc ccgcgatacc gctagagatc cacgaatcga tccacatgga tcccatcgtc   6840
ctggtgcccg ccaccacaat tcccgcacag acgagaacca ttccgctgga catccccgcc   6900
tcacccgggt caaccatgac gcttccgctc atcagcatgc gcttcgaagg cgaggactgg   6960
atcctcgggt cgaccgcggc gattcccaat ttcggagacc ccttcccggc gcccacccag   7020
ggcatcacca ttcacaccgg ccctggcccc ggaacgaccg gcgagctcaa gatatctatt   7080
ccgggtttcg agattccgca aatcgctacc acgagattcc tgttggacgt gaacatcagc   7140
ggtggtctgc cggccttcac cttgttcgcg ggtggcctga cgatccccac gaacgccatc   7200
ccgttaacga tcgatgcgtc cggcgcgctg gatccgatca cgattttccc gggtgggtac   7260
acgatcgacc cgctgccgct gcacctggcg ctgaatctca ccgtgcccga cagcagcatc   7320
ccgatcatcg atgtcccgcc gacgccaggg ttcggcaaca ccacggcgac cccgtcgtcg   7380
gggttcttca actccggcgc cggtggggtg tcggggttcg gaaacgtcgg gtcgaacctg   7440
tcgggctggt ggaaccaggc ggcgagcgcg ctggcgggt cgggatcggg ggtgttgaat   7500
gtcggcacgc tgggctcggg tgtgctcaac gtcggctcgg gtgtctcggg gatctacaac   7560
accagcgtgt tgccgctcgg gacgccgcg gtgctgtcgg gcctcggcaa cgtcggccat   7620
cagctgtcgg gcgtgtctgc ggccgggacc gcgttgaacc agatccccat cctcaacatc   7680
gggttggcgg atgtgggcaa cttcaacgtc gggttcggca acgtcgggga cgttaacctg   7740
ggcgcggcca acctcggtgc gcaaaaccfg ggctgggca acgtcggcac cggcaacctc   7800
ggcttcgcca acgtcggcca cggcaatatc ggtttcggca attcgggtct gaccgccggc   7860
gcggccggcc tgggcaacac ggggttcggc aatgccggca gcgccaacta tggtttcgcc   7920
aaccagggcg tgcgcaacat cgggttggcc aacaccggca ccggcaacat cgggatcggg   7980
ctggtggggg acaacctcac cggcatcggg ggcctgaact ccggtgccgg caatatcggc   8040
ttgttcaact ccggcaccgg caacatcggg ttcttcaact ccgggaccgg caacttcggc   8100
atcggtaact cggcagcttt caacaccggc atcggcaata gcggaacggg cagcactggg   8160
ctcttcaatg ccggcagctt caacaccggc gtggccaacg ccggcagcta caacaccggc   8220
agcttcaatg ccggcgacac caacaccggg gggttcaacc cggcaccat caacaccggc   8280 tggttcaaca ccggccacac caataccggc atcgccaact cgggcaacgt cggcaccggc   8340
gcgttcatgt cgggcaactt cagcaacggc ctgttgtggc ggggtgatca cgagggcctg   8400
ttcagcctgt tctacagcct cgacgtgccc cggatcacca tcgtggacgc ccacctcgac   8460
ggcggcttcg acccgtggt cctcccgccc atcccggtgc cggccgttaa tgcgcacctg   8520
accggaaacg tcgcgatggg cgcattcacc attccgcaga tcgacatccc cgcactcacc   8580
ccaaacatca ccggaagcgc cgccttccgc atcgttgtgg ggtccgtgcg cattccgccg   8640
gtgagtgtca ttgtggagca aataatcaac gcctcggttg gggcggagat gaggatagat   8700
cccttcgaaa tgtggactca aggcactaat ggccttggta taaccttcta ttcattcgga   8760
```

```
tcggccgacg gttcgcccta cgccaccggc ccactcgttt tcggcgccgg cacgagcgac      8820
ggaagccatc tcaccatttc cgcgtccagc ggggcgttta ccactccgca gctcgaaact      8880
ggcccgatca cgttgggctt ccaggtgccc ggcagcgtca acgcgatcac cctcttcccc      8940
ggtggtttga cgttcccggc gacctcgctg ctgaacctgg acgtgaccgc cggcgccggc      9000
ggcgtggaca tcccggccat cacctggccc gagatcgcgg cgagcgccga cggctcggtg      9060
tatgtcctcg ccagcagcat cccgctgatc aacatcccgc ccaccccggg cattgggaac      9120
agcaccatca ccccgtcgtc gggcttcttc aacgccggcg cgggcggggg atcgggcttc      9180
ggcaacttcg gcgcgggcac ctcgggctgg tggaaccagg cgcacaccgc gctggcgggg      9240
gcgggctcgg gttttgccaa cgttggcacg ctgcattccg gtgtgctcaa cctgggctcg      9300
ggtgtctcgg ggatctacaa caccagcacg ctggggtgg ggaccccggc gctggtctca      9360
ggcctgggca acgtcggcca ccaactgtcg gggctgcttt ccggcgggtc cgcggtgaac      9420
ccggtgaccg ttctgaatat cgggttggcc aacgtcggca gccacaacgc cggtttcggc      9480
aatgtcgggg aggtcaacct gggcgcgcc aacctcggcg cgcacaacct gggcttcgga      9540
aatatcggcg ccggcaacct ggggttcggc aatattggcc acggcaatgt cggagtcggc      9600
aactcgggtc tgaccgcggg cgtgccgggc ctggcaatg tgggttggg caatgccggc      9660
ggcaacaact gggggttggc caacgtgggc gtgggcaata tcgggttggc caacaccggc      9720
accggcaaca ttgggatcgg gctgaccggc gactaccaga ccggcatcgg cggcctaaat      9780
tccggtgccg gcaacctggg gttgttcaac tccggcgccg gcaacgtcgg gttcttcaac      9840
accgggaccg gcaacttcgg gttgttcaac tccggcagct tcaacaccgg cgtcggcaat      9900
agcggaacgg gcagcactgg gctcttcaat gccggcagtt tcaacaccgg tgtggccaac      9960
gccgcagct acaacacggg cagcttcaat gtcggtgaca ccaacaccgg gggcttcaac     10020
ccgggcagca tcaacaccgg ctggctcaac gccgcaacg ccaacaccgg ggtggccaac     10080
gcgggcaatg tcaacaccgg cgccttcgtc accggcaact tcagcaacgg catcctgtgg     10140
cgcggcgact accagggcct ggccggcttc gccgtgggct acaccctccc gctgttcccc     10200
gcggtgggc ccgacgtcag cggcgggatc ggcccgatta ccgtgctgcc gcccatccac     10260
atcccgccca ttccggtcgg cttcgccgcg gtcggtggca tcggcccgat cgccatcccg     10320
gacatctctg ttcatccat tcacttgggc ctcgaccccg ccgtccatgt cggctccatc     10380
accgtcaacc ccattaccgt caggaccccg cccgtgctcg tcagttactc ccaaggagcc     10440
gtcaccagca cgtccggacc aacctcagag atttgggtca gcccagctt cttccccgga     10500
atccggatcg cgccctctag cggcgggggt gcaacgtcca cgcaaggggc atactttgtg     10560
gggcccatct ccatccctc cggcacggtg accttcccgg gattcaccat cccctcgac     10620
ccgatcgaca tcggcctgcc ggtgtcgctg accatcccgg ggttcaccat cccggcggc     10680
accctgatcc ccaccctccc gctgggcctc gcgttgtcca atggcatccc gcccgtcgac     10740
atcccggcca tcgttctcga ccggatcttg ctggacctgc acgccgacac cactatcggc     10800
ccgatcaacg tcccgatcgc cgggttcggc ggggcgccgg gtttcgggaa ctcgaccacg     10860
ctgccgtcgt cgggcttctt caacaccgga gctggcggcg gttcgggctt tagcaacacc     10920
ggcgcgggca tgtcgggatt gctcaacgcg atgtcggatc cgctgctcgg gtcggcgtcg     10980
ggcttcgcca acttcggcac ccagctctcc ggcatcctca accgcggcgc cggcatctcg     11040
ggcgtgtaca acaccggcgc gctgggtgtt gtcaccgcgg ccgtcgtctc gggtttcggc     11100
aacgtcggcc agcaactgtc gggcttgctc ttcaccggcg tcgggcccta a              11151
```

<210> SEQ ID NO 26
<211> LENGTH: 10
<212> TYPE: PRT
<213> ORGANISM: Mycobacterium tuberculosis

<400> SEQUENCE: 26

Ala Glu Met Lys Thr Asp Ala Ala Thr Leu
1               5                   10

<210> SEQ ID NO 27
<211> LENGTH: 10
<212> TYPE: PRT
<213> ORGANISM: Mycobacterium tuberculosis

<400> SEQUENCE: 27

Arg Ala Asp Glu Glu Gln Gln Gln Ala Leu
1               5                   10

<210> SEQ ID NO 28
<211> LENGTH: 10
<212> TYPE: PRT
<213> ORGANISM: Mycobacterium tuberculosis

<400> SEQUENCE: 28

Thr Ala Ala Gln Ala Ala Val Val Arg Phe
1               5                   10

<210> SEQ ID NO 29
<211> LENGTH: 8
<212> TYPE: PRT
<213> ORGANISM: Mycobacterium tuberculosis

<400> SEQUENCE: 29

Ala Glu Met Lys Thr Asp Ala Ala
1               5

<210> SEQ ID NO 30
<211> LENGTH: 11
<212> TYPE: PRT
<213> ORGANISM: Mycobacterium tuberculosis

<400> SEQUENCE: 30

Ala Glu Met Lys Thr Asp Ala Ala Thr Leu Ala
1               5                   10

<210> SEQ ID NO 31
<211> LENGTH: 9
<212> TYPE: PRT
<213> ORGANISM: Mycobacterium tuberculosis

<400> SEQUENCE: 31

Asn Ile Arg Gln Ala Gly Val Gln Tyr
1               5

<210> SEQ ID NO 32
<211> LENGTH: 9
<212> TYPE: PRT
<213> ORGANISM: Mycobacterium tuberculosis

<400> SEQUENCE: 32

Glu Met Lys Thr Asp Ala Ala Thr Leu
1               5

```
<210> SEQ ID NO 33
<211> LENGTH: 10
<212> TYPE: PRT
<213> ORGANISM: Mycobacterium tuberculosis

<400> SEQUENCE: 33

Ala Glu Met Lys Thr Asp Ala Ala Thr Leu
1               5                   10

<210> SEQ ID NO 34
<211> LENGTH: 9
<212> TYPE: PRT
<213> ORGANISM: Mycobacterium tuberculosis

<400> SEQUENCE: 34

Leu Leu Asp Ala His Ile Pro Gln Leu
1               5

<210> SEQ ID NO 35
<211> LENGTH: 9
<212> TYPE: PRT
<213> ORGANISM: Mycobacterium tuberculosis

<400> SEQUENCE: 35

Ala Ala His Ala Arg Phe Val Ala Ala
1               5

<210> SEQ ID NO 36
<211> LENGTH: 11
<212> TYPE: PRT
<213> ORGANISM: Mycobacterium tuberculosis

<400> SEQUENCE: 36

Ala Val Ile Asn Thr Thr Cys Asn Tyr Gly Gln
1               5                   10

<210> SEQ ID NO 37
<211> LENGTH: 9
<212> TYPE: PRT
<213> ORGANISM: Mycobacterium tuberculosis

<400> SEQUENCE: 37

Ala Ser Pro Val Ala Gln Ser Tyr Leu
1               5

<210> SEQ ID NO 38
<211> LENGTH: 10
<212> TYPE: PRT
<213> ORGANISM: Mycobacterium tuberculosis

<400> SEQUENCE: 38

Glu Leu Pro Gln Trp Leu Ser Ala Asn Arg
1               5                   10
```

METHODS FOR DETECTING A MYCOBACTERIUM TUBERCULOSIS INFECTION

PRIORITY CLAIM

This is a continuation of U.S. patent Ser. No. 13/244,126, filed on Sep. 23, 2011, which is a continuation of U.S. patent application Ser. No. 12/282,862, filed on Sep. 12, 2008, now issued as U.S. Pat. No. 8,053,181, which is the U.S. National Stage of PCT Application No. PCT/US2007/006534, filed Mar. 14, 2007, which was published in English under PCT Article 21(2), which in turn claims the benefit of U.S. Provisional Application No. 60/782,364, filed Mar. 14, 2006. The prior applications are all incorporated herein by reference in their entirety.

STATEMENT OF GOVERNMENT SUPPORT

This invention was made with United States government support pursuant to Grant No. NIH-R01-AI48090 and Grant No. NIH NIAID HHSN266200400081C N01-AI-40081 from the National Institutes of Health; the United States government has certain rights in the invention. This invention was also made with support from the Department of Veterans Affairs.

FIELD

This application relates to the field of diagnosis, specifically to methods for detecting a *Mycobacterium tuberculosis* (Mtb) infection in a subject.

BACKGROUND

*Mycobacteria* are a genus of aerobic intracellular bacterial organisms that, upon infection of a host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonei, M. haemophilum* and *M. intracellulare* (see Wolinsky, E., Chapter 37 in Microbiology: Including Immunology and Molecular Genetics, 3rd Ed., Harper & Row, Philadelphia, 1980).

One third of the world's population harbors *M. tuberculosis* and is at risk for developing tuberculosis (TB). In immunocompromised patients, tuberculosis is increasing at a nearly logarithmic rate, and multidrug resistant strains are appearing. In addition, Mycobacterial strains which were previously considered to be nonpathogenic strains (e.g., *M. avium*) have now become major killers of immunosuppressed AIDS patients. Moreover, current Mycobacterial vaccines are either inadequate (such as the BCG vaccine for *M. tuberculosis*) or unavailable (such as for *M. leprae*) (Kaufmann, S., Microbiol. Sci. 4:324-328, 1987; U.S. Congress, Office of Technology Assessment, The Continuing Challenge of Tuberculosis, pp. 62-67, OTA-H-574, U.S. Government Printing Office, Washington, D.C., 1993).

Inhibiting the spread of tuberculosis requires effective vaccination and accurate, early diagnosis of the disease. Currently, vaccination with live bacteria is the most efficient method for inducing protective immunity. The most common *Mycobacterium* employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public.

Diagnosis of tuberculosis is commonly achieved using a skin test, which involves intradermal exposure to tuberculin PPD (protein-purified derivative). Antigen-specific T cell responses result in measurable induration at the injection site by 48 to 72 hours after injection, which indicates exposure to Mycobacterial antigens. However, the sensitivity and specificity of this test are not ideal; individuals vaccinated with BCG cannot be distinguished from infected individuals. Accordingly, there is a need in the art for improved diagnostic methods for detecting tuberculosis.

SUMMARY

Methods for diagnosing an infection with *Mycobacterium tuberculosis* (Mtb) are disclosed herein. The methods can include detecting CD8$^+$ T cells and/or CD4$^+$ that specifically bind an Mtb polypeptide of interest. The methods can also include detecting a delayed type hypersensitivity reaction in a subject and/or can include detecting specific Mtb polypeptides and polynucleotides. The disclosed assays can be used individually or in combination. The *Mycobacterium tuberculosis* infection can be a latent or active infection.

In several embodiments, methods are provided for detecting *Mycobacterium tuberculosis* in a subject. These methods include contacting a biological sample from the subject comprising T cells, such as CD8$^+$ T cells and/or CD4$^+$ T cells, with one or more *Mycobacterium* polypeptides, or an antigen presenting cell presenting the one or more *Mycobacterium* polypeptides. The one or more *Mycobacterium* polypeptides include an amino acid sequence set forth as (a) one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11 or SEQ ID NO: 12, wherein the nine to twenty consecutive amino acids specifically bind major histocompatibility complex (MHC) class I. It is determined whether the T cells specifically recognize the *Mycobacterium* polypeptide.

In additional embodiments, methods are provided for detecting *Mycobacterium tuberculosis* in a subject, wherein the methods include administering to the subject an effective amount of a *Mycobacterium* polypeptide into the skin, subcutaneously or intradermally. The *Mycobacterium* polypeptide includes an amino acid sequence set forth as (a) one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11 or SEQ ID NO: 12, wherein the nine to twenty consecutive amino acids specifically bind major histocompatibility complex (MHC) class I. The presence of T cells that specifically recognize the *Mycobacterium* polypeptide are detected in the subject.

In further embodiments, methods are disclosed for detecting a *Mycobacterium tuberculosis* infection in a subject, wherein the methods include detecting the presence of a Mycobacterium polypeptide or a polynucleotide encoding the polypeptide in a sample from the subject. The Mycobacterium polypeptide includes an amino acid sequence set forth as one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

Additionally, reagents for the detection of a *Mycobacterium* infection in a subject are described.

The foregoing and other features and advantages will become more apparent from the following detailed description of several embodiments, which proceeds with reference to the accompanying figures.

BRIEF DESCRIPTION OF THE FIGURES

FIG. 3A-3D are a set of digital images showing the definition of Antigenic Specificity and HLA-Restriction (the characterization of T cell clone D466 D6). For the results shown in FIGS. 3a-3c, to Identify the antigen and minimal epitope recognized by T cell clone, D466 D6, T-cells (5000 cells/well) were incubated with autologous LCL (20,000/well) and 5 μg/ml of antigen. IFN-γ was assessed by ELISPOT after eighteen hours of co-culture. For the results presented in FIG. 3a, antigens consisted of peptide pools representing known CD4$^+$ antigens, made up of 15 amino acid (aa) peptides overlapping by 11 aa. For the results presented in FIG. 3b, antigens consisted of individual 15 aa CFP10 peptides that together constitute the peptide pool. For the results presented in FIG. 3c, antigens consisted of individual nested CFP10$_{1-15}$ peptides (10 aa, 9 aa or 8 aa), used to further map the epitope. For the results presented in FIG. 3d, the restricting allele was identified using LCL (20,000/well) expressing HLA alleles matching D466 at one or two alleles, pulsed with CFP10$_{2-10}$ (5 μg/ml) as APC. After 2 hours, cells were washed and incubated with T-cells (500 cells/well) in an IFN-γ ELISPOT assay.

Figure 7:
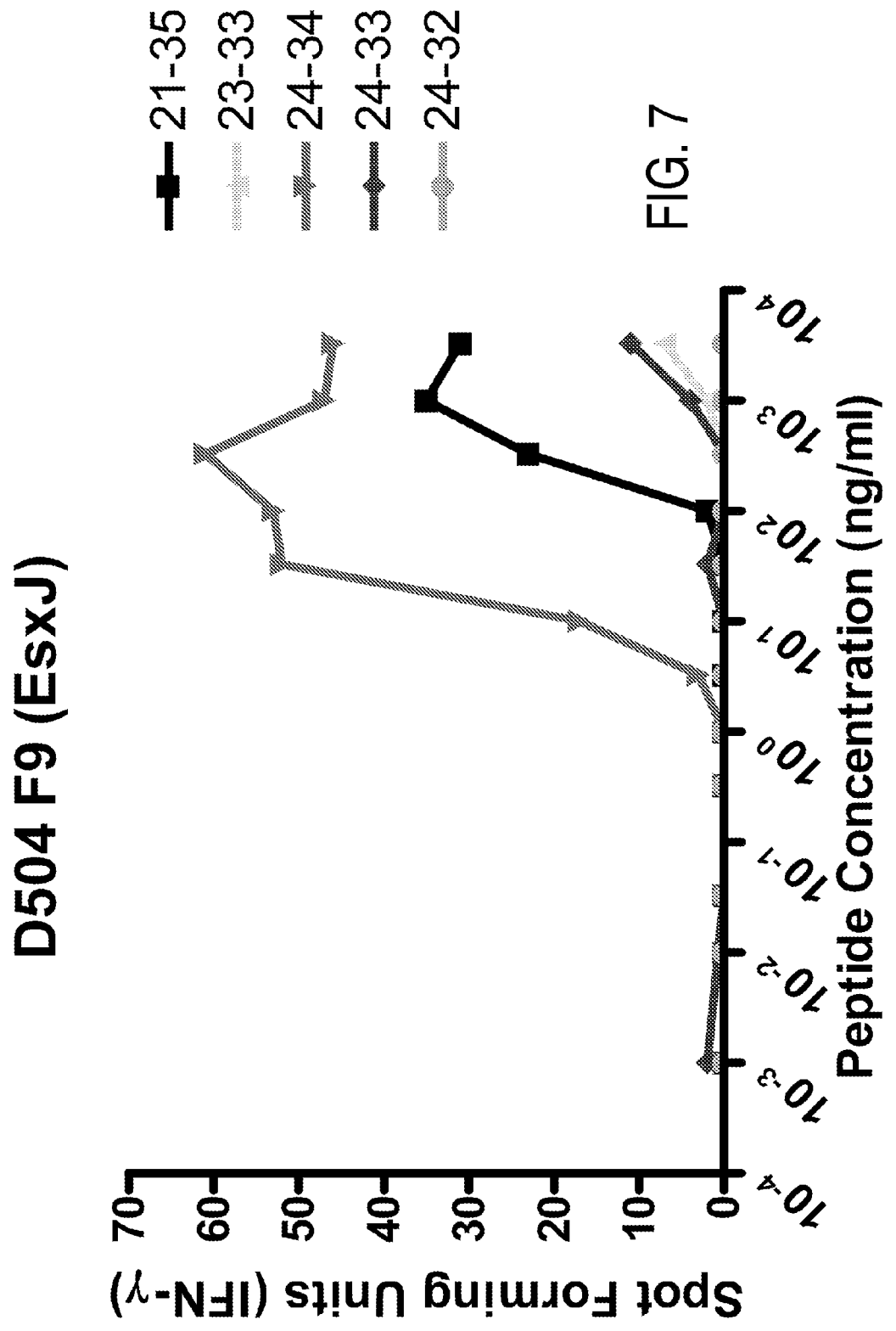

FIG. 7 is a line graph showing the mapping of Minimal Epitope for D504 Clones. To determine the minimal epitope, autologous LCL (20,000/well) was co-cultured with T-cell clones (1,000 cells/well) and the peptide at the concentration indicated. IFN-γ was assessed by ELISPOT after eighteen hours co-culture. Each point represents the mean of duplicate determinations.

SEQUENCE LISTING

Figure 1:
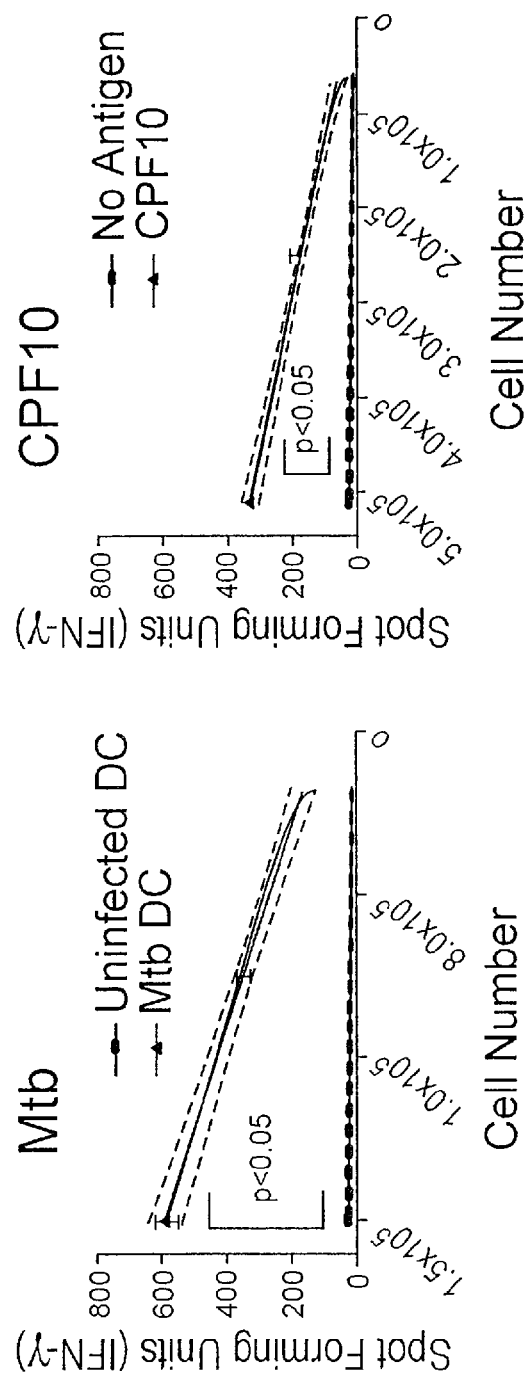
FIG. 1 is two graphs showing the determination of human effector cell frequencies ex vivo using the IFN-γ ELISPOT assay. Magnetic bead-purified CD8$^+$ T cells were cultured with DC (20,000/well) either infected with Mtb (H37Rv, MOI=50) or pulsed with peptide pool representing CFP10 (5 μg/ml each peptide; 15-mers overlap 11 aa) in an IFN-γ ELISPOT assay. Each responding T cell population was tested in duplicate at four different cell concentrations. To determine the effector cell frequency of antigen-specific T cells, the average number of spots per well for each duplicate was plotted against the number of responder cells per well. Linear regression analysis was used to determine the slope of the line, which represents the frequency of antigen-specific T cells. The assay was considered positive (reflecting the presence of a primed T cell response), if the binomial probability for the number of spots was significantly different by experimental and control assays.

The Sequence Listing is submitted as an ASCII text file [899-77364-31_Sequence_Listing.txt, Dec. 14, 2012, 84.4 KB], which is incorporated by reference herein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-12 are the amino acid sequence of Mtb polypeptides.

SEQ ID NOs: 13-14 are amino acids of Mtb peptides.

SEQ ID NOs: 15-25 are the nucleic acid sequences of polynucleotides encoding the Mtb polypeptides.

SEQ ID NOs: 26-38 are the amino acid sequences of specific Mtb epitopes.

DETAILED DESCRIPTION

Methods for detecting an infection with *Mycobacterium tuberculosis* in a subject are disclosed. The methods include detecting the presence of T cells, such as but not limited to CD8+ T cells, that specifically recognize a *Mycobacterium tuberculosis* (Mtb) polypeptide. The methods include in vitro assays for detecting the presence of CD8$^+$ T cells in a biological sample, and in vivo assays that detect a delayed type hypersensitivity reaction. The methods can also include detecting Mtb polypeptides and polynucleotides. Reagents for the detection of an Mtb infection are also disclosed.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tuberculosis. A disease-specific antigen can be an antigen recognized by T cells or B cells.

Antibody: Immunoglobulin molecules and immunologically active portions of immunoglobulin molecules, i.e., molecules that contain an antigen binding site that specifically binds (immunoreacts with) an antigen, such as an Mtb polypeptide.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., *Nature* 341:544-

546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

Antigen presenting cell (APC): A cell that can present an antigen to T cell, such that the T cells are activated. Dendritic cells are the principle antigen presenting cells (APCs) involved in primary immune responses. Their major function is to obtain antigen in tissues, migrate to lymphoid organs and present the antigen in order to activate T cells.

When an appropriate maturational cue is received, dendritic cells are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of dendritic cells to coordinate the activation and effector function of other surrounding lymphocytes that ultimately provide protection for the host.

cDNA (complementary DNA): A piece of DNA lacking internal, non-coding segments (introns) and regulatory sequences that determine transcription. cDNA is synthesized in the laboratory by reverse transcription from messenger RNA extracted from cells.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class 1 molecule. Cells that express CD8 are often cytotoxic T cells. "CD8+ T cell mediated immunity" is an immune response implemented by presentation of antigens to CD8+ T cells.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: "Conservative" amino acid substitutions are those substitutions that do not substantially affect or decrease an activity or antigenicity of the *Mycobacterium* polypeptide. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |

-continued

| Original Residue | Conservative Substitutions |
| --- | --- |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against and unsubstituted polypeptide, such a *Mycobacterium* antigen. Thus, in one embodiment, non-conservative substitutions are those that reduce an activity or antigenicity.

Consists Essentially Of/Consists Of: With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. A polypeptide that consists of a specified amino acid sequence does not include any additional amino acid residues, nor does it include additional non-peptide components, such as lipids, sugars or labels.

Contacting: The process of incubating one agent in the presence of another. Thus, when a cell is contacted with an agent, the cell is incubated with the agent for a sufficient period of time for the agent and the cell to interact.

Costimulatory molecule: Although engagement of the TCR with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Cytokine: Proteins made by cells that affect the behavior of other cells, such as lymphocytes. In one embodiment, a cytokine is a chemokine, a molecule that affects cellular trafficking. Specific, non-limiting examples of cytokines include the interleukins (IL-2, IL-4, IL-6, IL-10, IL-21, etc.), and interferon (IFN)-γ.

Degenerate variant: A polynucleotide encoding an epitope of an Mtb polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the Mtb polypeptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, tuberculosis. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as tuberculosis.

Displaying: The process of localizing a peptide:antigen complex, or a peptide, on the outer surface of a cell where the peptide:antigen complex or peptide is accessible to a second cell, molecules displayed by a second cell, or soluble factors. A peptide, or a peptide:antigen complex, is "displayed" by a cell when it is present on the outer surface of the cell and is accessible to a second cell, to molecules displayed by the second cell, or to soluble factors.

Epitope: An antigenic determinant. These are particular chemical groups or peptide sequences on a molecule that are antigenic, i.e. that elicit a specific immune response. An antibody specifically binds a particular antigenic epitope on a polypeptide, such a *Mycobacterium* polypeptide.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Fractionating: Subjecting a sample to conditions or procedures which separate the components of the sample based on physical or chemical properties such as, but not limited to, size, charge, solubility, or composition. Example of fractionation procedures include, but are not limited to, selective precipitation, organic extraction, size exclusion dialysis or chromatography, such as ion exchange chromatography. In one embodiment, a fraction is a soluble extract or an organic extract of an organism, such as a *Mycobacterium*.

Functionally Equivalent: Sequence alterations, such as in an epitope of an antigen, that yield the same results as described herein. Such sequence alterations can include, but are not limited to, conservative substitutions, deletions, mutations, frameshifts, and insertions.

Heterologous: Originating from separate genetic sources or species. A polypeptide that is heterologous to an Mtb polypeptide originates from a nucleic acid that does not encode the Mtb polypeptide. In one specific, non-limiting example, a polypeptide comprising nine consecutive amino acids from an Mtb polypeptide, or at most 20 consecutive amino acids from the Mtb polypeptide, and a heterologous amino acid sequence includes a β-galactosidase, a maltose binding protein, and albumin, hepatitis B surface antigen, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Human Leukocyte Antigen (HLA): A genetic designation of the human major histocompatibility complex (MHC). Individual loci are designated by uppercase letters, as in HLA-E, and alleles are designated by numbers, as in HLA-A*0201. The three main MHC class I genes are called HLA-A, HLA-B, and HLA-C. However, there are many genes that encode β2 microglobulin-associated cell surface molecules that are linked to the MHC class I genes. The expression of these genes is variable, both in the tissue distribution and the amount expressed on cells; these genes have been termed the MHC class IB genes.

Immune response: A response of a cell of the immune system, such as a B cell, natural killer cell, or a T cell, to a stimulus. In one embodiment, the response is specific for a particular antigen (an "antigen-specific response"). In one embodiment, an immune response is a T cell response, such as a Th1, Th2, or Th3 response. In another embodiment, an immune response is a response of a suppressor T cell.

Immunogenic peptide: A peptide which comprises an allele-specific motif or other sequence such that the peptide will bind an MHC molecule and induce a T cell response, such as a CD8+ T cell response, or a B cell response (such as antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein and by their ability to stimulate CD4 and/or CD8 when presented in the context of the MHC protein. In one example, an immunogenic "Mtb peptide" is a series of contiguous amino acid residues from the Mtb protein generally between 9 and 20 amino acids in length, such as about 8 to 11 residues in length. Specific immunogenic polypeptides are disclosed herein that are 9 or 10 amino acid residues in length, or at most 12 amino acids in length.

Generally, immunogenic Mtb polypeptides can be used to induce an immune response in a subject, such as a B cell response or a T cell response. In one example, an immunogenic Mtb polypeptide, when bound to a Major Histocompatibility Complex Class I molecule, activates CD8$^+$ T cells, such as cytotoxic T lymphocytes (CTLs) against Mtb. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a CD8$^+$ response against the antigen from which the immunogenic peptide is derived. A CD8$^+$ T cell that specifically recognizes an Mtb polypeptide is activated, proliferates, and/or secretes cytokines in response to that specific polypeptide, and not to other, non-related polypeptides.

Immunogenic composition: A composition comprising an immunogenic Mtb polypeptide or a nucleic acid encoding the immunogenic Mtb polypeptide that induces a measurable T response against Mtb, such as a CD8$^+$ T cell response, or induces a measurable B cell response (such as production of antibodies that specifically bind an Mtb polypeptide). For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. An Mtb polypeptide, or nucleic acid encoding the polypeptide, can be readily tested for its ability to induce a CD8+ T cell response.

Inhibiting or treating a disease: Inhibiting a disease, such as tuberculosis, refers to inhibiting the full development of a disease. In several examples, inhibiting a disease refers to lessening symptoms of a tuberculosis. "Treatment" refers to a therapeutic intervention that ameliorates a sign or symptom of a disease or pathological condition related to the disease, such as tuberculosis.

Interferon gamma (γ): IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells. The production of IFN-γ can be used to assess T cell activation, such as activation of a T cell by an HLA-E presented *Mycobacterium* antigen.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the Mtb epitopes disclosed herein to provide rotational freedom to the linked polypeptide domains and thereby to promote proper domain folding and presentation to the MHC. By way of example, in a recombinant polypeptide comprising two Mtb domains, linker sequences can be provided between them, such as a polypeptide comprising Mtb polypeptide-linker-Mtb polypeptide. Linker sequences, which are generally between 2 and 25 amino acids in length, are well known in the art and include, but are not limited to, the glycine(4)-serine spacer (GGGGS x3) described by Chaudhary et al., *Nature* 339:394-397, 1989.

Lymphocytes: A type of white blood cell that is involved in the immune defenses of the body. There are two main types of lymphocytes: B cells and T cells.

Mammal: This term includes both human and non-human mammals. Similarly, the term "patient" or "subject" includes both human and veterinary subjects.

*Mycobacteria*: A genus of aerobic intracellular bacterial organisms. Upon invasion of a host, these organisms survive within endosomal compartments of monocytes and macrophages. Human mycobacterial diseases include tuberculosis (cause by *M. tuberculosis*), Leprosy (caused by *M. leprae*), Bairnsdale ulcers (caused by *M. ulcerans*), and other infections that can be caused by *M. marinum, M. kansasii, M. scrofulaceum, M. szulgai, M. xenopi, M. fortuitum, M. haemophilum, M. chelonei*, and *M. intracelluare*. *Mycobacterium* strains that were previously considered to be nonpathogenic (such as *M. avium*) are also now known to be major killers of immunosuppressed AIDS patients.

The major response to mycobacteria involves cell mediated hypersensitivity (DTH) reactions with T cells and macrophages playing major roles in the intracellular killing and walling off (or containing) of the organism (granuloma formation). A major T cell response involves CD4+ lymphocytes that recognize mycobacterial heat shock proteins and immunodominant antigens.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

ORF (open reading frame): A series of nucleotide triplets (codons) coding for amino acids without any termination codons. These sequences are usually translatable into a polypeptide.

Peptide Modifications: *Mycobacterium* polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *Mycobacterium* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the polypeptides and nucleic acids described herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation). A "peptide" is a chain of amino acids that is less than 100 amino acids in length. In one embodiment, a "peptide" is a portion of a polypeptide, such as at about 10, 20, 30, 40, 50, or 100 contiguous amino acids of a polypeptide that is greater than 100 amino acids in length.

Portion of a nucleic acid sequence: At least 10, 20, 30 or 40 contiguous nucleotides of the relevant sequence, such as a sequence encoding an antigen. In some instances it would be advantageous to use a portion consisting of 50 or more nucleotides. For instance, when describing a portion of an antigen (such as an antigenic epitope), it may be advantageous to remove a portion of the relevant sequence comprising at least 10, 20, 30, 40 or 50 nucleotides up to a length.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology,* ed. Ausubel et al., Greene Publishing and Wiley-Interscience, New York, 1987 (with periodic updates). PCR primer pairs can be derived from a known sequence, for example, by using computer programs intended for that purpose such as Primer (Version 0.5, © 1991, Whitehead Institute for Biomedical Research, Cambridge, Mass.).

Preventing or treating a disease: "Preventing" a disease refers to inhibiting the full development of a disease, for example in a person who is known to be at risk of infection with *M. tuberculosis*, or *M. leprae*. An example of a person with a known predisposition is someone living with a person diagnosed with tuberculosis, health care professionals, or someone the family, or who has been exposed to *M. tuberculosis*. "Treatment" refers to a therapeutic intervention that ameliorates a sign or symptom of a disease or pathological condition, such as tuberculosis, after it has begun to develop.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified: The term purified does not require absolute purity; rather, it is intended as a relative term. Thus, for example, a purified antigen preparation is one in which the antigen is more pure than the protein in its originating environment within a cell. A preparation of an antigen is typically purified such that the antigen represents at least 50% of the total protein content of the preparation. However, more highly purified preparations may be required for certain applications. For example, for such applications, preparations in which the antigen comprises at least 75% or at least 90% of the total protein content may be employed.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a *Mycobacterium* polypeptide, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of MHC domain polypeptides also retain the biological activity of the native polypeptide. For the purposes of this invention, that activity is conveniently assessed by incorporating the variant domain in the appropriate $\beta 1\alpha 1$ or $\alpha 1\alpha 2$ polypeptide and determining the ability of the resulting polypeptide to inhibit antigen specific T-cell proliferation in vitro, or to induce T suppressor cells or the expression of IL-10 as described in detail below.

Therapeutically active polypeptide: An agent, such as an epitope of Mtb that causes induction of an immune response, as measured by clinical response (for example increase in a population of immune cells, increased cytolytic activity against Mtb, or measurable reduction of a symptom of an infection). Therapeutically active molecules can also be made from nucleic acids. Examples of a nucleic acid based therapeutically active molecule is a nucleic acid sequence that encodes an Mtb epitope, wherein the nucleic acid sequence is operably linked to a control element such as a promoter.

In one embodiment, a therapeutically effective amount of an Mtb polypeptide is an amount used to generate an immune response. In several examples, "treatment" refers to a therapeutic intervention that ameliorates a sign or symptom of tuberculosis.

Therapeutically effective dose: A dose sufficient to prevent advancement, or to cause regression of the disease, or which is capable of relieving symptoms caused by the disease. In one embodiment, a therapeutically effective dose is a dose sufficient to prevent advancement or relieve symptoms of tuberculosis.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tuberculosis (TB): A disease that is generally caused by *Mycobacterium tuberculosis* that usually infects the lungs.

However, other "atypical" mycobacteria such as *M. kansasii* may produce a similar clinical and pathologic appearance of disease.

Transmission of *M. tuberculosis* occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed, and thus tiny, hard capsules are formed. "Primary tuberculosis" is seen disease that develops following an initial infection, usually in children. The initial focus of infection is a small subpleural granuloma accompanied by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or reinfection), particularly when health status declines. The granulomatous inflammation is much more florid and widespread. Typically, the upper lung lobes are most affected, and cavitation can occur. Dissemination of tuberculosis outside of lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject.

Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

TB is a frequent complication of HIV infection. TB infection in subjects infected with a human immunodeficiency virus (HIV) can spread readily and progress rapidly to active disease. Specific symptoms of lung disease due to Mtb infection include chronic cough and spitting blood. Other symptoms of TB disease include fatigue, loss of appetite, weight loss, fever and drenching night sweats.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

*Mycobacterium* Polypeptides

It is disclosed herein that several *Mycobacterium* polypeptides can be used to induce an immune response to Mtb, such as a T cell response. The *Mycobacterium* polypeptides can be used in diagnostic assays to identify subjects infected with a *Mycobacterium* such as Mtb. In several embodiments, the polypeptide comprises or consists of the amino acid sequence set forth as:

```
              (SEQ ID NO: 1, wherein X1 is A or T, X2 is T or
                 A and X3 is any amino acid, such as Q or no
                                                 amino acid)
1. MX1SRFMTDPHAMRDMAGRFEVHAQTVEDEARRMWASAQNISG

AGWSGMAEATSLDTMX2X3MNQAFRNIVNMLHGVRDGLVRDANNY

EQQEQASQQILS, .
```

In several examples, the polypeptide comprises or consists of the amino acid sequence set forth as:

```
                                            (SEQ ID NO: 2)
a. MASRFMTDPHAMRDMAGRFEVHAQTVEDEARRMWASAQNISGA

GWSGMAEATSLDTMTQMNQAFRNIVNMLHGVRDGLVRDANNYEQ

QEQASQQILS (See also TUBERCULIST

No. Rv1038c, as available on Mar. 1, 2007, incorporated herein by reference, known as EsxJ, ES6_2, TB11.0, QILSS).

(SEQ ID NO: 3, TUBERCULIST No. Rv1197, as
        available on Mar. 1, 2007, incorporated herein
        by reference, also know as EsxK, ES6_3, TB11.0,
                                                   QILSS)
b. MASRFMTDPHAMRDMAGRFEVHAQTVEDEARRMWASAQNISG

AGWSGMAEATSLDTMAQMNQAFRNIVNMLHGVRDGLVRDANNYE

QQEQASQQILSS.

(SEQ ID NO: 4, TUBERCULIST No. Rv 1992, as
        available on Mar. 1, 2007, incorporated herein
        by reference, as known as EsxM, TB11.0, QILSS
c. MASRFMTDPHAMRDMAGRFEVHAQTVEDEARRMWASAQNISG

AGWSGMAEATSLDTMT + MNQAFRNIVNMLHGVRDGLVRDANNYE

QQEQASQQILSS.
```

(SEQ ID NO: 5, TUBERCULIST No. Rv 2347c, as
available on Mar. 1, 2007, incorporated herein
by reference, also known as EsxP, ES6_7, QILSS)
d. MATRFMTDPHAMRDMAGRFEVHAQTVEDEARRMWASAQNISG

AGWSGMAEATSLDTMAQMNQAFRNIVNMLHGVRDGLVRDANNYE

QQEQASQQILSS.

(SEQ ID NO: 6, TUBERCULIST No. Rv3620c, as
available on Mar. 1, 2007, incorporated herein
by reference, also known as EsxW, ES6_10,
QILSS)
e. MTSRFMTDPHAMRDMAGRFEVHAQTVEDEARRMWASAQNISG

AGWSGMAEATSLDTMTQMNQAFRNIVNMLHGVRDGLVRDANNYE

QQEQASQQILSS.

In additional embodiments, the polypeptide comprises or consists of the amino acid sequence set forth as:

(SEQ ID NO: 7, TUBERCULIST NO. Rv1088, as
available on Mar. 1, 2007, incorporated herein
by reference, also known as PE9)
2. MSYMIATPAALTAAATDIDGIGSAVSVANAAAVAATTGVLAAGG

DEVLAAIARLFNANAEEYHALSAQVAAFQTLFVRTLTGGCGVFRRR

RGRQCVTAAEHRAAGAGRRQRRRRSGDGQW

RLRQQRHFGCGGQPEFRQHSEHRR.

(SEQ ID NO: 8, TUBERCULIST NO. Rv2487, as
available on Mar. 1, 2007, incorporated
herein by reference, also known as PE_PGRS42)
3. VSLVIATPQLLATAALDLASIGSQVSAANAAAAMPTTEVVAAAA

DEVSAAIAGLFGAHARQYQALSVQVAAFHEQFVQALTAAAGRYAST

EAAVERSLLGAVNAPTEALLGRPLIGNGADGTAPGQPGAAGGLLFG

NGGNGAAGGFGQTGGSGGAAGLIGNGGNGGAGGTGAAGGAGGNG

GWLWGNGGNGGVGGTSVAAGIGGAGGNGGNAGLFGHGGAGGTG

GAGLAGANGVNPTPGPAASTGDSPADVSGIGDQTGGDGGTGGHGTA

GTPTGGTGGDGATATAGSGKATGGAGGDGGTAAAGGGGGNGGDG

GVAQGDIASAFGGDGGNGSDGVAAGSGGGSGGAGGGAFVHIATAT

STGGSGGFGGNGAASAASGADGGAGGAGGNGGAGGLLFGDGGNG

GAGGAGGIGGDGATGGPGGSGGNAGIARFDSPDPEAEPDVVGGKGG

DGGKGGSGLGVGGAGGTGGAGGNGGAGGLLFGNGGNGGNAGAGG

DGGAGVAGGVGGNGGGGGTATFHEDPVAGVWAVGGVGGDGGSG

GSSLGVGGVGGAGGVGGKGGASGMLIGNGGNGGSGGVGGAGGVG

GAGGDGGNGGSGGNASTFGDENSIGGAGGTGGNGGNGANGGNGG

AGGIAGGAGGSGGFLSGAAGVSGADGIGGAGGAGGAG

GAGGSGGEAGAGGLTNGPGSPGVSGTEGMAGAPG (SEQ ID NO: 9, TUBERCULIST No. Rv1860, as
available on Mar. 1, 2007, incorporated herein
by reference, also known as Apa, modD, mpt32)
4. MHQVDPNLTRRKGRLAALAIAAMASASLVTVAVPATANADPEPA

PPVPTTAASPPSTAAAPPAPATPVAPPPPAAANTPNAQPGDPNAAPPP

ADPNAPPPPVIAPNAPQPVRIDNPVGGFSFALPAGWVESDAAHFDYG

SALLSKTTGDPPFPGQPPPVANDTRIVLGRLDQKLYASAEATDSKAA

ARLGSDMGEFYMPYPGTRINQETVSLDANGVSGSASYYEVKFSDPSK

PNGQIWTGVIGSPAANAPDAGPPQRWFVVWLGTANNPVDKGAAKA

LAESIRPLVAPPPAPAPAPAEP APAPAPAGEVAPTPTTPTPQRTLPA (SEQ ID NO: 10, TUBERCULIST NO. Rv1273c, as
available Mar. 1, 2007, incorporated herein
by reference)
5. MLLALLRQHIRPYRRLVAMLMMLQLVSTLASLYLPTVNAAIVDD

GVAKGDTATIVRLGAVMLGVTGLQVLCAIGAVYLGSRTGAFGFGRDL

RSAMFEHIITFSERETARFGAPTLLTRSTNDVRQILFLVQMTATVLVT

APIMCVGGIIMAIHQEAALTWLLLVSVPILAVANYWIISHMLPLFRRM

QSLIDGINRVMRDQLSGVRVVRAFTREGYERDKFAQANTALSNAAL

SAGNWQALMLPVTTLTINASSVALIWFGGLRIDSGQMQVGSLIAFLS

YFAQILMAVLMATMTLAVLPRASVCAERITEVLSTPAALGNPDNPKF

PTDGVTGVVRLAGATFTYPGADCPVLQDISLTARPGTTTAIVGSTGS

GKSTLVSLICRLYDVTAGAVLVDGIDVREYHTERLWSAIGLVPQRSY

LFSGTVADNLRYGGGPDQVVTEQEMWEALRVAAADGFVQTDGLQT

RVAQGGVNFSGGQRQRLAIARAVIRRPAIYVFDDAFSALDVHTDAK

VHASLRQVSGDATIIVVTQRISNAAQADQVIVVDNGKIVGTGTHETL

LADCPTYAEFAASQSLSATVGGVG.

(SEQ ID NO: 11, TUBERCULIST NO. Rv0159c, as
available Mar. 1, 2007, incorporated herein
by reference, also know as PE3 or PE)
6. MSYVIAAPEMLATTAADVDGIGSAIRAASASAAGPTTGLLAAAA

DEVSSAAAALFSEYARECQEVLKQAAAFHGEFTRALAAAGAAYAQ

AEASNTAAMSGTAGSSGALGSVGMLSGNPLTALMMGGTGEPILSDR

VLAIIDSAYIRPIFGPNNPVAQYTPEQWWPFIGNLSLDQSIAQGVTLLN

NGINAELQNGHDVVVFGYSQSAAVATNEIRALMALPPGQAPDPSRL

AFTLIGNINNPNGGVLERYVGLYLPFLDMSFNGATPPDSPYQTYMYT

GQYDGYAHNPQYPLNILSDLNAFMGIRWVHNAYPFTAAEVANAVPL

PTSPGYTGNTHYYMFLTQDLPLLQPIRAIPFVGTPIAELIQPDLRVLVD

LGYGYGYADVPTPASLFAPINPIAVASALATGTVQGPQAALVSIGLLP

QSALPNTYPYLPSANPGLMFNFGQSSVTELSVLSGALGSVARLIPPIA.

(SEQ ID NO: 12, TUBERCULIST No. 3350c, as
available Mar. 1, 2007, herein incorporated
by reference, also known as PPE56 or PPE
7. MEFPVLPPEINSVLMYSGAGSSPLLAAAAAWDGLAEELGSAAVSF

GQVTSGLTAGVWQGAAAAAMAAAAAPYAGWLGSVAAAAEAVAG

QARVVVGVFEAALAATVDPALVAANRARLVALAVSNLLGQNTPAIA

AAEAEYELMWAADVAAMAGYHSGASAAAAALPAFSPPAQALGGG

VGAFLTALFASPAKALSLNAGLGNVGNYNVGLGNVGVFNLGAGNV

GGQNLGFGNAGGTNVGFGNLGNGNVGFGNSGLGAGLAGLGNIGLG

NAGSSNYGFANLGVGNIGFGNTGTNNVGVGLTGNHLTGIGGLNSGT

GNIGLFNSGTGNVGFFNSGTGNFGVFNSGNYNTGVGNAGTASTGLF

NAGNFNTGVVNVGSYNTGSFNAGDTNTGGFNPGGVNTGWLNTGNT

NTGIANSGNVNTGAFISGNFNNGVLWVGDYQGLFGVSAGSSIPAIPIG

-continued

LVLNGDIGPITIQPIPILPTIPLSIHQTVNLGPLVVPDIVIPAFGGGIGI
PINIGPLTITPITLFAQQTFVNQLPFPTFSLGKITIPQIQTFDSNGQLVS
FIGPIVIDTTIPGPTNPQIDLTIRWDTPPITLFPNGISAPDNPLGLLVSV
SISNPGFTIPGFSVPAQPLPLSIDIEGQIDGFSTPPITIDRIPLTVGGGV
TIGPITIQGLHIPAAPGVGNTTTAPSSGFFNSGAGGVSGFGNVGAGSSGW
WNQAPSALLGAGSGVGNVGTLGSGVLNLGSGISGFYNTSVLPFGTPAAVS
GIGNLGQQLSGVSAAGTTLRSMLAGNLGLANVGNFNTGFGNVGDVNL
GAANIGGHNLGLGNVGDGNLGLGNIGHGNLGFANLGLTAGAAGVG
NVGFGNAGINNYGLANMGVGNIGFANTGTGNIGIGLVGDHRTGIGG
LNSGIGNIGLFNSGTGNVGFFNSGTGNFGIGNSGRFNTGIGNSGTAST
GLFNAGSFSTGIANTGDYNTGSFNAGDTNTGGFNPGGINTGWFNTGH
ANTGLANAGTFGTGAFMTGDYSNGLLWRGGYEGLVGVRVGPTISQF
PVTVHAIGGVGPLHVAPVPVPAVHVEITDATVGLGPFTVPPISIPSLP
IASITGSVDLAANTISPIRALDPLAGSIGLFLEPFRLSDPFITIDAFQVV
AGVLFLENIIVPGLTVSGQILVTPTPIPLTLNLDTTPWTLFPNGFTIPAQ
TPVTVGMEVANDGFTFFPGGLTFPRASAGVTGLSVGLDAFTLLPDGFT
LDTVPATFDGTILIGDIPIPIIDVPAVPGFGNTTTAPSSGFFNTGGGGGS

GFANVGAGTSGWWNQGHDVLAGAGSGVANAGTLSSGVLNVGS

GISGWYNTSTLGAGTPAVVSGIGNLGQQLSGFLANGTVLNRSPIVNIG

WADVGAFNTGLGNVGDLNWGAANIGAQNLGLGNLGSGNVGFGNIG

AGNVGFANSGPAVGLAGLGNVGLSNAGSNNWGLANLGVGNIGLAN

TGTGNIGIGLVGDYQTGIGGLNSGSGNIGLFNSGTGNVGFFNTGTGNF

GLFNSGSFNTGIGNSGTGSTGLFNAGNFNTGIANPGSYNTGSFNVGDT

NTGGFNPGDINTGWFNTGIMNTGTRNTGALMSGTDSNGMLWRGDH

EGLFGLSYGITIPQFPIRITTTGGIGPIVIPDTTILPPLHLQITGDADYS

FTVPDIPIPAIHIGINGVVTVGFTAPEATLLSALKNNGSFISFGPITLSN

IDIPPMDFTLGLPVLGPITGQLGPIHLEPIVVAGIGVPLEIEPIPLDAIS

LSESIPIRIPVDIPASVIDGISMSEVVPIDASVDIPAVTITGTTISAIPL

GFDIRTSAGPLNIPIIDIPAAPGFGNSTQMPSSGFFNTGAGGGSGIGNLG

AGVSGLLNQAGAGSLVGTLSGLGNAGTLASGVLNSGTAISGLFNVSTLDA

TTPAVISGFSNLGDHMSGVSIDGLIAILTFPPAESVFDQIIDAAIAELQH

LDIGNALALGNVGGVNLGLANVGEFNLGAGNVGNINVGAGNLGGSNLGL

GNVGTGNLGFGNIGAGNFGFGNAGLTAGAGGLGNVGLGNAGS

GSWGLANVGVGNIGLANTGTGNIGIGLTGDYRTGIGGLNSGTGNLGL

FNSGTGNIGFFNTGTGNFGLFNSGSYSTGVGNAGTASTGLFNAGNFN

TGLANAGSYNTGSLNVGSFNTGGVNPGTVNTGWFNTGHTNTGLFNT

GNVNTGAFNSGSFNNGALWTGDYHGLVGFSFSIDIAGSTLLDLNETL

NLGPIHIEQIDIPGMSLFDVHEIVEIGPFTIPQVDVPAIPLEIHESIHMD

PIVLVPATTIPAQTRTIPLDIPASPGSTMTLPLISMRFEGEDWILGSTAA

IPNFGDPFPAPTQGITIHTGPGPGTTGELKISIPGFEIPQIATTRFLLDV

NISGGLPAFTLFAGGLTIPTNAIPLTIDASGALDPITIFPGGYTIDPLPL

-continued

HLALNLTVPDSSIPIIDVPPTPGFGNTTATPSSGFFNSGAGGVSGFGNVG

SNLSGWWNQAASALAGSGSGVLNVGTLGSGVLNVGSGVSGIYN

TSVLPLGTPAVLSGLGNVGHQLSGVSAAGTALNQIPILNIGLADVGNF

NVGFGNVGDVNLGAANLGAQNLGLGNVGTGNLGFANVGHGNIGFG

NSGLTAGAAGLGNTGFGNAGSANYGFANQGVRNIGLANTGTGNIGI

GLVGDNLTGIGGLNSGAGNIGLFNSGTGNIGFFNSGTGNFGIGNSGSF

NTGIGNSGTGSTGLFNAGSFNTGVANAGSYNTGSFNAGDTNTGGFNP

GTINTGWFNTGHTNTGIANSGNVGTGAFMSGNFSNGLLWRGDHEGL

FSLFYSLDVPRITIVDAHLDGGFGPVVLPPIPVPAVNAHLTGNVAMGA

FTIPQIDIPALTPNITGSAAFRIVVGSVRIPPVSVIVEQIINASVGAEMR

IDPFEMWTQGTNGLGITFYSFGSADGSPYATGPLVFGAGTSD

GSHLTISASSGAFTTPQLETGPITLGFQVPGSVNAITLFPGGLTFPATSL

LNLDVTAGAGGVDIPAITWPEIAASADGSVYVLASSIPLINIPPTPGIG

NSTITPSSGFFNAGAGGGSGFGNFGAGTSGWWNQAHTALAGAGSGF

ANVGTLHSGVLNLGSGVSGIYNTSTLGVGTPALVSGLGNVGHQLSG

LLSGGSAVNPVTVLNIGLANVGSHNAGFGNVGEVNLGAANLGAHNL

GFGNIGAGNLGFGNIGHGNVGVGNSGLTAGVPGLGNVGLGNAGGN

NWGLANVGVGNIGLANTGTGNIGIGLTGDYQTGIGGLNSGAGNLGL

FNSGAGNVGFFNTGTGNFGLFNSGSFNTGVGNSGTGSTGLFNAGSFN

TGVANAGSYNTGSFNVGDTNTGGFNPGSINTGWLNAGNANTGVAN

AGNVNTGAFVTGNFSNGILWRGDYQGLAGFAVGYTLPLFPAVGAD

VSGGIGPITVLPPIHIPPIPVGFAAVGGIGPIAIPDISVPSIHLGLDPAV

HVGSITVNPITVRTPPVLVSYSQGAVTSTSGPTSEIWVKPSFFPGIRIAP

SSGGGATSTQGAYFVGPISIPSGTVTFPGFTIPLDPIDIGLPVSLTIPGF

TIPGGTLIPTLPLGLALSNGIPPVDIPAIVLDRILLDLHADTTIGPINVP

IAGFGGAPGFGNSTTLPSSGFFNTGAGGGSGFSNTGAGMSGLLNAMSDPL

LGSASGFANFGTQLSGILNRGAGISGVYNTGALGVVTAAVVSGFGNV

GQQLSGLLFTGVGP.

In a second embodiment, an Mtb polypeptide of use in the methods disclosed herein has a sequence at least 75%, 85%, 90%, 95%, 96%, 97%, 98% or 99% homologous to the amino acid sequence set forth in one of SEQ ID NOs: 1-12. For example, the polypeptide can have an amino acid sequence, at least 85%, 90%, 95%, 96%, 97%, 98% or 99% homologous to one of the amino acid sequences set forth in SEQ ID NOs: 1-12. Exemplary sequences can be obtained using computer programs that are readily available on the internet and the amino acid sequences set forth herein. In one example, the polypeptide retains a function of the Mtb protein, such as binding to an antibody that specifically binds the Mtb epitope.

Minor modifications of an Mtb polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of an Mtb polypeptide is a conservative variant of the Mtb polypeptide. A table of conservative substitutions is provided herein. Substitutions of the amino acids sequence shown in SEQ ID NOs: 1-12 can be made based on this table.

Mtb polypeptides are disclosed herein that can be used to detect an immune response to Mtb. These peptides include or consist of at least nine amino acids, such as nine to twenty amino acids consecutive amino acids of an Mtb polypeptide set forth above. Specific, non-limiting examples are twelve, eleven, ten amino acids, or nine consecutive amino acids of one of the Mtb polypeptides set forth above. In these examples, the Mtb polypeptide does not include the full-length amino acid sequences set forth as SEQ ID NOs: 1-12.

An isolated polypeptide is disclosed that includes nine to twelve consecutive amino acids from an Mtb polypeptide, wherein the isolated polypeptide comprises the amino acid sequence set forth as QTVEDEARRMW (SEQ ID NO: 13). In some embodiments, the polypeptide is nine, ten or eleven amino acids in length. In additional embodiments, the polypeptide consists of the amino acid sequence set forth as SEQ ID NO: 13. An isolated polypeptide is disclosed that includes nine to twelve consecutive amino acids from an Mtb polypeptide, wherein the isolated polypeptide comprises the amino acid sequence set forth as VSAAIAGLF (SEQ ID NO: 14). In some embodiments, the polypeptide is nine, ten or eleven amino acids in length. In additional embodiments, the polypeptide consists of the amino acid sequence set forth as SEQ ID NO: 14.

In several embodiments, the isolated Mtb polypeptide is included in a fusion protein. Thus, the fusion protein can include the Mtb polypeptide (see above) and a second heterologous moiety, such as a myc protein, an enzyme or a carrier (such as a hepatitis carrier protein or bovine serum albumin) covalently linked to the Mtb polypeptide. In several examples, a polypeptide consisting of nine to twelve amino acids of one of the amino acid sequences set forth as SEQ ID NOs: 1-14 that bind MHC class I is covalently linked to a carrier. In additional example, a polypeptide consisting of one of the amino acid sequences set forth as one of SEQ ID NOs: 1-14 is covalently linked to a carrier.

In additional examples, the polypeptide can be a fusion protein and can also include heterologous sequences to Mtb (such as amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. In additional embodiments, the protein consists of the Mtb polypeptide.

The polypeptide can optionally include repetitions of one or more of the Mtb polypeptides disclosed herein. In one specific, non-limiting example, the polypeptide includes two, three, four, five, or up to ten repetitions of one of the Mtb polypeptides described above. Alternatively, more than one polypeptide can be included in a fusion polypeptide. Thus, in several examples, the polypeptide can include at least two, at least three, at least four, at least five or at least six of the amino acid sequences set forth as SEQ ID NOs: 1-14. A linker sequence can optionally be included between the Mtb polypeptides.

The Mtb polypeptides disclosed herein can be chemically synthesized by standard methods, or can be produced recombinantly. An exemplary process for polypeptide production is described in Lu et al., *Federation of European Biochemical Societies Letters*. 429:31-35, 1998. They can also be isolated by methods including preparative chromatography and immunological separations.

If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding Mtb or an epitope thereof into an expression vector, introducing the expression vector into a host cell, and isolating the polypeptide (see below).

Polynucleotides encoding the Mtb polypeptides disclosed herein are also provided. Exemplary nucleic acid sequences are set forth below:

```
ESXJ (ESAT-6 LIKE PROTEIN 2)
                                              (SEQ ID NO: 15)
atggcctcgcgttttatgacggatccgcacgcgatgcgggacatggcgggccgttttgag gtgcacgcccagacggtggaggacgaggctcgccggatgtgggcgtccgcgcaaaacatc tcgggcgcgggctggagtggcatggccgaggcgacctcgctagacaccatgacccagatg aatcaggcgtttcgcaacatcgtgaacatgctgcacggggtgcgtgacgggctggttcgc gacgccaacaactacgaacagcaagagcaggcctcccagcagatcctcagcagctga ESXK (ESAT-6 LIKE PROTEIN 3)
                                              (SEQ ID NO: 16)
atggcctcacgttttatgacggatccgcacgcgatgcgggacatggcgggccgttttgag gtgcacgcccagacggtggaggacgaggctcgccggatgtgggcgtccgcgcaaaacatt tccggtgcgggctggagtggcatggccgaggcgacctcgctagacaccatggcccagatg aatcaggcgtttcgcaacatcgtgaacatgctgcacggggtgcgtgacgggctggttcgc gacgccaacaactacgagcagcaagagcaggcctcccagcagatcctcagcagctaa ESXM (ESAT-6 LIKE PROTEIN ESXM)
                                              (SEQ ID NO: 17)
atggcctcacgttttatgacggatccgcatgcgatgcgggacatggcgggccgttttgag gtgcacgcccagacggtggaggacgaggctcgccggatgtgggcgtccgcgcaaaacatt tccggtgcgggctggagtggcatggccgaggcgacctcgctagacaccatgacctagatg
```

-continued

```
aatcaggcgtttcgcaacatcgtgaacatgctgcacggggtgcgtgacgggctggttcgc gacgccaacaactacgaacagcaagagcaggcctcccagcagatcctgagcagctag
```

ESXP (ESAT-6 LIKE PROTEIN 7)

(SEQ ID NO: 18)
```
atggcaacacgttttatgacggatccgcacgcgatgcgggacatggcgggccgttttgag gtgcacgcccagacggtggaggacgaggctcgccggatgtgggcgtccgcgcaaaacatc tcgggcgcgggctggagtggcatggccgaggcgacctcgctagacaccatggcccagatg aatcaggcgtttcgcaacatcgtgaacatgctgcacggggtgcgtgacgggctggttcgc gacgccaacaactacgagcagcaagagcaggcctcccagcagatcctcagcagctaa
```

ESXW (ESAT-6 LIKE PROTEIN 10)

(SEQ ID NO: 19)
```
atgacctcgcgttttatgacggatccgcacgcgatgcgggacatggcgggccgttttgag gtgcacgcccagacggtggaggacgaggctcgccggatgtgggcgtccgcgcaaaacatt tccggcgcgggctggagtggcatggccgaggcgacctcgctagacaccatgacccagatg aatcaggcgtttcgcaacatcgtgaacatgctgcacggggtgcgtgacgggctggttcgc gacgccaacaactacgaacagcaagagcaggcctcccagcagatcctcagcagctga
```

PE9 (PE FAMILY PROTEIN)

(SEQ ID NO: 20)
```
atgtcatacatgattgccacaccagcggcgttgacggcggcggcaacggatatcgacggg attggctcggcggttagcgttgcgaacgccgcggcggtcgccgcgacaaccggagtgctg gccgccggtggcgatgaagtgttggcggccatcgctaggctgttcaacgcaaacgccgag gaatatcacgccctcagcgcgcaggtggcggcgtttcaaaccctgtttgtgcgcaccttg actgggggtgcggagtctttcgccggcgccgaggccgccaatgcgtcacagctgcagag catcgcgcggcaggtgcggggcgccgtcaacgccgtcgccggtcaggtgacgggcaatgg cggctccggcaacagcggcacttcggctgcggcggccaacccgaattccgacaacacagc Gagcatcgccgatag
```

PE_PGRS42 (PE-PGRS FAMILY PROTEIN)

(SEQ ID NO: 21)
```
gtgtcgttggtgatcgcgacgccgcagctgctggcaactgcggctttggatttagcgagt attggttcgcaggtgagcgcggctaatgcggccgcgggcgatgccgacgacggaagtggtg gctgcggctgccgatgaagtgtcggcggcgattgcggggttgttcggggcccatgctcgg cagtatcaggcgctcagcgtacaggtggcagcgtttcacgagcagtttgtgcaggcgttg actcggccgcgggtcggtatgccagcactgaggccgctgttgagcggagtctgctgggt gcggtgaatgcgcccaccgaggcgcttttggggcgcccgttgatcggaaacggcgccgac gggacggcacccgggcagcctggcgcggccggcgggttgctgtttggcaacggtggcaac ggcgcggctggcgggttcggtcaaaccggcggcagcggaggcgcggccgggttgatcggc aacggcggcaacggcggggccggtggtaccggcgcggccggcggtgccggtgggaacggg gggtggttgtggggcaacggcggcaacggcggtgtcggcggcaccagcgtggccgcaggc atcggggtgcggcggtaacggcggcaacgccgggctgttcggccatggcggcgccggt ggtaccggcggcgccggcctcgccggggcaaacggggtcaatcccacgcccggccccgcg gccagcaccggggacagcccggcagatgtgtccggcatcggtgatcaaaccggcggcgac ggcggcacgggcggccatggcactgccggcacgccgaccggtggcaccggcggcgacggt gccaccgcgacggcaggctcgggcaaggccaccggcggtgccggtggtgacggcggtacc gccgctgccggtggcggcggcggcaacggcggcgacggcggagtcgcgcagggcgacatt
```

-continued gcgagcgcctttggcggtgatggtggcaacgggtccgacggtgtagccgccggcagtggg ggtggtagcggcggcgccgaggcggcgctttcgtacacatcgccactgccacctctacc ggtggtagcggcggtttcggtggtaacggggctgccagtgccgcctccggcgccgacggt ggcgcaggggagctggcggcaatggtggcgccggcgggttgctattcggtgatggcggc aacggtggcgccggtggcgcgggtggtatcggtggtgacggcgccacgggggggcccggg ggaagcggcggcaacgctggcatcgcgaggtttgacagcccagaccccgaggcagaaccc gatgtggtcggcggcaagggtggtgatggcggcaagggcggcagcggccttggcgtcggc ggcgccggcgggaccggcggcgcgggcggcaacggcggcgccggcgggttgttgttcggc aacggcggcaacggcggcaacgccggggccggcggggatggcggcgccggcgttgccggt ggggttggcggtaacgcggccggtggtggcaccgcgacgtttcacgaagacccggtcgct ggtgtctgggcggtcggtggcgtaggtggtgatggtggctccggcggcagctcgcttggt gtcggcggggtgggcggagccggtggcgtgggtggcaagggtggcgccagcggcatgttg atcggcaacggcggcaacggtggcagcggcggagtcggtggggccggtggagtcggcggg gctggcggtgacggcggcaacggcggctccggtggcaacgccagtacttttggcgatgag aactccatcggcggggccggcgggacgggcggcaacggggcaacggcgcaaacggcggt aacggtggcgctggcggtattgccggcggtgcgggtgggtccggagggttcctcagcggt gccgcaggagtcagcggcgctgacggtatcggtggcgcgggcggcgcaggcggtgccggt ggcgcgggcggtagcggcggtgaggcaggcgcggggggcctcaccaacggccccgggtcc cctggcgtttccggcaccgaaggcatggccggcgcgcccggctag Rv1860 (FIBRONECTIN ATTACHMENT PROTEIN)

(SEQ ID NO: 22)
atgcatcaggtggaccccaacttgacacgtcgcaagggacgattggcggcactggctatc gcggcgatggccagcgccagcctggtgaccgttgcggtgcccgcgaccgccaacgccgat ccggagccagcgccccccggtacccacaacggccgcctcgccgccgtcgaccgctgcagcg ccacccgcaccggcgacacctgttgcccccccaccaccggccgccgccaacacgccgaat gcccagccgggcgatcccaacgcagcacctccgccggccgacccgaacgcaccgccgcca cctgtcattgccccaaacgcaccccaacctgtccggatcgacaacccggttggaggattc agcttcgcgctgcctgctggctgggtggagtctgacgccgcccacttcgactacggttca gcactcctcagcaaaaccaccggggacccgccatttccggacagccgccgccggtggcc aatgacacccgtatcgtgctcggccggctagaccaaaaagctttacgccagccgccgaagcc accgactccaaggccgcggcccggttgggctcggacatgggtgagttctatatgccctac ccgggcacccggatcaaccaggaaaccgtctcgctcgacgccaacggggtgtctggaagc gcgtcgtattacgaagtcaagttcagcgatccgagtaagccgaacggccagatctggacg ggcgtaatcggctcgcccgcggcgaacgcaccggacgccgggcccctcagcgctggttt gtggtatggctcgggaccgccaacaacccggtggacaagggcgcggccaaggcgctggcc gaatcgatccggcctttggtcgccccgccgccggcgccggcaccggctcctgcagagccc gctccggcgccggcgccggccggggaagtcgctcctaccccgacgacaccgacaccgcag Cggaccttaccggcctga RV1273C (PROBABLE DRUGS-TRANSPORT TRANSMEMBRANE ATP-BINDING
PROTEIN ABC TRANSPORTER)

(SEQ ID NO: 23)
atgctcctggccctgctgcgccagcacatccgaccgtaccgccggctggtcgcgatgctg atgatgctgcagctggtcagcacccctggcttcgctataccctcccgacggtcaacgccgca -continued

```
atcgtcgacgacggcgtcgccaagggcgacaccgccaccatcgtacggctgggtgcggtg atgcttggggtgaccggattgcaggtgctgtgcgcgatcggggcggtctatctgggctcc cggaccggggcgggtttcggccgtgacctgcgctcggcaatgttcgaacacatcatcacc ttctcggaacgcgagaccgcccgattcggcgctccgacgttgttgacccgcagcaccaac gacgtccggcagatcctgttcctggtccagatgaccgccaccgtgctggtcaccgcaccg atcatgtgcgtcggcggaatcatcatggccatccaccaggaggccgcgctgacatggctg ctgctggtcagcgttccgattctggccgtagcaaactactggatcatctcccacatgctg ccgctcttccgccgcatgcagagcctgatcgacggcatcaacccgggtgatgcgcgatcag ctgtccggggtgcgagtggtccgcgccttcacccgcgaaggctatgaacgcgacaagttc gcgcaggccaatacggcgctgtcgaatgccgcactgagcgccggcaactggcaagcactg atgctgccggtgaccacgctgaccatcaacgcatccagcgtcgcactgatctggttcggt gggctacgcatcgacagcggccagatgcaggtcggctccctgatcgccttcctgtcctac ttcgcccagatcctgatggcggtgttgatggcgaccatgacgctggccgtgctgccacga gcgtcggtctgcgccaacgcatcaccgaggtgcttttccacgcccgccgcactcggtaac cccgacaatcccaagttcccgacgacggggtcacgggcgtagtgcgcttggctggcgca acctttacctatcctggcgccgactgcccggtgctgcaggacatttcgttgactgcgcgg cccggtaccaccaccgcgatcgtcggcagtaccggttcgggcaagtcgacactggtgtcg ttgatctgccggctctacgacgtcaccgctggcgcggtcttggttgacggtatcgacgtc cgcgagtaccacaccgagcggctctggtcagcgatcgggctggtgccccagcgcagctac ctcttctccggaaccgtcgcggacaacctgcgctacggcggggccagaccaggtagtc accgagcaggagatgtgggaggcgctgcgggtcgccgcggccgacggctttgtacaaaca gacgggctgcagacgcgtgtcgcccaaggtggtgtcaacttctccggcgggcagcgccaa cggctggcgatagcccgagcggtcatccgacgtccggccatctatgtgttcgacgacgcg ttctccgcacttgacgtgcacaccgacgccaaagtccacgcatcgctgcgacaggtatct ggtgatgcaaccatcattgttgttacacaacggatttcgaatgccgctcaggccgaccag gtcatcgttgtcgataacggtaagatcgtcggcacgggcacccacgaaacgctgctggcc gattgccccacctatgccgaattcgccgcctcacaatcgctgagcgccacggtcggggt Gtagggtga
```

RV0159C (PE FAMILY PROTEIN)
(SEQ ID NO: 24)

```
atgtcctacgtcatcgcggccccggagatgttggcaacgacggccgcggacgtggacggg atcggttcggcgatacgagcggccagcgcgtccgctgcgggtccaacgaccggactgctg gccgcggccgccgatgaggtgtcgtcggccgctgcagcgctgttcagcgaatacgcgcgc gaatgtcaagaggtcctaaagcaggctgcggcgttccatggcgagttcacccgggcgctg gctgccgccggggccgcctatgcccaggctgaagccagcaacaccgctgctatgtcgggc accgccgggtccagcggcgccctcggttctgtcgggatgctgtcaggcaacccgctaacc gcgttgatgatgggcggcaccggggaaccgatccttagtgaccgcgtcttggcgatcatt gacagcgcatacattcggcccattttcgggcccaacaacccggtcgcccagtacacgccc gagcagtggtggccgtttatcgggaacctgtcactggaccaatccatcgcccagggtgtc acgctgctgaacaacggcatcaacgcggaactacaaaatgggcatgacgtcgtcgttttc ggctactcgcaaagcgccgcggtagcgaccaatgaaatacgcgctcttatggcgttacca ccgggccaagccccagatccaagccggctggctttcacgttgatcggtaatatcaataac
```

-continued cccaacggcggcgtcctcgagcgttacgtgggcctttacctcccgttcttggatatgtcg ttcaacggtgcgactccaccggattcccctaccagacctacatgtacaccggccaatac gacggctacgcccacaacccgcagtacccgctcaataccttgtcggacctcaacgccttc atgggcatcagatgggtgcacaacgcgtaccccttcaccgcggccgaggttgccaatgcc gtgccgttgcccacgtctccgggctacaccggcaacacccattactacatgtttctgacc caggacctgccgctgttgcagccgattcgcgccatcccttcgtagggaccccaatagcc gagctgattcagcccgacctacgggtgctagtcgacttgggctatggctacggctacgcc gacgtacccaccccggccagcctgttcgcgccaatcaacccgatcgccgtggcctcggcc ctggcgaccgggaccgtgcaaggcccccaagccgccctagtaagcatcggattgttaccg cagtccgcgctacccaatacgtatccgtatcttccgtcggcgaatccgggcctgatgttc aacttcggtcaatccagtgtgacggagttgtcggtgctcagtggcgccctcgggtccgta gcgagattgattccaccgatcgcgtga Rv3350c (PPE FAMILY PROTEIN) (SEQ ID NO: 26)

atggagtttccggtgttgccaccggaaatcaactccgtgctgatgtattcggtgcgggg tcgagcccgttgctggcggcggccgcggcgtgggatgggctggctgaggagttggggtcg gcggcggtgtcgtttgggcaggtgacgtcgggcctgacggcgggggtgtggcagggtgcg gcggcggcggcgatggcggccgcggcggcgccgtatgcggggtggttgggttcggtggcg gccgcggccgaggcggtggccgggcaggcgcgggtggtggtgggggtctttgaggcggcg ttggcggcgacggtggatccggcgctggtggcggccaaccgggcgcggctggtggcgttg gcggtgtcgaatctgttggggcagaacacgccggcgatcgcggccgccgaggccgagtac gagctgatgtgggccgccgatgtggcggcgatggccggctaccattccggcgcgtcggct gctgccgcggcgttgccggcgttcagcccaccggcgcaggcgctggggggaggtgtcggc gcgttccttaccgccctgttcgccagccctgcgaaggcgctgagcctgaatgcgggttcg ggcaatgtcggcaattacaacgtcgggttgggcaatgtcggggtgttcaacctgggcgcg ggcaatgtgggtgggcagaatctgggtttcgggaatgccggtggcaccaatgtcgggttc ggcaacctcggtaacgggaatgtcgggttcggcaactccggtctgggggcgggcctggcc ggcttgggcaatatcgggttggcaatgcgggcagcagcaactatggtttcgcaaacctg ggtgtgggcaacatcggtttcggcaacaccggcaccaacaacgtcggcgtcgggctcacc ggcaaccacctgacgggtatcgggggcctgaattcgggcaccggaatatcggggttgttc aactccggcaccgggaatgtggggttcttcaattcggggaccgggaacttcggggtgttc aactcgggtaattacaacaccggtgtcggtaatgcggggacggccagcacggggttgttc aatgccggcaatttcaacaccggcgtggtgaacgtgggcagttacaacaccggcagtttc aacgccggcgacaccaacaccggtggcttcaaccccggcggtgtgaacaccggctggctg aacaccggcaacaccaacaccggcatcgccaactcgggcaacgtcaacaccggcgcgttc atctcgggcaacttcaacaacggcgtgctgtgggtgggtgactaccagggcctgttcggc gtctccgccggctcgtcgatccccgcaattcccatcggcctggtgctcaacggcgacacc ggcccgatcaccatccagcccatcccgatcctgcccaccatcccgctcagcattcaccaa accgtcaacttgggcccgctggtggttcccgacatcgtgatccccgccttcggcggcggt atcggcatacccatcaacatcggcccgctgaccatcacacccatcaccctgtttgcccaa cagacatttgtcaaccaattgccctttcccaccttcagtttagggaaaatcacaattcca -continued

```
caaatccaaacctttgattctaacggtcagcttgtcagctttatcggccctatcgttatc gacaccaccattcccggacccaccaatccacagattgatttaacgatcagatgggatacc cctccgatcacgctgttcccgaatggcatcagtgctcccgataatcctttggggttgctg gtgagtgtgtcgatcagtaacccgggctttaccatcccgggatttagtgttcccgcgcag ccgttgccgttgtcgatcgatatcgagggccagatcgacgggttcagcaccccgccgatc acgatcgatcgcatcccctgaccgtgggggcggggtcacgatcggccccatcacgatc cagggccttcatatcccggcggcgccgggagtggggaacaccaccacggccccgtcgtcg ggattcttcaactccggtgcggtggggtgtcgggtttcggcaacgtcggcgcgggcagc tcgggctggtggaaccaggcgccgagcgcgctgttggggccggttcgggtgttggcaac gtgggcaccctgggctcggtgtgctcaacctgggctcagggatctcggggttctacaac accagcgtgttgcctttcgggacaccggcggcggtgtcgggcatcggcaacctgggccag cagctgtcgggggtgtcggcggcgggaaccacgctgcgctcgatgctcgccggcaacctc gggttggccaatgtgggcaacctcaacaccgggttcggaaatgtcggggacgtcaacctg ggtgcggcaacatcggtgggcacaacctgggcctgggcaatgtcggggacggcaacctg gggttggcaacatcggccatggcaacctggggtttgccaacttgggcctgaccgccggc gcggcggggtgggcaacgttggttttggcaatgccggcatcaacaactatggcttggcg aacatgggtgtgggcaatattgggtttgccaacaccggcacgggcaacatcgggatcggg ctggtcggggaccatcggaccgggatcgggggcttgaactccggcatcggcaatatcggg ttgttcaactccggcaccggcaacgtcgggttcttcaattccgggaccggcaacttcggc atcgggaactccggccgcttcaacaccgggatcggtaatagcggaacggccagcaccggg ctcttcaatgccggcagcttcagcaccggcatcgccaacactggtgactacaacacgggc agcttcaacgccggcgacaccaacaccggtggcttcaacccgggcggcatcaacaccggc tggttcaacaccgggcatgccaacaccgggttggccaacgcgggcaccttcggcaccggc gccttcatgacgggcgactacagcaacggcctgttgtggcggggcggctacgagggcctg gtcggcgtccgcgtcgggcccacgatctcccaattcccggtcaccgtgcacgcgatcggc ggggtgggcccgctgcatgtggcgcccgtcccggtacccgccgtgcacgtcgagatcacc gacgccaccgtcggcctgggtccgttcaccgtcccaccgatcagcattccctcacttccc atcgccagcatcaccggaagcgtggacctggccgcaaacaccatctcgccgattcgcgct cttgacccgctcgccggttcgatagggcttttttctcgagccgttccgcctcagtgaccca tttatcaccattgatgcgttccaagttgttgccggtgtcttgttcctagagaacatcatt gtgcccggcctcacggttagcggtcagatattggtcaccccgacaccaattcccctaacc ctcaacttggacaccaccccgtggacgcttttcccgaatggtttcaccattcccgcgcaa accccgtgacggtgggtatggaggtcgccaacgacgggttcaccttcttcccgggtggg ctgacctttccgcgggcctccgccggggtcaccggactgtccgtggggctggacgcgttc acgctgttgcccgacgggttcaccctcgacaccgtgccggcgaccttcgacggcaccatc ctcatcggcgatatcccgatcccgatcatcgatgtgccggcggtgccggggttcggcaac accaccacggcccccatcgtcggggttcttcaacaccggcggcggcggtggatcggggtcc gccaacgtcggcgcgggcacgtcgggctggtggaaccaggggcacgacgtgctagcaggg gcgggctcgggagttgccaatgccggcacgctgagctcgggcgtgctgaacgtcggctcg gggatctccgggtggtacaacaccagcaccctgggagcgggcaccccggcggtggtctcg ggcatcggcaacctcggccagcagctgtcgggggttcttggcaaatgggaccgtgctcaac
```

-continued

```
cggagccccattgtcaatatcgggtgggccgatgtgggcgcgttcaacaccgggttgggc aatgtggggacctcaactggggtgcggccaacatcggcgcgcagaacctgggcctgggc aatctcggcagcgggaacgtcgggttcggcaacatcggtgccggcaacgtcgggttcgcc aactcgggtccggcggtgggcctggccggcctgggcaacgtggggttgagcaatgccggc agcaacaactggggctggccaacctgggtgtgggcaacatcggttggccaacaccggc acgggcaacatcgggatcgggctggtcggcgactaccagaccggcatcggcggcctcaac tcgggtagtggcaatatcggactgttcaactccggcaccggcaatgtcgggttcttcaac accggcaccggcaacttcggactgttcaactccggtagtttcaacaccggcatcggtaat agcggaaccggcagtactgggctcttcaatgccggcaatttcaacaccggcatcgccaac cccgggtcgtacaacacgggcagcttcaatgtcggtgataccaacaccggtggtttcaac ccgggcgacatcaacaccggctggttcaacaccggcattatgaatacgggcacccgcaac accggcgccctcatgtcggggaccgacagcaacggcatgctgtggcgcggcgaccacgag ggcctgttcggcctgtcctatggcatcacgatcccgcaattcccgatccgcatcaccacg actggcggtatcggccccatcgtcatcccggacaccacgatccttccgccgctgcacctg cagatcaccggcgacgcggactacagcttcaccgtgcccgacatccccatccccgccatc cacatcggcatcaatggcgtcaccgtcggcttcaccgccccggaagccaccctgctg tccgccctgaagaataacggtagcttcatcagcttcggccccatcacgctctcgaatatc gatattccgcccatggatttcacgttaggcctgcccgttcttggtcctatcacgggccaa ctcggaccaattcatcttgagccaatcgtggtggccgggatcggtgtgcccctggagatc gagcccatcccctggatgcgatttcgttgagtgagtcgattcctatccgcatacctgtt gatattccggcctcggtcatcgatgggatttcaatgtcggaagtggtgccgatcgatgcg tccgtggacatcccggcggtcacgatcacaggcaccaccatttccgcgatcccgctgggc ttcgacattcgcaccagtgccggacccctcaacatcccgatcatcgacatcccggcggcg ccgggcttcgggaactcgacccagatgccgtcgtcggggttcttcaacaccggtgccggc ggcggatcgggcatcggcaacttgggtgcgggcgtgtcgggcctgctcaaccaggccggc gcggggtcactggtggggacactctcggggctgggcaatgccggcaccctggcctcgggt gtgctgaactccggcaccgccatctccgggctgttcaacgtgagcacgctggacgccacc accccggcggtgatctcggggttcagcaacctcggcgaccatatgtcgggggtgtccatc gatgccctgatcgcgatcctcaccttcccacctgccgagtccgtgttcgatcagatcatc gacgcggccatcgccgagctgcagcacctcgacatcggcaacgctttggccttgggcaat gtcggcggggtgaacctcggtttggctaacgtcggtgagttcaacctgggtgcgggcaac gtcggcaacatcaacgtcggcgccggcaacctcggcggcagcaacttggggttgggcaac gtcgggaccggcaacctcgggttcggcaacatcggtgccggcaatttcggactcggcaac gcgggcctgaccgcgggcgcgggggggcctgggcaatgtggggttgggtaacgccggcagc ggcagctgggggttggccaacgtgggtgtgggcaatatcgggttggccaacaccggcacc ggcaacatcgggatcgggctgaccggggactatcggaccgggatcggcggcctgaactcg ggcaccgggaacctcgggttgttcaactcgggcaccggcaacatcgggttcttcaacacc gggaccgggaacttcgggctgttcaactcgggcagttacagcaccggtgtgggggaatgcg ggcacggccagcaccggggttgttcaacgcggggaacttcaacaccggtctggccaatgcc ggctcctacaacaccggcagcctcaacgtgggcagcttcaacaccggcggcgtcaacccg
```

-continued

```
ggcaccgtcaacaccggctggttcaacaccggccacaccaacaccggcctgctcaacacc
ggcaacgtcaacaccggcgcgttcaactccggcagcttcaacaacggggcgctgtggacc
ggtgactaccacgggctggtcggcttctccttcagcatcgacatcgccggcagcaccctg
ctggacctcaacgaaaccctcaacctgggccccatccacatcgagcagatcgacatcccc
ggcatgtcgctgttcgacgtccacgaaatcgtcgagatcggaccgttcaccatcccgcag
gtcgatgttcccgcgataccgctagagatccacgaatcgatccacatggatcccatcgtc
ctggtgcccgccaccacaattcccgcacagacgagaaccattccgctggacatcccgcc
tcacccgggtcaaccatgacgcttccgctcatcagcatgcgcttcgaaggcgaggactgg
atcctcgggtcgaccgcggcgattcccaatttcggagacccttccggcgcccacccag
ggcatcaccattcacaccggccctggccccggaacgaccggcgagctcaagatatctatt
ccgggtttcgagattccgcaaatcgctaccacgagattcctgttggacgtgaacatcagc
ggtggtctgccggccttcaccttgttcgcgggtggcctgacgatccccacgaacgccatc
ccgttaacgatcgatgcgtccggcgcgctggatccgatcacgattttcccgggtgggtac
acgatcgacccgctgccgctgcacctggcgctgaatctcaccgtgcccgacagcagcatc
ccgatcatcgatgtcccgccgacgccaggggttcggcaacaccacggcgaccccgtcgtcg
gggttcttcaactccggcgccggtggggtgtcgggggttcggaaacgtcgggtcgaacctg
tcgggctggtggaaccaggcggcgagcgcgctggcggggtcgggatcggggtgttgaat
gtcggcacgctgggctcgggtgtgctcaacgtcggctcgggtgtctcggggatctacaac
accagcgtgttgccgctcgggacgccggcggtgctgtcgggcctcggcaacgtcggccat
cagctgtcgggcgtgtctgcggccgggaccgcgttgaaccagatccccatcctcaacatc
gggttggcggatgtgggcaacttcaacgtcgggttcggcaacgtcggggacgttaacctg
ggcgcggccaacctcggtgcgcaaaacctggggctgggcaacgtcggcaccggcaacctc
ggcttcgccaacgtcggccacggcaatatcggtttcggcaattcgggtctgaccgccggc
gcggccggcctgggcaacacggggttcggcaatgccggcagcgccaactatggtttcgcc
aaccagggcgtgcgcaacatcgggttggccaacaccggcaccggcaacatcgggatcggg
ctggtgggggacaacctcaccggcatcggggggcctgaactccggtgccggcaatatcggc
ttgttcaactccggcaccggcaacatcgggttcttcaactccgggaccggcaacttcggc
atcggtaactcgggcagcttcaacaccggcatcggcaatagcggaacgggcagcactggg
ctcttcaatgccggcagcttcaacaccggcgtggccaacgccggcagctacaacaccggc
agcttcaatgccggcgacaccaacaccggggggttcaacccgggcaccatcaacaccggc
tggttcaacaccggccacaccaataccggcatcgccaactcgggcaacgtcggcaccggc
gcgttcatgtcgggcaacttcagcaacggcctgttgtggcggggtgatcacgagggcctg
ttcagcctgttctacagcctcgacgtgccccggatcaccatcgtggacgccacctcgac
ggcggcttcggacccgtggtcctcccgcccatcccggtgccggccgttaatgcgcacctg
accggaaacgtcgcgatgggcgcattcaccattccgcagatcgacatccccgcactcacc
ccaaacatcaccggaagcgccgccttccgcatcgttgtggggtccgtgcgcattccgccg
gtgagtgtcattgtggagcaaataatcaacgcctcggttggggcggagatgaggatagat
cccttcgaaatgtggactcaaggcactaatggccttggtataaccttctatccattcgga
tcggccgacggttcgccctacgccaccggcccactcgttttcggcgccggcacgagcgac
ggaagccatctcaccatttccgcgtccagcggggcgtttaccactccgcagctcgaaact
ggcccgatcacgttgggcttccaggtgcccggcagcgtcaacgcgatcaccctcttcccc
```

```
ggtggtttgacgttcccggcgacctcgctgctgaacctggacgtgaccgccggcgccggc ggcgtggacatcccggccatcacctggcccgagatcgcggcgagcgccgacggctcggtg tatgtcctcgccagcagcatcccgctgatcaacatcccgccaccccgggcattgggaac agcaccatcaccccgtcgtcgggcttcttcaacgccggcgcgggcggggatcgggcttc ggcaacttcggcgcgggcaccccgggctggtggaaccaggcgcacaccgcgctggcgggg gcgggctcgggttttgccaacgttggcacgctgcattccggtgtgctcaacctgggctcg ggtgtctcggggatctacaacaccagcacgctgggggtggggaccccggcgctggtctca ggcctgggcaacgtcggccaccaactgtcggggctgctttccggcgggtccgcggtgaac ccggtgaccgttctgaatatcggggttggccaacgtcggcagccacaacgccggtttcggc aatgtcggggaggtcaacctgggcgcggccaacctcggcgcgcacaacctgggcttcgga aatatcggcgccggcaacctggggttcggcaatattggccacggcaatgtcggagtcggc aactcggtctgaccgcgggcgtgccgggcctgggcaatgtgggggttgggcaatgccggc ggcaacaactgggggttggccaacgtgggcgtgggcaatatcggggttggccaacaccggc accggcaacattgggatcgggctgaccggcgactaccagaccggcatcggcggcctaaat tccggtgccggcaacctggggttgttcaactccggcgccggcaacgtcgggttcttcaac accgggaccggcaacttcgggttgttcaactccggcagcttcaacaccggcgtcggcaat agcggaacgggcagcactgggctcttcaatgccggcagtttcaacaccggtgtggccaac gccggcagctacaacacgggcagcttcaatgtcggtgacaccaacaccggggggcttcaac ccgggcagcatcaacaccggccggctcaacgccggcaacgccaacaccggggtggccaac gcgggcaatgtcaacaccggcgccttcgtcaccggcaacttcagcaacggcatcctgtgg cgcggcgactaccagggcctggccggcttcgccgtgggctacaccctcccgctgttcccc gcggtgggcgccgacgtcagcggcgggatcggcccgattaccgtgctgccgcccatccac atcccgcccattccggtcggcttcgccgcggtcggtggcatcggcccgatcgccatcccg gacatctctgttccatccattcacttgggcctcgaccccgccgtccatgtcggctccatc accgtcaaccccattaccgtcaggaccccgcccgtgctcgtcagttactcccaaggagcc gtcaccagcacgtccggaccaacctcagagatttgggtcaagcccagcttcttccccgga atccggatcgcgccctctagcggcgggggtgcaacgtccacgcaaggggcatactttgtg gggcccatctccatcccctccggcacggtgaccttcccgggattcaccatccccctcgac ccgatcgacatcggcctgccggtgtcgctgaccatcccgggggttcaccatcccgggcggc accctgatccccaccctcccgctgggcctcgcgttgtccaatggcatcccgcccgtcgac atcccggccatcgttctcgaccggatcttgctggacctgcacgccgacaccactatcggc ccgatcaacgtcccgatcgccgggttcggcggggcgccgggtttcgggaactcgaccacg ctgccgtcgtcgggcttcttcaacaccggagctggcggcggttcgggctttagcaacacc ggcgcgggcatgtcgggattgctcaacgcgatgtcggatccgctgctcgggtcggcgtcg ggcttcgccaacttcggcacccagctctccggcatcctcaaccgcggcgccggcatctcg ggcgtgtacaacaccggcgcgctgggtgttgtcaccgcggccgtcgtctcgggtttcggc aacgtcggccagcaactgtcgggcttgctcttcaccggcgtcgggccctaa
```

These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3$^{rd}$ Edition, W.H. Freeman and Co., NY).

A nucleic acid encoding an Mtb polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding an Mtb polypeptide include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The Mtb polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the Mtb polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Viral vectors, such as poxyiral vectors, that encode an Mtb polypeptide include at least one expression control element operationally linked to the nucleic acid sequence encoding the Mtb polypeptide. The expression control elements are inserted in the viral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Mtb polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

DNA sequences encoding an Mtb polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding an Mtb polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), mycobacterium (such as *M. smegmatis*), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an Mtb polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Method for Detecting an Mtb Infection: Detection of T Cells

Methods for detection of a *Mycobacterium* infection in a subject are disclosed herein. In several embodiments, a *Mycobacterium* infection can be detected based on the presence of T cells in a biological sample, wherein the T cells specifically react with a Mtb polypeptide disclosed herein (see above).

In several embodiments, a biological sample comprising T cells is obtained from s subject of interest. Suitable biological samples include, but are not limited to, blood samples, peripheral blood mononuclear cells, sputum, saliva, cerebral spinal fluid or samples of isolated T cells (such as $CD8^+$ T cells and/or $CD4^+$ T cells), lymph node tissue, lung tissue, or other tissue sample. In one example, the sample is incubated with a *Mycobacterium* polypeptide, as disclosed herein, a polynucleotide encoding the Mtb polypeptide and an APC that expresses the Mtb polypeptide or a fragment thereof that binds MHC. The presence or absence of specific activation of the T cells is detected.

The $CD8^+$ T cells and/or $CD4^+$ T cells which recognize the peptide in the detection method have generally been presensitized in vivo to the Mtb polypeptide of interest. In several embodiments, these antigen-experienced T cells are generally present in the peripheral blood of a host which has been exposed to the antigen at a frequency of 1 to $10^6$ to 1 in $10^3$ peripheral blood mononuclear cells (PBMCs).

In one example, the sample is isolated T cells. For example, T cells can be isolated from a subject of interest by routine techniques (such as by Ficoll/Hypaque density gradient centrifugation of peripheral blood lymphocytes, or by fluorescence activated cell sorting). In one embodiment the T cells used in the assay are in the form of unprocessed or diluted samples, or are freshly isolated T cells (such as in the form of freshly isolated mononuclear cells (MCs) or peripheral blood mononuclear cells (PBMCs) which are used directly ex vivo, such that they are not cultured before being used in the method. However the T cells can be cultured before use, for example in the presence of one or more of the peptides, and generally also exogenous growth promoting cytokines. During culturing the peptides are typically presented on the surface of cells such as APCs. Pre-culturing of the T cells may lead to an increase in the sensitivity of the method. Thus the T cells can be converted into cell lines, such as short term cell lines.

In several embodiments, the T cells are incubated in vitro for two to nine days, such as about four days, at 37° C. with an Mtb polypeptide or fragment thereof that binds MHC. In several examples, the Mtb polypeptide or fragment thereof that binds MHC is included (at a concentration of, for example, about 5 to about 25 μg/ml, such as about 5, about 10, about 15, or about 20 μg/ml). In several examples, another aliquot of a T cell sample can be incubated in the absence of the Mtb polypeptide as a control.

In one embodiment, mononuclear cells (MCs) are separated from the sample. The MCs include the T cells and antigen presenting cells (APCs). Thus in the method the APCs present in the separated MCs can present the peptide to the T cells. In another embodiment only T cells, such as only $CD8^+$ T cells, only $CD4^+$ T cells, or only $CD3^+$ T cells, can be purified from the sample.

The APC used in the method may be any cell which has MHC class I molecules on its surface. It may or may not be a specialized antigen presenting cell, such as a B cell, dendritic cell or macrophage. The APC used in the method may be from the same host as the T cell. Generally, the APC is capable of presenting the peptide to a T cell. The APC can be a freshly isolated ex vivo cell or a cultured cell such as a cell from of a cell line.

T cells derived from the sample from the subject of interest can be placed into an assay with all the Mtb polypeptides (or a pool of the Mtb polypeptides, or a specific Mtb polypeptide)

which it is intended to test the relevant panel or the T cells can be divided and placed into separate assays each of which contain one or more of the peptides. In one embodiment, one or more of the polypeptides with an amino acid sequence set forth as SEQ ID NOs: 1-12, or an fragment of one or more of these polypeptides that bind MHC, is utilized. Two or more of any of the Mtb peptides disclosed herein can be used for simultaneous, separate or sequential use of T cells that recognize these polypeptides. Additional combinations of any of the Mtb polypeptides disclosed herein can be utilized.

In one embodiment the one or more peptide(s) is (are) provided to the presenting cell in the absence of the T cell. This cell is then provided to T cells isolated from the subject, typically after being allowed to present the peptide on its surface.

The duration for which the peptide is contacted with the cells will vary depending on the method used for determining recognition of the peptide. Typically $10^5$ to $10^7$, such as $5 \times 10^5$ to $10^6$ PBMCs are added to each assay. In the case where peptide is added directly to the assay its concentration is typically from $10^{-1}$ to $10^3$ µg/ml, such as about 0.5 to about 50 µg/ml or about 1 to about 10 µg/ml. The length of time for which the T cells are incubated with the peptide can be from about 4 to about 24 hours, such as from about 6 to about 16 hours, or for about 12 hours.

The determination of the specific recognition of the peptide by the T cells can be done by measuring the binding of the peptide to the T cells. Typically T cells which bind the peptide can be sorted based on this binding, for example using a fluorescence activated cell sorting (FACS) technique. The detection of the presence of T cells which recognize the peptide will be deemed to occur if the frequency of cells sorted using the peptide is above a control value.

Determination of whether the T cells recognize the peptide can also be done by detecting a change in the state of the T cells in the presence of the peptide or determining whether the T cells bind the peptide. The change in state is generally caused by antigen specific functional activity of the T cell after the T cell receptor binds the peptide. Generally when binding the T cell receptor the peptide is bound to an MHC class I molecule, which may be present on the surface of a PBMC or an antigen presenting cell (APC).

T cell activation can be detected by any means known to one of skill in the art. In one example, CD8$^+$ T cell activation is detected by evaluating cytolytic activity. In another example, CD8$^+$ T cell activation and/or CD4$^+$ T cell activation is detected by proliferation. In several examples, a level of proliferation that is at least two fold greater and/or a level of cytolytic activity that is at least 20% greater than in uninfected subjects indicates the presence of a *Mycobacterium* infection in the subject of interest.

The change in state of the T cell may be the start of or increase in secretion of a substance from the T cell, such as a cytokine, such as interferon (IFN)-γ, IL-2 or TNF-α. In one example, the substance can be detected by allowing it to bind to a specific binding agent and then measuring the presence of the specific binding agent/substance complex. The specific binding agent is typically an antibody, such as polyclonal or monoclonal antibodies that binds the substance, such as the cytokine. Antibodies to cytokines are commercially available, or can be made using standard techniques.

Typically the specific binding agent such as the antibody is immobilized on a solid support. After the cytokine is allowed to bind the solid support can optionally be washed to remove material which is not specifically bound to the antibody. The antibody/cytokine complex can be detected by using a second binding agent which will bind the complex, such as an antibody that is labeled (either directly or indirectly) with a label. Generally, the second agent binds the substance at a site which is different from the site which binds the first agent.

In several examples, the second binding agent can be detected by a third agent which is labeled directly or indirectly by a detectable label. For example the second agent may include a biotin, allowing detection by a third agent which comprises a strepavidin and a label, such as an enzymatic, radioactive or fluorescent label.

In one embodiment the detection system is an ELISPOT assay, such as the assay described in PCT Publication No. WO 98/23960, incorporated herein by reference. In one example, IFN-γ secreted from the T cell is bound by a first IFNγ specific antibody which is immobilized on a solid support. The bound IFN-γ is then detected using a second IFN-γ specific antibody which is labeled with a detectable label. Exemplary labeled antibodies are commercially available, such as from MABTECH™ (Stockholm, Sweden). An exemplary ELISPOT assay is described in the Examples section below.

The change in state of the T cell also can be measured may be the increase in the uptake of substances by the T cell, such as the uptake of thymidine. The change in state can also be measured by an increase in the size of the T cells, or proliferation of the T cells, or a change in cell surface markers on the T cell.

Reagents are provided herein for the detection of CD8 expressing cells (CD8$^+$) that specifically bind an Mtb polypeptide as disclosed herein. These reagents are tetrameric MHC Class I/immunogenic TARP polypeptide complexes. These tetrameric complexes include an Mtb polypeptide, such as a polypeptide of nine to twenty amino acids in length that specifically binds MHC class I.

Tetrameric MHC Class I/peptide complexes can be synthesized using methods well known in the art (Altmann et al., *Science* 274:94, 1996, which is herein incorporated by reference). In one specific non-limiting example, purified HLA heavy chain polypeptide and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the transmembrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with strepavidin.

In one embodiment, the strepavidin is labeled. Suitable labels include, but are not limited to, enzymes, magnetic beads, colloidal magnetic beads, haptens, fluorochromes, metal compounds, radioactive compounds or drugs. The enzymes that can be conjugated to strepavidin include, but are not limited to, alkaline phosphatase, peroxidase, urease and β-galactosidase. The fluorochromes that can be conjugated to the strepavidin include, but are not limited to, fluorescein isothiocyanate, tetramethylrhodamine isothiocyanate, phycoerythrin, allophycocyanins and Texas Red. For additional fluorochromes that can be conjugated to strepavidin, see Haugland, R. P., *Molecular Probes: Handbook of Fluorescent Probes and Research Chemicals* (1992-1994). The metal compounds that can be conjugated to the strepavidin include, but are not limited to, ferritin, colloidal gold, and particularly, colloidal superparamagnetic beads. The haptens that can be conjugated to the strepavidin include, but are not limited to, biotin, digoxigenin, oxazalone, and nitrophenol. The radioactive compounds that can be conjugated to strepavidin are known to the art, and include but are not limited to technetium 99 m ($^{99}$Tc), $^{125}$I and amino acids comprising any radionuclides, including, but not limited to, $^{14}$C, $^3$H and $^{35}$S. Generally, strepavidin labeled with a fluorochrome is utilized in the methods disclosed herein.

In one embodiment, suspension of cells including T cells that specifically recognize an Mtb polypeptide is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620, incorporated herein by reference).

Method for Detecting an Mtb Infection: Skin Tests

In another aspect, this invention provides methods for using one or more of the polypeptides described above to diagnose *Mycobacterium* infection, and in particular tuberculosis, using a skin test. A "skin test" is any assay performed directly on a patient in which a delayed-type hypersensitivity (DTH) reaction (such as induration, swelling, reddening or dermatitis) is measured following administration into the skin, such as the intradermal injection of one or more polypeptides described above. Such injection can be achieved using any suitable device sufficient to contact the polypeptide or polypeptides with dermal cells of the patient, such as a tuberculin syringe or 1 ml syringe. In several examples, the reaction is measured at least 48 hours after injection, such as between about 48 and about 72 hours after injection.

A DTH reaction is a cell-mediated immune response which is greater in subjects that have been exposed previously to the test antigen (the Mtb polypeptide, fragment thereof that binds MHC, or fusion protein thereof). The response can be measured visually, such as using a ruler. In several examples, a response that is greater than about 0.5 cm in diameter, such as greater than about 1.0 cm in diameter, is a positive response, and is indicative of *Mycobacterium* infection.

The Mtb polypeptides disclosed herein can be formulated for use in a skin test as pharmaceutical compositions containing a polypeptide and a physiologically acceptable carrier. These compositions typically contain one or more of the disclosed Mtb polypeptides (or a fragment thereof that binds MHC or a fusion protein thereof) in an amount ranging from about 1 µg to about 100 µg, such as from about 10 µg to about 50 µg in a volume of 0.1 ml. The carrier employed in a pharmaceutical composition can be a saline solution with appropriate preservatives, such as phenol and/or TWEEN80™.

Generally, the polypeptide employed in a skin test is of sufficient size such that it remains at the site of injection for the duration of the reaction period. In several examples, a polypeptide that is at least nine amino acids in length is sufficient. Without being bound by theory, the polypeptide is broken down by macrophages within hours of injection to allow presentation to T-cells. Such polypeptides can contain repeats of one or more of the above disclosed sequences and/or other immunogenic or non-immunogenic sequences.

Thus, the determination of the recognition of the peptide by the T cells can be measured in vivo. In several examples, the peptide is administered to the individual and then a response which indicates recognition of the peptide may be measured.

In one embodiment the peptide is administered intradermally, typically in a similar manner to the Mantoux test. The peptide can be administered epidermally. The peptide is typically administered by needle, such as by injection, but can be administered by other methods such as ballistics, for example the ballistics techniques which have been used to deliver nucleic acids. Published EPC Application No. EP-A-0693119 describes techniques which can typically be used to administer the peptide. In several examples, from 0.001 to 1000 µg, for example from 0.01 to 100 µg or 0.1 to 10 µg of peptide is administered. Alternatively an agent can be administered which is capable of providing the peptides in vivo. Thus a polynucleotide capable of expressing the polypeptide can be administered. The polynucleotide typically has any of the characteristics of the polynucleotide which is discussed below. Polypeptide is expressed from the polynucleotide in vivo and recognition of the peptide in vivo may be measured. Typically from 0.001 to 1000 µg, for example from 0.01 to 100 µg or 0.1 to 10 µg of polynucleotide is administered.

Method for Detecting an Mtb Infection: Detection of Antibodies

Methods are disclosed herein wherein the polypeptides described above are used to diagnose *Mycobacterium* infection, and in particular tuberculosis. In these embodiments, methods are provided for detecting *Mycobacterium* infection in a biological sample, using one or more of the above polypeptides, alone or in combination. In several embodiments in multiple polypeptides are employed. The polypeptide(s) are used in an assay to determine the presence or absence of antibodies to the polypeptide(s) in a biological sample (such as, but not limited to, whole blood, sputum, serum, plasma, saliva, or cerebrospinal fluid) relative to a control. The presence of such antibodies indicates previous sensitization to mycobacterial antigens which may be indicative of *Mycobacterium* infection, and in particular tuberculosis.

In embodiments in which more than one polypeptide is employed, the polypeptides can be complementary, such that one component polypeptide will detect infection in samples where the infection would not be detected by another component polypeptide). Complementary polypeptides may generally be identified by using each polypeptide individually to evaluate serum samples obtained from a series of patients known to be infected with *Mycobacterium*. After determining which samples are correctly identified as positive with each polypeptide, combinations of two or more polypeptides may be formulated that are capable of detecting infection in most, or all, of the samples tested. Complementary polypeptides are of use to improve sensitivity of a diagnostic test. Thus, more than one of the above-described Mtb polypeptides can be included in an assay. Additional polypeptides from Mtb (those not described herein) optionally can be included in the assay.

There are a variety of assay formats that can be used to detect antibodies in a sample (see, for example, Harlow and Lane, Antibodies: A Laboratory Manual, Cold Spring Harbor Laboratory (1988), which is incorporated herein by reference). In general, the presence or absence of an Mtb infection in a patient may be determined by (a) contacting a biological sample obtained from a patient with one or more Mtb polypeptides; (b) detecting in the sample the presence (or absence) of an antibody that binds to the polypeptide(s); and (c) comparing the level of antibody with a control. The control can be a standard value, such as a pre-determined cut-off value. The control can be the amount of antibodies in a subject known to be infected with Mtb, or the amount of antibodies that specifically bind the polypeptide(s) in a subject known not to be infected with Mtb.

In several embodiments, the assay involves the use of a polypeptide immobilized on a solid support. Antibodies that specifically bind the polypeptide(s) of interest bind to the solid support. The bound antibody can then be detected using a detection reagent that includes a detectable label. Suitable detection reagents include labeled antibodies that bind to the antibody/polypeptide complex. Suitable detection reagents also include second unlabeled antibodies that bind to the antibody polypeptide complex and a third antibody that specifically binds the second antibody. Suitable detection reagents also include unbound polypeptide labeled with a reporter group (such as in a semi-competitive assay).

Alternatively, a competitive assay may be utilized, in which an antibody that binds to the polypeptide of interest is labeled with a reporter group is incubated with the sample. Following incubation, the antibody is then allowed to bind to the immobilized antigen after incubation of the antigen with the sample. The extent to which components of the sample inhibit the binding of the labeled antibody to the immobilized polypeptide is indicative of the reactivity of the sample with the immobilized polypeptide.

A solid support used in an assay disclosed herein can be any solid material to which the antigen may be attached. For example, the solid support can be a test well in a microtiter plate or a nitrocellulose or other suitable membrane. Alternatively, the solid support may be a bead or disc, such as glass, fiberglass, latex or a plastic material such as polystyrene or polyvinylchloride. The support can also be a magnetic particle or a fiber optic sensor, such as those disclosed, for example, in U.S. Pat. No. 5,359,681.

The polypeptides can be bound to the solid support using a variety of techniques. The binding of the polypeptides can be accomplished by a noncovalent association, such as adsorption, or covalent attachment, such as a direct linkage between the antigen and functional groups on the support or a linkage through a cross-linking agent.

For binding by adsorption, binding can be achieved by contacting one or more Mtb polypeptide(s) (generally in a buffer) with the solid support for a suitable amount of time. The contact time for binding is typically between about 1 hour and 1 day. In general, binding is achieved by contacting a polystyrene or polyvinylchloride solid support with an amount of the one or more Mtb polypeptide(s) ranging from about 10 ng to about 1 µg, such as about 100 ng of antigen.

Covalent attachment of the Mtb polypeptide(s) of interest to a solid support can generally be achieved by reacting the support with a bifunctional reagent that reacts with both the support and a functional group, such as a hydroxyl or amino group, on the polypeptide. For example, an Mtb polypeptide can be bound to supports having an appropriate polymer coating using benzoquinone or by condensation of an aldehyde group on the support with an amine and an active hydrogen on the polypeptide (Pierce Immunotechnology Catalog and Handbook, at A12 A13, 1991).

In certain embodiments, the assay is an enzyme linked immunosorbent assay (ELISA). This assay can be performed by first contacting a polypeptide antigen that has been immobilized on a solid support (such as in the well of a microtiter plate) with the sample in a manner such that that antibodies present within the sample that specifically bind the polypeptide of interest bind the immobilized polypeptide. Unbound sample is then removed and a detection reagent capable of binding to the immobilized antibody-polypeptide complex is added. The amount of detection reagent that remains bound is determined using a method appropriate for the specific detection reagent. For example, the detection method can detect fluorescence or the presence of an enzymatic activity.

In some embodiments, the polypeptide is immobilized on the support; any remaining protein binding sites on the support are typically blocked. Any suitable blocking agent can be used to block the unbound protein binding sites, such as bovine serum albumin or TWEEN20™ can be employed. The immobilized polypeptide is then incubated with the sample, and the antibody is allowed to bind to the antigen. The sample can be diluted with a suitable diluent, for example a buffer such as phosphate-buffered saline (PBS) prior to incubation. In general, an appropriate contact time (incubation time) is a period of time that is sufficient to detect the presence of antibody in a *Mycobacterium*-infected sample. In one specific, non-limiting example, the contact time is sufficient to achieve a level of binding that is at least 95% of that achieved at equilibrium between bound and unbound antibody. The time necessary to achieve equilibrium can be determined by assaying the level of binding that occurs over a period of time. At room temperature, an incubation time of about 30 minutes is generally sufficient.

Unbound sample can then be removed by washing the solid support with an appropriate buffer, such as PBS containing 0.1% TWEEN20™. A detection reagent can then be added to the solid support. A detection reagent can be any compound that binds to the immobilized antibody-polypeptide complex and can be detected. In several embodiments, the detection reagent contains a binding agent (such as, for example, Protein A, Protein G, immunoglobulin, lectin or free antigen) conjugated to a label. Labels of use include enzymes (such as horseradish peroxidase), substrates, cofactors, inhibitors, dyes, radionuclides, luminescent groups, fluorescent groups and biotin. The conjugation of a binding agent to a label can be achieved using methods known in the art; conjugated binding agents are also commercially available (such as from Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the label. For radioactive labels, scintillation counting or autoradiographic methods can be used for detection. Spectroscopic methods may be used to detect dyes, luminescent groups and fluorescent groups used as labels. Biotin can be detected using avidin coupled to a different label, such as a radioactive label, fluorescent label or an enzymatic label. Enzymatic labels can be detected by the addition of substrate (generally for a specific period of time), followed by spectroscopic or other analysis of the reaction products.

To determine the presence or absence of anti-*Mycobacterium* antibodies in the sample, the signal detected from the label that bound to the solid support is generally compared to a control. In one embodiment, the control is a standard value, such as the average mean signal obtained when the immobilized antigen is incubated with samples from an uninfected patient. In general, a sample generating a signal that is two or three standard deviations above the control is considered positive for *Mycobacterium* infection. In another embodiment, the control value is determined using a Receiver Operator Curve, according to the method of Sackett et al., Clinical Epidemiology: A Basic Science for Clinical Medicine, Little Brown and Co., pp. 106 107 (1985). Briefly, in this embodiment, the control value is determined from a plot of pairs of true positive rates (sensitivity) and false positive rates (100% specificity) that correspond to each possible control value for the diagnostic test result. The control value on the plot that encloses the largest area is the most accurate cut-off value, and a sample generating a signal that is higher than the cut-off value determined by this method is considered positive. Alternatively, the cut-off value may be shifted to minimize the false positive rate, or to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as, but not limited to, nitrocellulose. In a flow-through test, antibodies within the sample bind to the immobilized polypeptide as the sample passes through the membrane. A detection reagent (for example, protein A-colloidal gold) binds to the antibody-polypeptide complex as the solution containing the detection reagent flows through the membrane. The detection of bound detection reagent can be performed as described above.

In one example of the strip test format, one end of the membrane to which the polypeptide is bound is immersed in a solution containing the sample. The sample migrates along the membrane through a region containing the detection reagent and to the area of immobilized polypeptide. The concentration of the detection reagent at the polypeptide indicates the presence of anti-Mycobacterium antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an enzyme linked immunosorbant assay (ELISA). In several embodiments, the amount of polypeptide immobilized on the membrane ranges from about 25 ng to about 1 µg, such as from about 50 ng to about 500 ng. Such tests can typically be performed with a very small volume of patient serum or blood.

Method for Detecting an Mtb Infection: Detection of Polynucleotides

Diagnostic reagents include the use of polynucleotide sequences encoding one or more of the above disclosed Mtb polypeptides. *Mycobacterium* infection can be detected by detecting the presence, absence, or level of mRNA encoding a *Mycobacterium* polypeptide in a biological sample. In several examples, hybridization assays are utilized, such as Northern blot or dot blot assays. In additional examples, PCR based assays are utilized.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using purification kit, buffer set and protease from commercial manufacturers, such as QIAGEN®, according to the manufacturer's instructions. For example, total RNA from cells in culture (such as those obtained from a subject) can be isolated using QIAGEN®RNeasy mini-columns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared a biological sample can be isolated, for example, by cesium chloride density gradient centrifugation.

Methods for quantitating mRNA are well known in the art. In one example, the method utilizes reverse transcriptase polymerase chain reaction (RT-PCR). Generally, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System™ (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 7700®. Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

In some examples, 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is can be performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH), beta-actin, and 18S ribosomal RNA.

A more recent variation of the RT-PCR technique is the real time quantitative PCR, which measures PCR product accumulation through a dual-labeled fluorigenic probe (i.e., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., Genome Research 6:986 994, 1996). Quantitative PCR is also described in U.S. Pat. No. 5,538,848, the disclosure of which is incorporated herein by reference. Related probes and quantitative amplification procedures are described in U.S. Pat. Nos. 5,716,784 and 5,723,591, the disclosures of which are incorporated herein by reference. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantitating gene expression using fixed, paraffin-embedded tissues as the RNA source, including mRNA isolation, purification, primer extension and amplification are given in various published journal articles (see Godfrey et al. J. Molec. Diagnostics 2: 84 91, 2000; K. Specht et al., Am. J. Pathol. 158: 419 29, 2001). Briefly, a representative process starts with cutting about 10 μm thick sections of paraffin-embedded tissue sample. The RNA is then extracted, and protein and DNA are removed. After analysis of the RNA concentration, RNA repair and/or amplification steps can be included, if necessary, and RNA is reverse transcribed using gene specific promoters followed by RT-PCR.

An alternative quantitative nucleic acid amplification procedure is described in U.S. Pat. No. 5,219,727, which is incorporated herein by reference. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "house keeping" gene or "internal control" can also be evaluated. These terms are meant to include any constitutively or globally expressed gene whose presence enables an assessment of cytokine mRNA levels. Such an assessment comprises a determination of the overall constitutive level of gene transcription and a control for variations in RNA recovery.

Monitoring the Progression of an Infection and/or Effectiveness of Therapy

In several embodiments, the diagnostic methods disclosed herein are used for monitoring the progression of a *Mycobacterium* infection. In this embodiment, assays as described above for the diagnosis of a *Mycobacterium* infection may be performed over time, and the change in the level of reactive polypeptide(s) evaluated. For example, the assays can be performed about every 12, 24, 36, 48, 60 or 72 hours for a specified period, such as over months or weeks, and thereafter performed as needed.

In some examples, the presence of an Mtb polypeptide, or a polynucleotide encoding the polypeptide is assessed. Generally, the *Mycobacterium* infection is progressing in those patients in whom the level of polypeptide (such as detected using a binding agent), the level of polynucleotide, the level of antibodies, or the level of T cells increases over time. In contrast, the *Mycobacterium* infection is not progressing when the level of reactive polypeptide, the level of polynucleotide, the level of antibodies, or the level of T cells either remains constant or decreases with time. In this manner, the effectiveness of a particular therapeutic regimen can be assessed.

In one embodiment, the presence of an Mtb polypeptide is assessed in a subject. The subject is administered a therapeutic protocol. The presence of the Mtb polypeptide is then assessed. An increase or no change in the amount of the Mtb polypeptide (or polynucleotide) as compared to the amount of the Mtb polypeptide prior to the administration of the therapeutic protocol indicates that the therapeutic protocol in not effective, and the Mtb infection is progressing. A decrease in the amount of the Mtb polypeptide (or polynucleotide) as compared to the amount of the Mtb polypeptide (or polynucleotide) prior to the administration of the therapeutic protocol indicates that the therapeutic protocol is effective, and that the Mtb infection is not progressing.

In another embodiment, the presence of T cells, such as $CD8^+$ T cells and/or $CD4^+$ T cells, that specifically recognize an Mtb polypeptide is assessed in a subject. The subject is administered a therapeutic protocol. The presence of the T cells that specifically recognize the Mtb polypeptide is then assessed. An decrease or no change in the amount of $CD8^+$ T cells and/or $CD4^+$ T cells that specifically recognize the Mtb polypeptide as compared to the amount of the $CD8^+$ T cells and/or $CD4^+$ T cells, respectively, that specifically recognize the Mtb polypeptide prior to the administration of the therapeutic protocol indicates that the therapeutic protocol in not effective. An increase in the amount of the $CD8^+$ T cells and/or $CD4^+$ T cells that specifically recognize the Mtb polypeptide as compared to the amount of the $CD8^+$ T cells and/or $CD4^+$ T cells that specifically recognize the Mtb polypeptide prior to the administration of the therapeutic protocol indicates that the therapeutic protocol is effective.

It should be noted that for any of the above-described assays, to improve sensitivity, multiple *Mycobacterium* markers may be assayed within a given sample. It will be apparent that the assays disclosed herein can be used in combination. Thus, sets of *Mycobacterium* polypeptides, and combinations of assays can be for optimal sensitivity and specificity.

Numerous other assay protocols exist that are suitable for use with the polypeptides of the present invention. The above descriptions are intended to be exemplary only.

The disclosure is illustrated by the following non-limiting Examples.

EXAMPLES

For many infections, the repertoire of the CD8 response is shaped by the entry of antigen into the MHC-I processing pathway, binding of peptides and/or non-peptide antigens to MHC-I molecules, and recognition of these structures by T cells. Ultimately, a relatively limited subset of pathogen-specific T cells emerge. While a number of commonly recognized CD4 Mtb antigens have been described (Reed et al., *Microbes Infect* 7:922-931, 2005) (ESAT-6, CFP10, Ag85, etc.), surprisingly little is known about common Mtb antigens recognized by human CD8+ T cells. The majority of CD8 epitopes that have been identified were defined by testing of Mtb peptides selected for high affinity binding to MHC Class Ia molecules (HLA-A2 in most cases (see, for example, Lalvani, *Microbes Infect* 7:922-931, 1998)). In almost all of these, however, the ex vivo frequency of these T cells in Mtb-infected individuals is low or undetectable, suggesting that these specificities may not represent immunodominant responses. In contrast, in the limited cases in which T cells have been used to define epitopes contained in selected Mtb antigens, high ex vivo frequencies have been demonstrated (see Lewinsohn et al., *Am J Respir Crit Care Med* 166:843-848, 2002), suggesting, that a T cell-centered approach can identify immunodominant epitopes. Moreover, CD8 T cell responses to some Mtb antigens which represent good CD4 antigens (CFP10, ESAT-6, Ag85, and Mtb39) have been detected at high frequency in persons infected with Mtb. Therefore, a limited library of overlapping synthetic peptides representing several known CD4 Mtb antigens was used to determine the magnitude of the CD8 response to these antigens in persons with active tuberculosis (TB) and latent tuberculosis infection (LTBI) as well as uninfected subjects. Furthermore, a panel of Mtb-specific CD8+ T cell clones was utilized to define minimal epitopes recognized within these antigens and determined the contribution of these novel epitopes to the ex vivo Mtb-specific CD8 response.

Example 1

Materials and Methods

Human Subjects. Uninfected individuals were defined as healthy individuals with a negative tuberculin skin test (TST) and no know risk factors for infection with Mtb. Individuals with LTBI were defined as healthy persons with a positive TST and no symptoms and signs of active TB. In all active TB cases, pulmonary TB was diagnosed by the TB Controller of the county and confirmed by positive sputum culture for *Mycobacterium tuberculosis*. Peripheral blood mononuclear cells (PBMC) were isolated from whole blood obtained by venipuncture or apheresis.

Media and Reagents. Culture medium consisted of RPMI 1640 supplemented with 10% Fetal Bovine Sera (FBS; Bio Whittaker), $5 \times 10^{-5}$ M 2 ME (Sigma-Aldrich), and 2 mM glutamine (GIBCO BRL). For the growth and assay of Mtb-reactive T cell clones, RPMI 1640 was supplemented with 10% human serum. Mtb strain H37Rv was obtained from the American Type Culture Collection (Rockville, Md.) and prepared as previously described (Lewinsohn et al., *J Immunol* 165:925-930, 2000). Peptides were synthesized by Genemed Synthesis, Inc, (San Francisco, Calif.). Synthetic peptide pools consisted of 15-mers overlapping by 11 amino acids (aa) representing Mtb proteins demonstrated to be potent CD4 antigens. Peptide pools representing CFP-10 (Berthet et al., *Microbiology* 144:3195-3203, 1998; Dillon et al., *J Clin Microbiol* 38:3285-3290, 2000), ESAT-6 (Sorenson et al., *Infect Immun* 63:1710-1717, 1995), Mtb39a (two pools, A &B, reference) (Dillon et al., *Infect Immun* 67:2941-2950, 1999), Mtb8.4 (Coler et al., *J Immunol* 161:2356-2364, 1998), Mtb 9.9 (Alderson et al., *J Exp Med* 191:551-560, 2000), (Coler et al., *J Immunol* 161:2356-2364, 1998), Mtb 9.9 (Alderson et al., *J Exp Med* 191:551-560, 2000), EsxG (Rosenkrands et al., *Electrophoresis* 21:3740-3756, 2002), 19 kDa antigen (Collins et al. *J Gen Microbiol* 136:1429-1436, 1990), antigen 85b (Borremans et al., *Infect Immun* 57:3123-3130, 1989) (two pools, A & B, reference) were synthesized. Peptides were resuspended in DMSO and up to 50 peptides were combined into one pool such that each peptide in the pool was at a concentration of 1 mg/ml. Peptide pools were stored at $-80°$ C.

Cell Lines and T Cell Clones. EBV-transformed B cell lines, LCL, were either generated using supernatants from the cell line 9B5-8 (American Type Culture Collection) or obtained from the National Marrow Donor Program (NMDP; Minneapolis, Minn.). LCL were maintained by continuous passage as previously described (Heinzel et al., *J Exp Med* 196:1473-1481, 2002). Mtb-specific T cell clones were isolated from individuals with LTBI or active tuberculosis, using Mtb-infected DCs as APCs and limiting dilution cloning methodology as previously described (Lewinsohn et al., *J Immunol* 165:925-930, 2000). Briefly, CD8+ T cells were isolated from PBMC using negative selection using CD4 antibody-coated beads and then positive selection using CD8 antibody-coated magnetic beads per the manufacturer's instructions (Miltenyi Biotec, Auburn Calif.) or via flow cytometry. In this case, CD4-PE (BD Biosciences cat #555347) negative, CD8-APC (BD Biosciences, cat# 555369) positive cells (purity >99%) were sorted on a Becton Dickenson LSR II. T cells were seeded at various concentrations in the presence of a $1 \times 10^5$ irradiated autologous Mtb-infected DC, generated as described below, and rIL-2 (5 ng/ml) in cell culture media consisting of 200 µl of RPMI 1640 supplemented with 10% human sera. Wells exhibiting growth between 10-14 days, were assessed for Mtb specificity using ELISPOT and Mtb-infected DC as a source of APCs. T cells retaining Mtb specificity were further phenotyped for αβ T cell receptor expression and CD8 expression by FACS and expanded as described below. Vβ usage was determined using the IOTest Beta Mark Kit from Beckman Coulter.

Expansion of T cell clones. To expand the CD8+ T cell clones, a rapid expansion protocol using anti-CD3 mAb stimulation was used as described previously (Heinzel et al., *J Exp Med* 196:1473-1481, 2002).

Generation and Infection of Peripheral Blood DCs. Monocyte-derived DCs were prepared (Heinzel et al., supra; Romani et al., *J Exp Med* 180:83-93, 1994). To generate Mtb-infected DC, cells ($1 \times 10^6$) were cultured overnight in the presence of Mtb (multiplicity of infection [MOI]=50:1). After 18 hours, the cells were harvested and resuspended in RPMI/10% human serum.

MHC binding assays. The MHC-peptide binding assay utilized measures the ability of peptide ligands to inhibit the binding of a radiolabeled peptide to purified MHC molecules, and has been described in detail elsewhere (Sidney et al., 1999. UNIT 18.3 Measurement of MHC/peptide interactions by gel filtration. In Current Protocols in Immunology. Coligan et al., eds., John Wiley & Sons, Inc., 1996). Briefly, purified MHC molecules, test peptides, and a radiolabeled probe peptide were incubated at room temperature in the presence of human B2-microglobulin and a cocktail of protease inhibitors. After a two-day incubation, binding of the radiolabeled peptide to the corresponding MHC class I molecule was determined by capturing MHC/peptide complexes on W6/32 antibody (anti-HLA A, B, and C) or B123.2 (anti-HLA B, C and some A) coated plates, and bound counts per minute (cpm) were measured using a microscintillation counter. For competition assays, the concentration of peptide yielding 50% inhibition of the binding of the radiolabeled peptide was calculated. Peptides were typically tested at six different concentrations covering a 100,000-fold dose range, and in three or more independent assays. Under the conditions utilized, where [label]<[MHC] and $IC_{50} \geq$ [MHC], the measured $IC_{50}$ values are reasonable approximations of the true Kd values.

IFN-γ ELISPOT assay. The IFN-γ ELISPOT assay was performed as described previously (Beckman et al., *J Immunol* 157:2795-2803, 1996). For determination of ex vivo frequencies of CD4+ or CD8+ T cells responding to Mtb infection or Mtb antigens, CD4+ or CD8+ T-cells were positively selected from PBMC using magnetic beads (Miltenyi Biotec, Auburn Calif.) as a source of responder T cells and tested in duplicate at four different cell concentrations. Autologous DC (20,000 cells/well) were used as APC and DC were either infected with Mtb or pulsed with peptide pools (5 μg/ml, final concentration of each peptide) and then added to the assay. For assays using T cell clones, T cells (1000 or 5000 cells/well) were incubated with autologous LCL (20,000 cells/well) in the presence or absence of antigen.

Data analysis: To determine the ex vivo frequency of antigen-specific T cells, the average number of spots per well for each duplicate was plotted against the number of responder cells per well. Linear regression analysis was used to determine the slope of the line, which represents the frequency of antigen-specific T cells. The assay is considered positive, i.e. reflecting the presence of a primed T cell response, if the binomial probability (Lewinshon et al., *Microbes Infect* 8:2587-2598, 2006) for the number of spots is significantly different by experimental and control assays. To determine differences in ex vivo T cell frequencies between groups, Wilcoxon/Kruskal-Wallis analysis was used.

Example 2

Defining Immunodominant Mtb-Specific CD8+ Antigens

To define immunodominant Mtb-specific CD8+ antigens, and to determine whether or not these responses result from infection with Mtb, CD8+ T cells were used from donors uninfected, with LTBI, or actively infected with Mtb. Responses were determined either directly ex vivo, or using CD8+ T cell clones obtained by limiting dilution cloning on Mtb-infected autologous DC (Lewinsohn et al., *J Immunol* 165:925-930, 2000). As much is known about dominant CD4+ Mtb antigens, a panel of these commonly recognized antigens was selected for further evaluation. These were: Mtb39, CFP10, and Mtb8.4, Mtb9.9, ESAT-6, Ag85b, 19 kDa, and EsxG. To avoid bias introduced by using peptides of predicted HLA-binding specificity, we synthesized overlapping peptides (15 aa, overlap 11 aa) to represent the proteins of interest (Lewinshon et al., *J Immunol* 166:439-446, 2001).

To accurately determine the ex vivo effector cell frequencies of CD8+ T cells, linear regression analysis was used. As shown in FIG. 1, magnetic bead purified CD8+ T cells were tested against peptide pulsed DC over a range of CD8+ T cell numbers in an IFN-γ ELISPOT assay. A positive assay was determined as described below and if positive, the antigen specific frequency was determined using linear regression.

Figure 2:
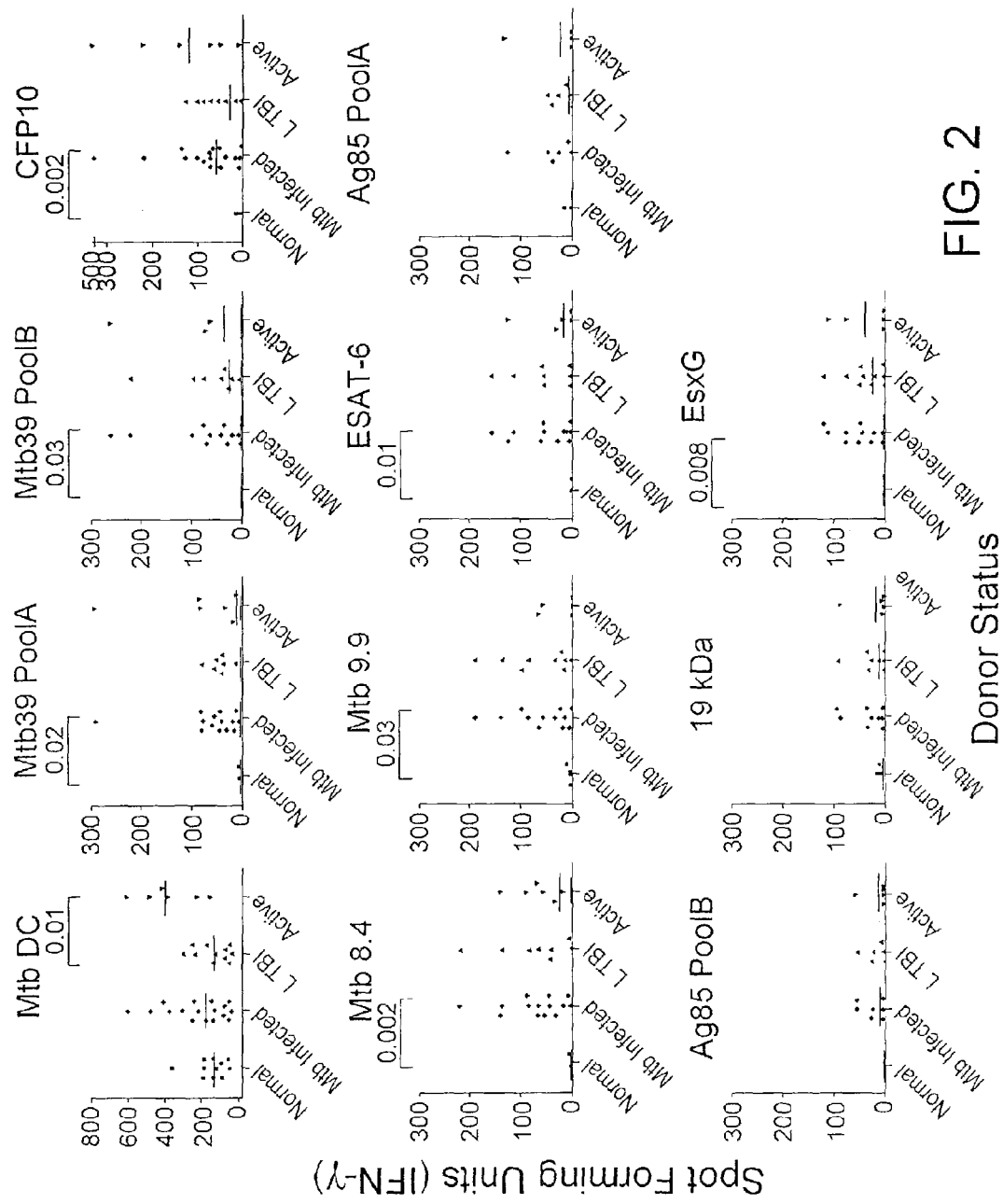
FIG. 2 is a set of graphs showing ex vivo CD8$^+$ T cell frequencies to Mtb antigens are associated with Mtb infection. As described above (see FIG. 1), to determine ex vivo CD8$^+$ T cell frequencies, autologous DC either infected with Mtb or pulsed with cognate peptide pools were incubated with CD8$^+$ T cells in an IFN-γ ELISPOT assay. Subjects without evidence for Mtb infection, those with LTBI, and those with active TB (culture confirmed pulmonary tuberculosis) were evaluated. "Mtb Infected" includes those with LTBI and active tuberculosis. P values are noted where $P=<0.05$ (Wilcoxon/Kruskal-Wallis).

Subjects uninfected (n=14), those with LTBI (n=20) and those with active TB (n=12) were evaluated for CD8+ responses to a panel of Mtb CD4+ T cell antigens, as well as to Mtb-infected DC. All subjects tested had robust CD8+ T cell responses to Mtb-infected DC and were of greater magnitude in individuals with active TB than in those with LTBI (p=0.01; FIG. 2, Table I). However, CD8+ T cell responses to the panel of Mtb antigens were found almost exclusively in those infected with Mtb in that statistically significant differences between uninfected and Mtb-infected individuals were noted for seven of ten antigens for both the magnitude of the response (FIG. 2) and the proportion of positive assays (Table I).

TABLE I

CD8+ T cell responses to known TB antigens.

| Antigen | Mtb Infected # positive[a]/ # tested (%) | Mtb Uninfected # positive[a]/ # tested (%) | P value (2 tail fishers) |
|---|---|---|---|
| Mtb DC | 17/17 (100) | 11/11 (100) | |
| Mtb39 Pool A | 13/30 (43) | 0/14 (0) | 0.003 |
| Mtb 39 Pool B | 10/30 (33) | 0/14 (0) | 0.01 |
| CFP10 | 14/30 (47) | 1/14 (7) | 0.02 |
| Mtb 8.4 | 13/30 (43) | 0/14 (0) | 0.003 |
| Mtb 9.9 | 10/25 (40) | 1/14 (7) | 0.06 |
| ESAT 6 | 12/25 (48) | 0/14 (0) | 0.003 |
| Ag85b Pool A | 5/22 (23) | 1/14 (7) | 0.37 |
| Ag85b Pool B | 4/22 (18) | 0/14 (0) | 0.14 |
| 19 kd | 6/22 (27) | 1/12 (8) | 0.38 |
| EsxG | 9/22 (41) | 0/14 (0) | 0.006 |

[a]Positive assay defined in text.

However differences in CD8+ T cell responses between individuals with active TB and LTBI were not statistically different. While strong CD8+ T cell responses were observed against many of the antigens tested, it is equally notable that several subjects with strong Mtb directed CD8+ T cell responses did not have demonstrable responses to many of the antigens tested.

These ex vivo frequency data demonstrate the presence of high-frequency responses to a number of known Mtb antigens, but do not shed light on the restricting allele, minimal epitope, or dominance hierarchy within the gene of interest. To address this question, limiting dilution cloning of human CD8+ T cells using Mtb-infected DC was performed (see Lewinsohn et al., *J Immunol* 166:439-446, 2001), and panels of both classically and non-classically HLA-restricted CD8+ T cell clones were generated. Using peptide pools representing known CD4+ antigens, the antigenic specificity of the HLA-Ia restricted clones can be defined in more than half of the clones (Table II).

TABLE II

Many CD8+ T cell clones recognize known CD4+ T cell antigens

| Donor | Tb Status | HLA-Ia Clones (#)[a] | Antigen Identified (#)[b] | # Distinct Antigens (#)[c] | # Distinct Epitopes (#)[d] |
|---|---|---|---|---|---|
| D431 | Active TB | 1 | 0 | 0 | 0 |
| D432 | Active TB | 14 | 4 | 2 | 2 |
| D466 | Active TB | 11 | 10 | 1 | 2 |
| D571 | Active TB | 7 | 7 | 1 | 1 |
| D480 | Active TB | 6 | 6 | 1 | 1 |
| D481 | Active TB | 11 | 11 | 1 | 1 |
| D426 | LTBI | 1 | 0 | 0 | 0 |
| D443 | LTBI | 1 | 1 | 1 | 1 |
| D454 | LTBI | 2 | 2 | 2 | 2 |
| D504 | LTBI | 7 | 1 | 1 | 1 |
| Totals | | 61 | 42 | 10 | 11 |

[a]Number of clones derived from donor.
[b]Number of clones for which cognate antigen was identified.
[c]Total number of distinct antigens identifed from the clone set.
[d]Total number of distinct epitopes identified from the clone set.

Figure 4:
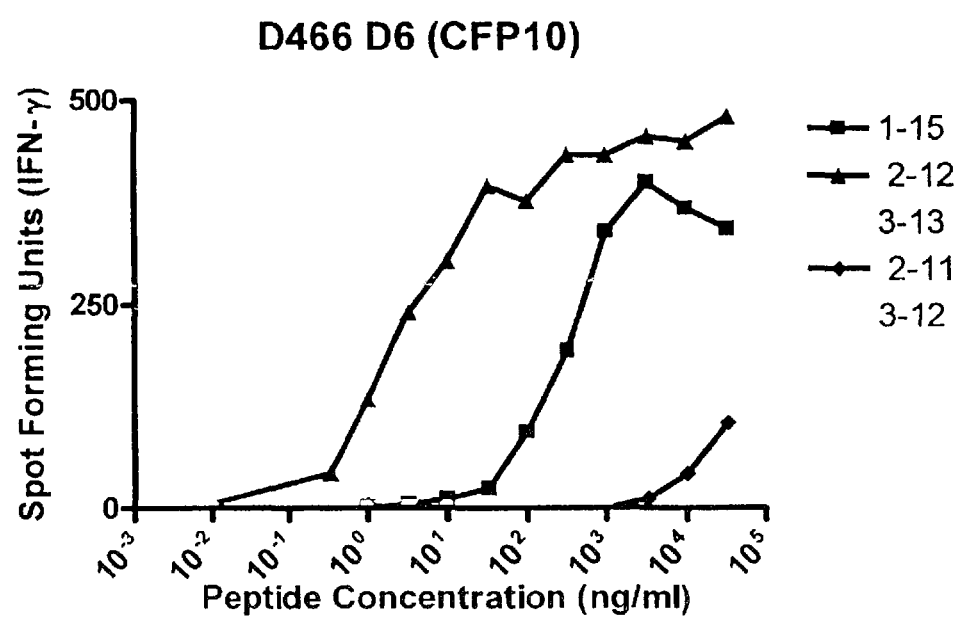
FIG. 4 is a line graph showing the confirmation of minimal epitope mapping of D466 D6. To confirm the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.
Figure 5:
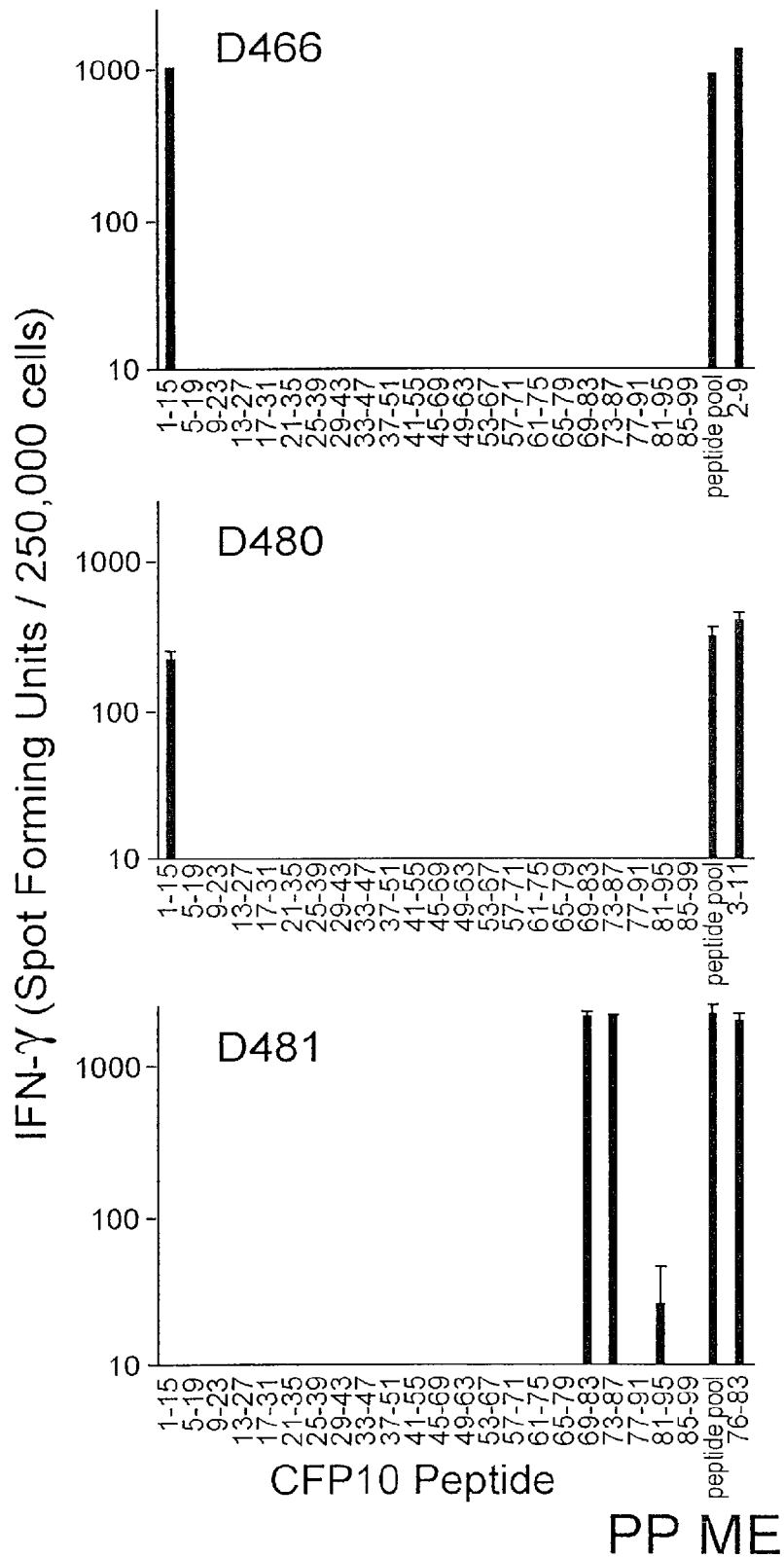
FIG. 5 is a set of bar graphs showing the profiling of immunodominance pattern for CFP10. To determine the effector cell frequencies, autologous DC (20,000/well) were pulsed either with each individual 15-mer peptide (5 μg/ml), the peptide pool (PP; 5 μg/each peptide) or the minimal epitope (ME) determined from T cell clones derived from each donor (D466:CFP10$_{2-11}$; D480:CFP10$_{3-11}$; D481: CFP10$_{75-83}$; 5 μg/ml), and tested against 250,000 magnetic bead purified CD8$^+$ T cells. IFN-γ release was assessed by ELISPOT after eighteen hours of co-culture. Each point represents the mean of duplicate determinations.
Figure 6A:
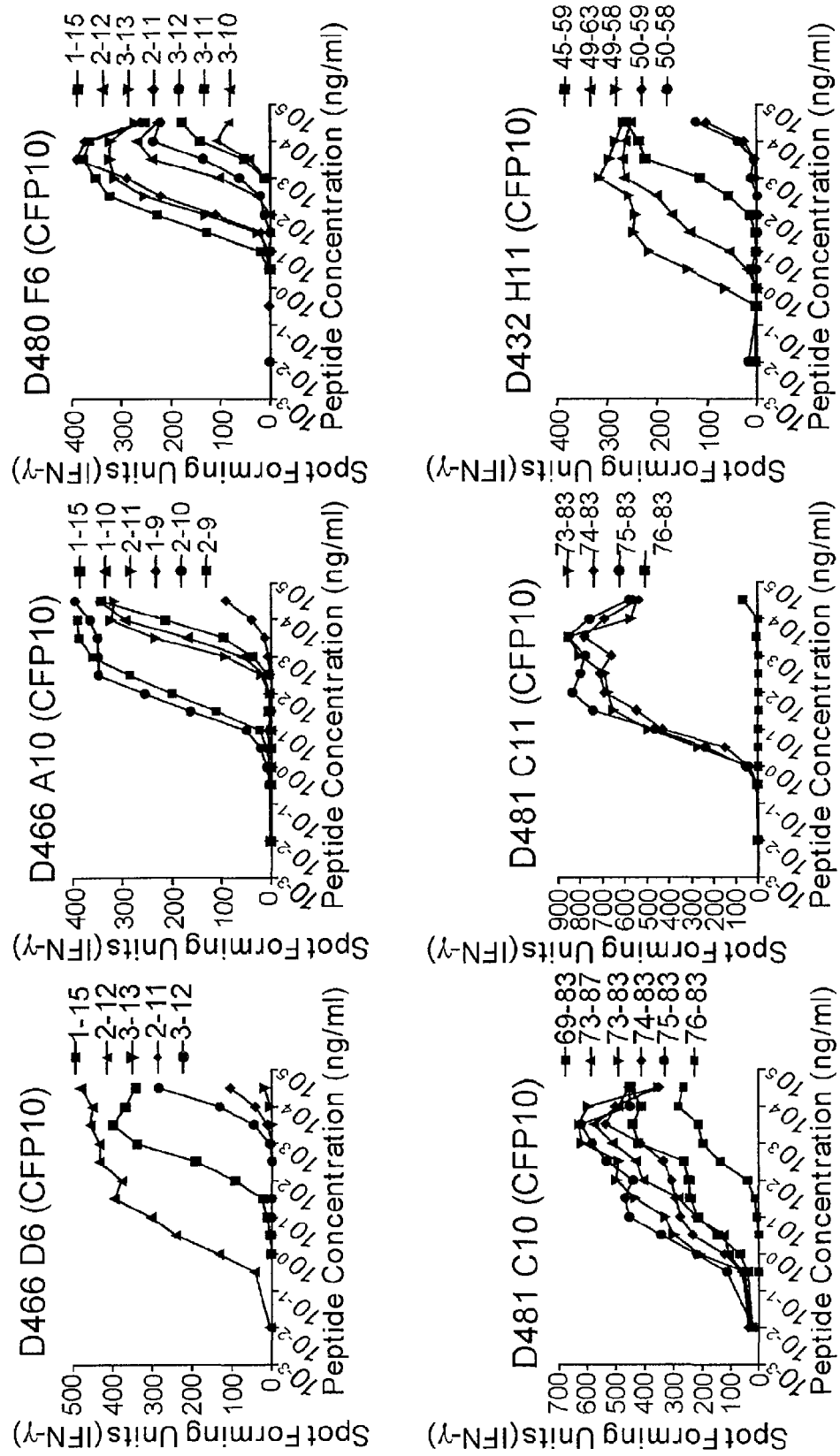
FIG. 6A-6B is a set of graphs summarizing the minimal epitope mapping data. To determine the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.
Figure 6B:
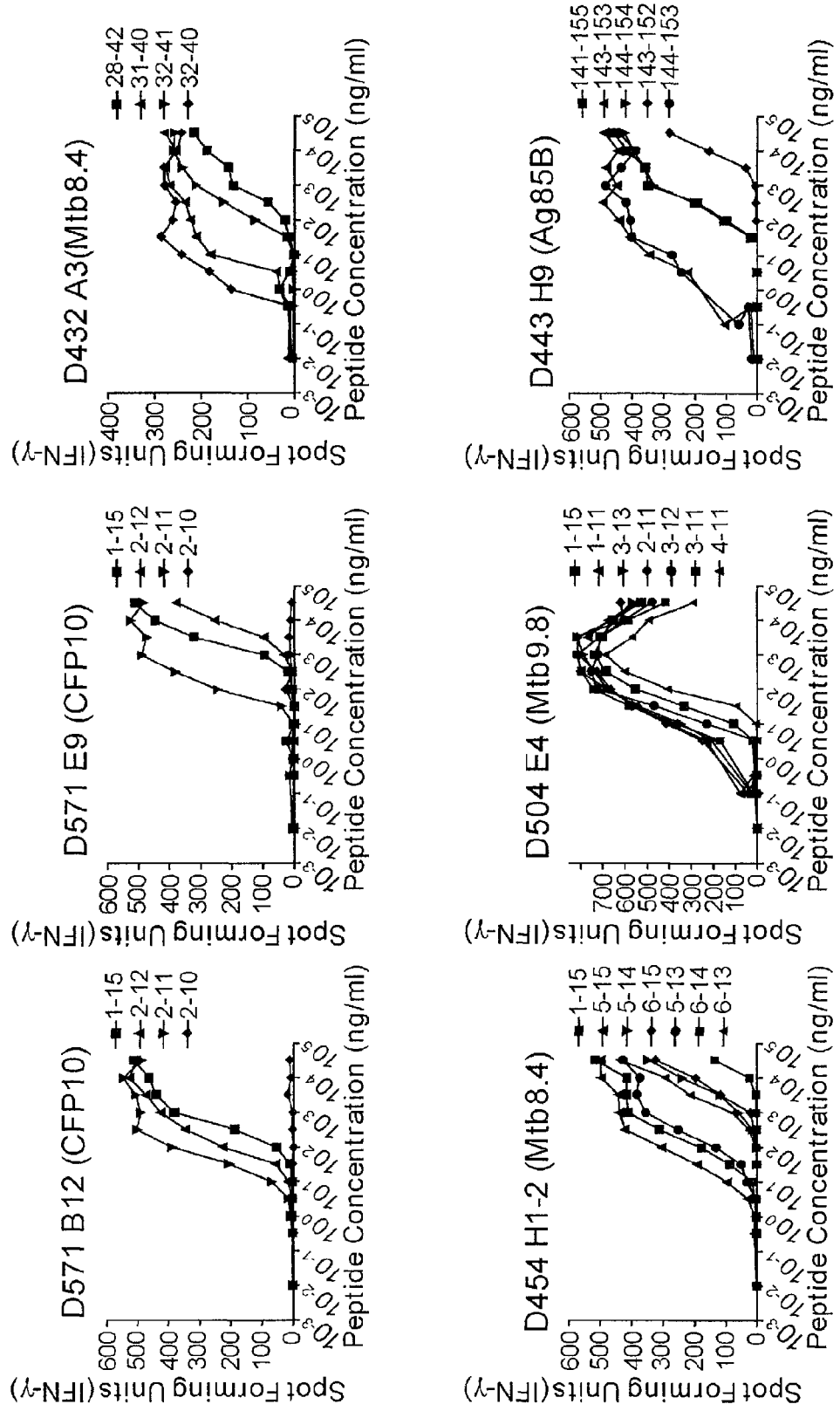

This approach is demonstrated in detail for a single representative clone, D466 D6, derived from a subject with active TB. As shown in FIG. 3A, testing the clone against autologous DC pulsed with a panel of peptide pools unambiguously defined the antigenic specificity as CFP10. The clone was then tested against each of the 15-mer peptides that comprise the CFP10 pool, revealing that the epitope was contained within CFP10$_{1-15}$ (FIG. 3B). Each possible 8 aa, 9 aa, 10 aa, and 11 aa peptide was then synthesized and tested for reactivity, revealing antigenic activity between aa 2-11 (FIG. 3C). Similarly, each clone was tested against lymphoblastoid cell lines (LCL) sharing at least one HLA-type with the donor (FIG. 3D). Autologous LCL and IHW 9058 LCL, which share B4501 and C1601, present the epitope to the clone, identifying both B4501 and C1601 as possible restricting alleles. However, C1601+ D433 LCL do not present the epitope, eliminating C1601 as a candidate restricting allele. Therefore D466 D6 is restricted by HLA-B4501. As demonstrated in FIG. 4, by testing each plausible epitope over a broad range of concentrations, the minimal epitope was defined as CFP10$_{2-10}$ for D466 D6. Experimental data supporting the assignment of the minimal epitope is provided for each clone in the supplemental Figure. A summary of the antigenic specificity, minimal epitope, and HLA-restricting allele is presented in Table III. Unexpectedly, all but one of the T cell clones were restricted by HLA-B alleles. Furthermore, a minority of those observed were 9 aa in length.

reflected immunodominant epitopes ex vivo. Two independent approaches were pursued, the first to determine if the response was present at high frequency, and the second to determine what proportion of the total response to the antigen is constituted by the epitope. To determine the ex-vivo effector cell frequency, as described in FIG. 1, each epitope was tested using autologous DC and magnetic bead purified CD8+ T cells derived from the donor from whom the T cell clones was isolated. A summary of the effector cell frequencies is presented in Table III. For the majority, the epitopes reflect high frequency responses, and thus could be considered a response that has been primed by exposure to Mtb. Notably, T cell clones isolated from four donors recognized CFP10. To determine if the epitopes defined reflected a substantial proportion of the total response to the antigen of interest, magnetic bead purified CD8+ T cells from three donors with sufficient available peripheral blood mononuclear cells (PBMC) were tested for reactivity to each individual 15-mer peptide, the peptide pool, and peptide representing the minimal epitope. As is demonstrated in FIG. 5, the ex vivo frequencies to the minimal epitope, 15-mer peptide(s) containing the minimal epitope, and peptide pool were remarkably concordant. These data suggested that for each donor a dominance hierarchy has been clearly established, and is reflected

TABLE III

Summary of Epitopes Identified

| Clone[a] | Gene | Accession Number | HLA-Restrict Allele | Epitope Locat'n | Epitope Sequence (SEQ ID NOS: 26-38) | # SFU[b] | MHC Bind. Aff.[c] | V beta region |
|---|---|---|---|---|---|---|---|---|
| D160 1-1B[d] (0) | CFP10 | Rv3874 | B44 | 2-11 | AEMKTDAATL | 360 | 38 | |
| D160 1-6F[d] (0) | CFP10 | Rv3874 | B14 | 85-94 | RADEEQQQAL | 120 | NA | |
| D432 H12 (2) | CFP10 | Rv3874 | B3514 | 49-58 | TAAQAAVVRF | 258 | 2011[e] | 5.3 |
| D466 A10 (10) | CFP10 | rv3874 | B4501 | 2-9 | AEMKTDAA | 2458 | 48 | IND |
| D466 D6 (1) | CFP10 | Rv3874 | B4501 | 2-12 | AEMKTDAATLA | 1993 | 6.2 | 22 |
| D481 C10 (10) | CFP10 | RV3874 | B1502 | 75-83 | NIRQAGVQY | 1715 | 14[f] | 9 |
| D481 C11 (1) | CFP10 | RV3874 | B1502 | 75-83 | NIRQAGVQY | 1715 | 14[f] | 13.6 |
| D480 F6 (6) | CFP10 | Rv3874 | B0801 | 3-11 | EMKTDAATL | 387 | 79 | 13.1 |
| D571 B12 (3) | CFP10 | Rv3874 | B4402 | 2-11 | AEMKTDAATL | 31 | 38 | IND |
| D571 E9 (4) | CFP10 | Rv3874 | B4402 | 2-11 | AEMKTDAATL | 31 | 38 | 14 |
| D504 E4 (1) | Mtb9.8 | Rv0287 | A0201 | 3-11 | LLDAHIPQL | <10 | 0.39 | 8 |
| D454 B10 (1) | Mtb9.8 | Rv0287 | B0801 | 33-61 | AAHARFVAA | 88 | 0.22 | IND |
| D454 H1-2 (1) | Mtb8.4 | Rv1174c | B1501 | 3-15 | AVINTTCNYGQ | 24 | 10 | 7.1 |
| D432 A3 (2) | Mtb 8.4 | Rv1174c | B3514 | 32-40 | ASPVAQSYL | 210 | 127[e] | 14 |
| D443 H9 (1) | Ag85B | Rv1886c | TBD | 144-153 | ELPQWLSANR | <10 | NA | 22 |

[a]Number of sister clones is in parentheses.
[b]# of SFU/250,000 CD8+ T cells is shown.
[c]IC50 in nm is shown.
[d]Publishrfd previously J Immunol. 2001 Jan. 1; 166(1)439-46.
[e]Measured binding affinity to B3501 is shown.
[f]Measured binding affinity to B1501 is shown.
NA = Not Available,
IND = Indeterminate
TBD = To be done.

Because each of the individual CD8+ T cell clones were derived based on growth of Mtb-infected DC, it was determined whether or not the antigen and epitopes identified in the original clones. Finally, as is noted in Table III, daughter clones of identical specificity were frequently identified, a result that would be predicted based on an immundominance hierarchy. TCR V beta staining was used to confirm the clonal relationship between daughter clones. Interestingly, in two cases, the identical minimal epitope and HLA-restriction was represented by two distinct clones (Table III).

Because much work on human CD8+ T cell responses to Mtb has relied upon the use of HLA-prediction algorithms, as each epitope was defined we asked whether or not the epitopes would have been predicted by these approaches. Many of these epitopes were not ranked strongly. This might highlight the limitations of those algorithms at the time they were used. To address this question experimentally, the $IC_{50}$ for each peptide that had been synthesized in the course of definition of the minimal epitope was determined against a panel of human HLA molecules. Shown in Table III is the $IC_{50}$ for the minimal epitope with the cognate restricting allele. The data demonstrated that the T cell epitopes bound avidly to HLA, and show a high degree of concordance between the T cell epitope data and HLA-binding data.

The data demonstrated that CD8+ T cell responses are present in persons infected with Mtb at frequencies that are comparable to that seen following many common viral infections such as vaccinia, influenza, and CMV. All but one of the epitopes that were mapped were restricted by HLA-B molecules. The data suggest that by using a T cell driven approach to epitope identification, dominant epitopes can be defined in humans infected with Mtb.

Example 3

Screening of T Cell Clones Against a Genomic Peptide Library

The classically-restricted and non-classically-restricted T cell clones (see Table II above) that did not recognize one of the known Mtb antigen peptide pools (Rv3875, Rv3874, Rv1886c, Rv0287, Rv3763, Rv1174c, Rv1196, Rv1793, Rv2346c, Rv1037c, Rv3619c and Rv1198) were screened against a genomic peptide library. This peptide library represents 389 genes, representing roughly 10% of the Mtb genome. The peptides are 15mers overlapping by 11 for each gene product. 50 nmol of each peptide was synthesized individually and then pooled into 777 pools of 50 peptides in a 96 well format (nine plates). Five blank wells and one well of an irrelevant peptide pool, SIV gag, were included on each of the nine plates. To screen the clones against the genomic peptide library, the clones are first expanded and tested against Mtb-infected DCs to ensure that each clone from this particular expansion yields a robust Mtb-specific signal in the ELISPOT assay. Then up to six T cell clones are pooled. For the screen, T cell clones (5,000 cells/well of each clone), autologous DCs (20,000 cells/well), IL-2 (0.5 ng/ml) and the peptide pools (5 ug/ml, individual peptides) were incubated overnight at 37 C in the ELISPOT assay. Only one technical replicate is done per pool because 5000 T cell clones per well with a peptide antigen produced an overwhelmingly positive response, resulting in a definitive result. Six classical clones from D504 were screened against the genomic peptide library, leading to the discovery of a new epitope. This epitope was from a family of four proteins that includes EsxJ, EsxW, EsxK and EsxP. These proteins share 98% homology and differ at only 3 amino acids. There is a fifth member of this family, EsxM (Rv1792), that was not included in the genomic peptide library.

The clones were screened against the individual fifteen-mers for these peptide pools. All six classical clones recognized EsxJ 21-35. This is a region of EsxJ that is identical to the other four members of this family. Next, 9, 10 and 11mer peptides were made from this 15mer and screened against each clone. The minimal epitope was determined to be EsxJ 24-34. In addition, the HLA restriction was found to be B5701.

Example 4

Additional Screening of T Cell Clones Against a Genomic Peptide Library

Eleven classical clones from D432B were screened against the genomic peptide library described above. The antigen was determined for two clones, which led to the identification of two novel epitopes, $PE\_PGRS42_{47-55}$ and $PE9_{53-67}$. The minimal epitope for one clone was determined to be $PE\_PGRS42_{47-55}$ and the HLA restriction was found to be B3514. The minimal epitope for the other clone is not yet determined, but is contained in the 15mer $PE9_{53-67}$. The HLA restriction for this clone was found to be B3905.

TABLE IV

Detail of Novel Epitopes from Genomic Peptide Library Screens.

| Clone | Gene | Accession Number | Epitope Location | Epitope | #SFU/ 250,000 CD8+ T-cells | MHC- Restriction | MHC Binding Affinity (IC50 nm) | TCR V beta region |
|---|---|---|---|---|---|---|---|---|
| D504 F9 (6) | EsxJ* | Rv1038c | 24-34 SEQ ID NO: 2 | QTVEDE- ARRMW | 84 | B5701 | TBD | Indeterminate |
| D432 D8 (1) | PE9 | Rv1088 | 53-67 SEQ ID NO: 7 | RLFNAN- AEEYHA- LSA | TBD | B3905 | TBD | 8 |
| D-132 H8 (1) | PE_PGRS42 | Rv2487c | 47-55 SEQ ID NO: 8 | VSAAIAG- LE | TBD | B3514 | TBD | 7.1 |

Number of clones recognizing epitope from each donor in parentheses. *This is a family of proteins that have almost identical sequences The family consists of Rv1038c, Rv1197, Rv2347, Rv3620c

TABLE V

Summary of Completed Clone Screens.

| Donor | TB Status | # Classical available (screened) | # Non-Classical available (screened) | # positive wells in screen | # of confirmed hits | # novel epitopes | # classical clones epitope identified | # classical clones epitope NOT identified |
|---|---|---|---|---|---|---|---|---|
| 426 | PPD+ | 1 (1) | 4 (4) | 1 | 0 | 0 | 0 | 1 |
| 431 | Active | 1 (1) | 1 (1) | 1** | 0 | 0 | 0 | 1 |
| 432 | Active | 11 (11) | 14 (7) | 11 | 3 | 2 | 3 | 8 |
| 454 | PPD+ | 1* (0) | 6 (4) | 0 | 0 | 0 | 0 | 0 |
| 466 | Active | 1 (1) | 4 (4) | 1 | 0 | 0 | 0 | 1 |
| 504 | PPD+ | 6 (6) | 9 (9) | 5 | 4 | 1 | 6 | 0 |
|  |  | 21 (20) | 38 (29) | 18 | 7 | 3 | 9 | 11 |

*The classical clone from D454 did not recognize Mtb upon re-expansion and was not screened against library.
**The classical clones from 426 and 431 were screened together, so there was one positive well between both clones.

Example 5

Screening of ex vivo CD8+ T-cells Against a Genomic Peptide Library

CD8+ T-cells from a LTBI donor, D610 (SE Asian) were screened against the genomic peptide library described above. Each plate of the genomic peptide library was screened in duplicate, for a total of 18 ELISPOT plates per screen. CD8+ T-cells were prepared from cryopreserved PBMC by CD8+ selection using magnetic bead separations. Resulting cell populations contained ≥96% CD8+ T cells. CD8+ T cells (250,000 cells/well), autologous DCs (20,000 cells/well), and IL-2 (0.5 ng/ml) were added to peptide (final 5 ug/ml, individual peptides) in the ELISPOT plates. Five media control wells are included on each plate. For each plate, the mean of these five wells was subtracted from each well of that plate to normalize between plates. Each technical replicate on each plate was then scored. A well was scored positive if the spot forming units (SFU), less the mean of the media wells, was greater than or equal to ten and the SFU was greater than or equal to twice the mean of the media. (Hudgens et al., *J. Immunol. Methods* 288: 19-34, 2004). This donor responded to the four peptide wells containing EsxJ, EsxW, EsxK and EsxP. CD8+ T-cells were then screened against each 15mer from these peptide pools and found to respond only to EsxJ 21-35, the same region of EsxJ, EsxW, EsxK and EsxP that is described in example 3 above.

Seven additional donors were screened against the genomic peptide library. The top 10 responses are detailed in Table 7. The four peptide pools highlighted in yellow contain peptides from only one gene. These four genes contain four novel epitopes.

TABLE 7

Top 10 Responses from Peptide Pool Screens of Seven Donors.
Spot Forming Units are for 250,000 CD8+ T-cells.

| Peptide Pool | Donor | Average SFU | RvNumbers Represented in Wells | Functional Category |
|---|---|---|---|---|
| C09_1 | D560 | 208.2 | Rv1860(50): | cell wall and cell processes |
| C12_4 | D545 | 156.4 | Rv0468(27): Rv0456c(23): | lipid metabolism |
| A04_3 | D454 | 136 | Rv0284(17): Rv0288(11): Rv0287(22) | cell wall and cell processes |
| B10_3 | D560 | 112.3 | Rv1273c(50): | cell wall and cell processes |
| E04_4 | D560 | 78.2 | Rv0152c(40): Rv0151c(10): | PE/PPE |

TABLE 7-continued

Top 10 Responses from Peptide Pool Screens of Seven Donors.
Spot Forming Units are for 250,000 CD8+ T-cells.

| Peptide Pool | Donor | Average SFU | RvNumbers Represented in Wells | Functional Category |
|---|---|---|---|---|
| G12_8 | D560 | 77.4 | Rv3478(18): Rv3507(32): | PE/PPE |
| E07_4 | D525 | 76.8 | Rv0159c(50): | PE/PPE |
| A10_8 | D560 | 70.4 | Rv3136(47): Rv3144c(3): | PE/PPE |
| E11_8 | D560 | 66.4 | Rv3350c(50): | PE/PPE |
| E08_9 | D545 | 60.2 | Rv1404(13): Rv2711(37): | regulatory proteins |

Example 6

Animal Models

In tuberculosis research, the mouse model has been used extensively to model various aspects of the disease. Mice can be infected by a variety of routes, including intravenous, intraperitoneal and tracheal. One route is aerosolization of the organism for respiratory infection. The mice are exposed to the aerosol in a chamber (wither whole body or nose only infection). The dose of invention can be varied by manipulating the concentration of Mtb in the nebulizer or time of exposure. A low dose infection, such as about 50 colony forming units (CFU) via aerosol results in a slow and steady increase in bacterial numbers in the lungs, generally reaching a peak in four weeks, which coincides with the peak number of T cells in the lungs. The initial period is considered the acute stage of infection. Following infection, there is a dissemination of bacteria to the mediastinal lymph nodes. T cell priming is generally detectable between two and three weeks. After about four weeks the bacterial numbers stabilize, and there is a slow progressive pathologic response. This system is of use for modeling active infection.

The ability of a composition of interest to prevent infection in an animal model can be evaluated using the methods described herein. The effectiveness of the composition of interest can be monitored by measuring the T cell response, such as the number of CD8+ or CD4+ T cells responding to an Mtb polypeptide in a biological sample. For these assays T cells with one are contacted with at least one *Mycobacterium* polypeptides, and an antigen presenting cell presenting the one or more *Mycobacterium* polypeptides. The *Mycobacterium* polypeptides include the amino acid sequence set forth as (a) one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or (b) at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11 or SEQ ID NO: 12, wherein the nine to twenty consecutive amino acids specifically bind major histocompatibility complex (MHC) class I. It is determined if the determining if the T cells specifically recognize the *Mycobacterium* polypeptide. An increase in the number of T cells that specifically recognize the Mtb polypeptide indicates that the composition is effective.

Exemplary animal models are described below (see also Repique et al., Infec. Immun. 70: 3318-3323, 2002, incorporated herein by reference for an additional protocol):

A. Short Term Mouse Model:

C57BL/6 mice are vaccinated with a composition according to the appropriate protocol and then rested for 4 to 6 weeks. Immunized mice are infected with a low dose aerosol 50-100 CFU) of virulent *M. tuberculosis* and protection is evaluated by assessing the number of viable bacilli 30 days post challenge.

Viable counts are performed on the lung and spleen of mice by homogenizing the organs and plating serial 10-fold dilutions on 7H11 agar plates. Plates are incubated for up to 21 days and the number of colony forming units per organ determined.

BCG vaccinated mice have approximately 1 Log 10 protection in their lung and spleen when compared to PBS-treated mice.

A biological sample is obtained prior to the administration of the composition of interest and after administration of the composition of interest. Alternatively, biological samples are obtained from vehicle treated animals and from animals treated with the composition of interest. An increase in the number of T cells that bind an Mtb polypeptide as disclosed herein indicates the composition is effective.

B. Short Term Guinea Pig Model

Out-bred Hartley guinea pigs are vaccinated with a composition including one or more Mtb polypeptide, or a polynucleotide encoding these one or more polypeptides and then rested for 8 to 10 weeks. Immunized guinea pigs are infected with a low dose aerosol (10-30 CFU) of virulent *M. tuberculosis* and protection is evaluated by assessing the number of viable bacilli 30 days post challenge.

Viable counts are performed on the lung and spleen of guinea pigs by homogenizing the organs and plating serial 10-fold dilutions on 7H11 agar plates. Plates are incubated for up to 21 days and the number of colony forming units per organ determined. Lung and spleen segments are also taken for histological analyses.

BCG vaccinated guinea pigs have approximately 2-3 $Log_{10}$ protection in their lung and spleen when compared to PBS-treated guinea pigs. In addition, BCG vaccinated guinea pigs have well defined granulomas when compared to unvaccinated animals.

A biological sample is obtained prior to the administration of the composition of interest and after administration of the composition of interest. Alternatively, biological samples are obtained from vehicle treated animals and from animals treated with the composition of interest. An increase in the number of T cells that bind an Mtb polypeptide as disclosed herein indicates the composition is effective.

C. Long Term Guinea Pig Model

The guinea pig model is similar to the mouse model, but the experiments are open-ended survival type and can last for as long as 2 years. Guinea pigs develop 'classical' granulomas similar to humans with active tuberculosis (TB), and as lung tissue necrosis progresses, they begin to lose weight and die of TB similar to humans. The number of colony forming units in the lungs and spleen can be assessed. Histological examination can also be performed to determine the degree of lung involvement and tissue destruction. After low-dose aerosol exposure in the guinea pig the number of organisms increases progressively during the first three weeks and then plateaus into a chronic state. During the later stages of infection there is increased bacterial load in the lung and this is associated with a worsening pathological condition. Without treatment, there is a concomitant rise in both CD4 and CD8 T cells in the lungs of infected guinea pigs.

Out-bred Hartley guinea pigs are vaccinated with the experimental vaccine according to the appropriate protocol and then rested for 8 to 10 weeks. Immunized guinea pigs are then infected with a low dose aerosol (10-30 CFU) of virulent *M. tuberculosis*. Guinea pigs are weighed weekly and monitored daily for signs of disease (such as increased respiration and failure to thrive). Unvaccinated guinea pigs succumb to infection from 20 to 25 weeks post challenge, while BCG vaccinated guinea pigs survive for 50 to 55 weeks post challenge.

At necropsy, the lung and spleen are assessed for the number of CFU and the extent of pathology. The relative protection of the experimental composition is compared to BCG vaccinated animals.

A biological sample is obtained prior to the administration of the composition of interest and after administration of the composition of interest. Alternatively, biological samples are obtained from vehicle treated animals and from animals treated with the composition of interest. An increase in the number of T cells that bind an Mtb polypeptide as disclosed herein indicates the composition is effective.

It will be apparent that the precise details of the methods or compositions described may be varied or modified without departing from the spirit of the described invention. We claim all such modifications and variations that fall within the scope and spirit of the claims below.

The invention claimed is:

1. A method for detecting *Mycobacterium tuberculosis* in a subject, comprising:
    contacting a biological sample from the subject, wherein the biological sample comprises T cells, with one or more-isolated *Mycobacterium* polypeptides in vitro, wherein one of the isolated *Mycobacterium* polypeptides comprises the amino acid sequence set forth as SEQ ID NO: 11; and
    performing an enzyme-linked immunospot assay that detects interferon-γ in order to determine if the T cells specifically recognize the *Mycobacterium* polypeptide, wherein a positive enzyme-linked immunospot assay that detects interferon-γ in the biological sample determines the presence of T cells that specifically recognize the *Mycobacterium* polypeptide and detects *Mycobacterium tuberculosis* in the subject.

2. The method of claim 1, wherein one of the isolated *Mycobacterium* polypeptides consists of the amino acid sequence set forth as SEQ ID NO: 11.

3. The method of claim 1, wherein the T cells are CD8+ T cells.

4. The method of claim 1, further comprising measuring the size of the T cells, the proliferation of the T cells, or a cell surface marker of the T cells.

5. The method of claim 1, wherein the biological sample is blood, isolated peripheral blood mononuclear cells, or isolated mononuclear cells.

6. The method of claim 1, wherein the biological sample is isolated T cells.

7. The method of claim 6, wherein the isolated T cells are cultured in vitro prior to contacting the biological sample with one or more-isolated *Mycobacterium* polypeptides, wherein one of the isolated *Mycobacterium* polypeptides comprises the amino acid sequence set forth as SEQ ID NO: 11.

8. The method of claim 6, wherein the T cells are cultured in vitro with antigen presenting cells.

9. The method of claim 7, wherein the one of the isolated *Mycobacterium* polypeptides consists of the amino acid sequence set forth as SEQ ID NO: 11.

10. A method for detecting a *Mycobacterium tuberculosis* infection in a subject, comprising:
    contacting ex vivo a biological sample from the subject, wherein the biological sample comprises T cells, with antigen presenting cells presenting one or more *Mycobacterium* polypeptides, wherein the amino acid sequence of one of the one or more *Mycobacterium* polypeptides comprises the amino acid sequence set forth as SEQ ID NO: 11; and
    contacting the sample with a capture monoclonal antibody that specifically binds interferon γ, wherein the capture monoclonal antibody is immobilized on a solid support, to form a complex; and
    contacting the sample with an additional labeled antibody that specifically binds interferon γ to detect the presence of the complex, wherein the presence of the labeled antibody bound to the complex indicates the presence of T cells that specifically recognize one of the *Mycobacterium* polypeptides and detects the *Mycobacterium tuberculosis* infection in the subject.

11. The method of claim 10, wherein the biological sample is blood, isolated peripheral blood mononuclear cells, or isolated mononuclear cells.

12. The method of claim 10, wherein the labeled monoclonal antibody is labeled with an enzyme, a fluorescent marker, biotin or a radioactive marker.

13. The method of claim 12, wherein the labeled monoclonal antibody is labeled with biotin, and the method further comprises contacting the sample with streptavidin conjugated to an enzyme, a fluorescent marker or a radioactive marker.

14. The method of claim 10, wherein the one of the isolated *Mycobacterium* polypeptides consists of the amino acid sequence set forth as SEQ ID NO: 11.

15. A method for detecting *Mycobacterium tuberculosis* in a subject, comprising:
    incubating a biological sample comprising $10^5$ to $10^7$ peripheral blood mononuclear cells isolated from the subject in vitro with one or more-isolated *Mycobacterium* polypeptides in a culture wherein one of the isolated *Mycobacterium* polypeptides comprises the amino acid sequence set forth as SEQ ID NO: 11 and is present at a concentration of $10^{-1}$ to $10^3$ μg per ml of the culture, and wherein the peripheral blood mononuclear cells are incubated with the polypeptide for about 4 to about 24 hours; and
    performing an assay in order to determine if T cells in the biological sample specifically recognize the *Mycobacterium* polypeptide, wherein the presence of T cells that specifically recognize the *Mycobacterium* polypeptide and detects *Mycobacterium tuberculosis* in the subject, wherein the assay comprises one or more of a) determining if the polypeptide binds T cells; b) evaluating cytolytic activity of the T cells; c) evaluating proliferation of the T cells, d) detecting the secretion of interferon gamma, interleukin-2 or tumor necrosis factor alpha, or e) any combination of a)-d).

16. The method of claim 15, wherein one of the isolated *Mycobacterium* polypeptides consists of the amino acid sequence set forth as SEQ ID NO: 11.

17. The method of claim 15, wherein the T cells are CD8+ T cells.

18. A method for detecting *Mycobacterium tuberculosis* in a subject, comprising:
    isolating CD8+ T cells from a biological sample from the subject;
    incubating the CD8+ T cells isolated from the subject in vitro with antigen presenting cells and with one or more-isolated *Mycobacterium* polypeptides in a culture, wherein one of the isolated *Mycobacterium* polypeptides comprises the amino acid sequence set forth as SEQ ID NO: 11 and is present at a concentration of $10^{-1}$ to $10^3$ μg per ml of the culture, and wherein the CD8+ T cells are incubated with the polypeptide for about 4 to about 24 hours; and
    performing an assay in order to determine if T cells in the biological sample specifically recognize the *Mycobacterium* polypeptide, wherein the presence of T cells that specifically recognize the *Mycobacterium* polypeptide and detects *Mycobacterium tuberculosis* in the subject, wherein the assay comprises one or more of a) determining if the polypeptide binds T cells; b) evaluating cytolytic activity of the T cells; c) evaluating proliferation of the T cells, d) detecting the secretion of interferon gamma, interleukin-2 or tumor necrosis factor alpha, or e) any combination of a)-d).

19. The method of claim 17, wherein one of the isolated *Mycobacterium* polypeptides consists of the amino acid sequence set forth as SEQ ID NO: 11.

* * * * *